United States Patent
Sterling et al.

(10) Patent No.: US 10,670,611 B2
(45) Date of Patent: Jun. 2, 2020

(54) CARDIOVASCULAR RISK EVENT PREDICTION AND USES THEREOF

(71) Applicant: SOMALOGIC, INC., Boulder, CO (US)

(72) Inventors: David Sterling, Boulder, CO (US); Shintaro Kato, Boulder, CO (US); Edward N. Brody, Boulder, CO (US); Stephen A. Williams, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 359 days.

(21) Appl. No.: 15/509,665

(22) PCT Filed: Nov. 3, 2014

(86) PCT No.: PCT/US2014/063714
§ 371 (c)(1),
(2) Date: Mar. 8, 2017

(87) PCT Pub. No.: WO2016/048388
PCT Pub. Date: Mar. 31, 2016

(65) Prior Publication Data
US 2018/0188267 A1    Jul. 5, 2018

Related U.S. Application Data

(60) Provisional application No. 62/055,984, filed on Sep. 26, 2014.

(51) Int. Cl.
| | |
|---|---|
| *G01N 33/68* | (2006.01) |
| *G16B 20/00* | (2019.01) |
| *G16B 40/00* | (2019.01) |
| *C12Q 1/6883* | (2018.01) |
| *G16H 50/20* | (2018.01) |
| *G06N 7/00* | (2006.01) |
| *G16H 50/30* | (2018.01) |
| *G01N 33/53* | (2006.01) |
| *G06Q 40/08* | (2012.01) |

(52) U.S. Cl.
CPC ....... *G01N 33/6893* (2013.01); *C12Q 1/6883* (2013.01); *G01N 33/5308* (2013.01); *G01N 33/6887* (2013.01); *G06N 7/005* (2013.01); *G06Q 40/08* (2013.01); *G16B 20/00* (2019.02); *G16B 40/00* (2019.02); *G16H 50/20* (2018.01); *G16H 50/30* (2018.01); *C12Q 2525/205* (2013.01); *G01N 2333/4712* (2013.01); *G01N 2333/4716* (2013.01); *G01N 2333/515* (2013.01); *G01N 2333/52* (2013.01); *G01N 2333/521* (2013.01); *G01N 2333/8121* (2013.01); *G01N 2333/96486* (2013.01); *G01N 2800/32* (2013.01); *G01N 2800/50* (2013.01); *G01N 2800/60* (2013.01)

(58) Field of Classification Search
CPC .......... G01N 33/6893; G01N 2570/00; G01N 2800/32; G01N 2800/324; C12Q 2600/106; C12Q 2600/112; C12Q 2600/118; C12Q 2600/158
USPC ............ 435/6.1, 6.11, 91.1, 91.31; 536/23.1, 536/24.5
See application file for complete search history.

(56) References Cited

U.S. PATENT DOCUMENTS

| | | | |
|---|---|---|---|
| 4,642,284 | A | 2/1987 | Cooper et al. |
| 4,945,039 | A | 7/1990 | Suzuki et al. |
| 5,587,291 | A | 12/1996 | Binder |
| 5,599,677 | A | 2/1997 | Dowell et al. |
| 5,631,136 | A | 5/1997 | Havemann et al. |
| 5,795,725 | A | 8/1998 | Buechler et al. |
| 5,834,220 | A | 11/1998 | Wicks et al. |
| 5,914,234 | A | 6/1999 | Lee et al. |
| 6,156,521 | A | 12/2000 | Buechler et al. |
| 6,174,686 | B1 | 1/2001 | Buechler et al. |
| 6,287,793 | B1 | 9/2001 | Schenk et al. |
| 6,461,828 | B1 | 10/2002 | Stanton et al. |
| 6,576,431 | B2 | 6/2003 | Reed et al. |
| 7,202,042 | B2 | 4/2007 | Buechler |
| RE39,816 | E | 9/2007 | Stanton et al. |
| 7,285,418 | B2 | 10/2007 | Katrukha et al. |
| 7,348,157 | B2 | 3/2008 | Eriksson et al. |
| 7,358,055 | B2 | 4/2008 | Valkirs et al. |

(Continued)

FOREIGN PATENT DOCUMENTS

| | | |
|---|---|---|
| EP | 0804736 | 3/1999 |
| EP | 0699306 | 9/1999 |

(Continued)

OTHER PUBLICATIONS

Goff et al., "2013 ACC/AHA Guideline of the Assessment of Cardiovascular Risk," JACC 2014, 63(25):2935-2959.

(Continued)

*Primary Examiner* — Jane J Zara

(74) *Attorney, Agent, or Firm* — McNeill Baur PLLC

(57) ABSTRACT

Methods and computer methods used to assess an individual for the prediction of risk of developing a Cardiovascular (CV) Event over a 1 to 5 year period are provided. The methods employ at least two biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin, or GDF11 in combination with FSTL3. The methods are particularly useful in predicting CV events in patients who suffer from coronary heart disease (CHD).

27 Claims, 25 Drawing Sheets

(56) References Cited

U.S. PATENT DOCUMENTS

| | | |
|---|---|---|
| 7,361,473 B2 | 4/2008 | Valkirs et al. |
| 7,371,582 B2 | 5/2008 | Nahm et al. |
| 7,374,950 B2 | 5/2008 | Kang et al. |
| 7,392,140 B2 | 6/2008 | Serena et al. |
| 7,416,857 B2 | 8/2008 | Lehmann et al. |
| 7,476,549 B2 | 1/2009 | Nahm et al. |
| 7,598,049 B2 | 10/2009 | Ray et al. |
| 7,604,946 B2 | 10/2009 | Buechler et al. |
| 7,608,406 B2 | 10/2009 | Valkirs et al. |
| 7,632,647 B2 | 12/2009 | Dahlen et al. |
| 7,638,292 B2 | 12/2009 | Eriksson et al. |
| 7,638,494 B2 | 12/2009 | Fogelman et al. |
| 7,655,415 B2 | 2/2010 | Lee |
| 7,659,062 B2 | 2/2010 | Santin |
| 7,666,583 B2 | 2/2010 | Mor et al. |
| 7,670,769 B2 | 3/2010 | Lee |
| 7,713,705 B2 | 5/2010 | Buechler et al. |
| 7,741,023 B2 | 6/2010 | Mitsuhashi |
| 7,759,080 B2 | 7/2010 | Maeshima et al. |
| 7,790,463 B2 | 9/2010 | Mor et al. |
| 7,838,250 B1 | 11/2010 | Goix et al. |
| 7,858,591 B2 | 12/2010 | Sullenger et al. |
| 7,871,769 B2 | 1/2011 | Baker et al. |
| 7,888,051 B2 | 2/2011 | Streeper et al. |
| 7,901,888 B2 | 3/2011 | Kebebew |
| 7,908,090 B2 | 3/2011 | Kim et al. |
| 8,084,224 B2 | 12/2011 | Buechler et al. |
| 8,119,393 B2 | 2/2012 | Qinwei |
| 8,143,233 B2 | 3/2012 | Sullenger et al. |
| 8,173,382 B2 | 5/2012 | Mattingly et al. |
| 8,183,000 B2 | 5/2012 | Block et al. |
| 8,232,065 B2 | 7/2012 | Urdea et al. |
| 8,283,330 B2 | 10/2012 | Sullenger et al. |
| 8,298,835 B2 | 10/2012 | Wang et al. |
| 8,334,105 B2 | 12/2012 | Jin |
| 8,338,189 B2 | 12/2012 | Lin et al. |
| 8,343,728 B2 | 1/2013 | Goix et al. |
| 8,357,497 B2 | 1/2013 | Urdea et al. |
| 8,404,448 B2 | 3/2013 | Ban et al. |
| 8,450,069 B2 | 5/2013 | Goix et al. |
| 8,486,652 B2 | 7/2013 | Larue et al. |
| 8,492,090 B2 | 7/2013 | Santin |
| 8,501,420 B2 | 8/2013 | Datwyler et al. |
| 8,510,245 B2 | 8/2013 | Stojadinovic et al. |
| 8,524,459 B2 | 9/2013 | Giuliani et al. |
| 8,535,891 B2 | 9/2013 | Kentsis et al. |
| 8,535,895 B2 | 9/2013 | Goix et al. |
| 8,586,524 B2 | 11/2013 | Sullenger et al. |
| 8,597,958 B2 | 12/2013 | Lee |
| 8,617,825 B2 | 12/2013 | Snider et al. |
| 8,628,929 B2 | 1/2014 | Yan et al. |
| 8,652,788 B2 | 2/2014 | Adamczyk et al. |
| 8,658,384 B2 | 2/2014 | Datwyler et al. |
| 8,734,769 B2 | 5/2014 | Lee |
| 8,748,110 B2 | 6/2014 | Snider et al. |
| 8,748,116 B2 | 6/2014 | Lee |
| 8,784,313 B2 | 7/2014 | Mebazaa et al. |
| 8,846,414 B2 | 9/2014 | Sista et al. |
| 8,871,453 B2 | 10/2014 | Kentsis et al. |
| 8,877,516 B2 | 11/2014 | Lin et al. |
| 8,906,606 B2 | 12/2014 | Gupta et al. |
| 8,932,808 B1 | 1/2015 | Sarwal et al. |
| 8,975,379 B2 | 3/2015 | Mor et al. |
| 8,986,530 B2 | 3/2015 | Ivory et al. |
| 9,012,162 B2 | 4/2015 | Gangadharan et al. |
| 9,068,991 B2 | 6/2015 | Goix et al. |
| 2002/0110523 A1 | 8/2002 | Kluft et al. |
| 2002/0127602 A1 | 9/2002 | Shi et al. |
| 2002/0197741 A1 | 12/2002 | Sabucedo et al. |
| 2003/0003503 A1 | 1/2003 | Tsai et al. |
| 2003/0040505 A1 | 2/2003 | Fogelman et al. |
| 2003/0077668 A1 | 4/2003 | Fogelman et al. |
| 2003/0199000 A1 | 10/2003 | Valkirs et al. |
| 2004/0018577 A1 | 1/2004 | Emerson et al. |
| 2004/0023309 A1 | 2/2004 | Noll |
| 2004/0175754 A1 | 9/2004 | Bar Or et al. |
| 2004/0186359 A1 | 9/2004 | Beaudoin et al. |
| 2004/0203083 A1 | 10/2004 | Buechler et al. |
| 2004/0253637 A1 | 12/2004 | Buechler et al. |
| 2005/0095591 A1 | 5/2005 | Christopherson et al. |
| 2005/0130193 A1 | 6/2005 | Luxon et al. |
| 2005/0130230 A1 | 6/2005 | Davalos et al. |
| 2005/0148029 A1 | 7/2005 | Buechler et al. |
| 2005/0164238 A1 | 7/2005 | Valkirs et al. |
| 2005/0164409 A1 | 7/2005 | Kiernan et al. |
| 2005/0181386 A1 | 8/2005 | Diamond et al. |
| 2005/0239706 A1 | 10/2005 | Backhed et al. |
| 2005/0260651 A1 | 11/2005 | Calias et al. |
| 2005/0272055 A1 | 12/2005 | Das et al. |
| 2006/0039863 A1 | 2/2006 | Schirner et al. |
| 2006/0105419 A1 | 5/2006 | Blackenberg et al. |
| 2006/0134698 A1 | 6/2006 | Jin |
| 2006/0199280 A1 | 9/2006 | Bar Or et al. |
| 2006/0275849 A1 | 12/2006 | Binger et al. |
| 2006/0286681 A1 | 12/2006 | Lehmann et al. |
| 2007/0092911 A1 | 4/2007 | Buechler et al. |
| 2007/0099239 A1 | 5/2007 | Tabibiazar et al. |
| 2007/0128663 A1 | 6/2007 | Kiernan et al. |
| 2007/0128734 A1 | 6/2007 | Kiernan et al. |
| 2007/0134814 A1 | 6/2007 | Kajander et al. |
| 2007/0154482 A1 | 7/2007 | Sukhatme et al. |
| 2007/0166776 A1 | 7/2007 | Noll |
| 2007/0218498 A1 | 9/2007 | Buechler et al. |
| 2007/0224643 A1 | 9/2007 | McPherson et al. |
| 2007/0243636 A1 | 10/2007 | Kiernan et al. |
| 2007/0269836 A1 | 11/2007 | McPherson et al. |
| 2008/0010024 A1 | 1/2008 | Diamond |
| 2008/0090759 A1 | 4/2008 | Kokenyesi et al. |
| 2008/0118924 A1 | 5/2008 | Buechler |
| 2008/0131907 A1 | 6/2008 | Wang et al. |
| 2008/0171341 A1 | 7/2008 | Orser et al. |
| 2008/0193461 A1 | 8/2008 | Jain et al. |
| 2008/0300797 A1 | 12/2008 | Tabibiazar et al. |
| 2008/0300798 A1 | 12/2008 | McDevitt et al. |
| 2008/0305512 A1 | 12/2008 | Mattingly et al. |
| 2009/0054741 A1 | 2/2009 | McAleer |
| 2009/0148860 A1 | 6/2009 | Van Eyk et al. |
| 2009/0197344 A1 | 8/2009 | Villard-Saussine et al. |
| 2009/0234202 A1 | 9/2009 | Goix et al. |
| 2009/0269356 A1 | 10/2009 | Epstein et al. |
| 2009/0299155 A1 | 12/2009 | Yang et al. |
| 2010/0009368 A1 | 1/2010 | Young |
| 2010/0016173 A1 | 1/2010 | Nagalla et al. |
| 2010/0055730 A1 | 3/2010 | Usheva-Simidjiyska et al. |
| 2010/0129851 A1 | 5/2010 | Van Eyk et al. |
| 2010/0167307 A1 | 7/2010 | Buechler et al. |
| 2010/0216256 A1 | 8/2010 | Cheng et al. |
| 2010/0255518 A1 | 10/2010 | Goix et al. |
| 2010/0260853 A1 | 10/2010 | Basran et al. |
| 2010/0267025 A1 | 10/2010 | Young |
| 2010/0323380 A1 | 12/2010 | Kapur et al. |
| 2011/0059089 A1 | 3/2011 | Swagemakers et al. |
| 2011/0076697 A1 | 3/2011 | Ruvinsky et al. |
| 2011/0077479 A1 | 3/2011 | Sloan et al. |
| 2011/0136141 A1 | 6/2011 | Adamczyk et al. |
| 2011/0144914 A1 | 6/2011 | Harrington et al. |
| 2011/0183316 A1 | 7/2011 | Siegel et al. |
| 2011/0250630 A1 | 10/2011 | Burton et al. |
| 2011/0257035 A1 | 10/2011 | Pena |
| 2011/0257140 A1 | 10/2011 | Jaisser et al. |
| 2011/0275060 A1 | 11/2011 | Ahearn et al. |
| 2011/0289035 A1 | 11/2011 | Stojadinovic et al. |
| 2011/0295782 A1 | 12/2011 | Stojadinovic et al. |
| 2012/0031773 A1 | 2/2012 | Miller |
| 2012/0034624 A1 | 2/2012 | Miller et al. |
| 2012/0040381 A1 | 2/2012 | Snider et al. |
| 2012/0065897 A1 | 3/2012 | Snider et al. |
| 2012/0115175 A1 | 5/2012 | Kapur et al. |
| 2012/0122717 A1 | 5/2012 | Satyaraj et al. |
| 2012/0142632 A1 | 6/2012 | Campbell |
| 2012/0178186 A1 | 7/2012 | Nieuwennhuis et al. |
| 2012/0208715 A1 | 8/2012 | McDevitt et al. |
| 2012/0219943 A1 | 8/2012 | Ky et al. |
| 2012/0231472 A1 | 9/2012 | Anderberg et al. |

(56) References Cited

U.S. PATENT DOCUMENTS

| | | |
|---|---|---|
| 2012/0258553 A1 | 10/2012 | Dittmer et al. |
| 2012/0309041 A1 | 12/2012 | Timmers et al. |
| 2012/0315263 A1 | 12/2012 | Olmstead |
| 2013/0023473 A1 | 1/2013 | Germain et al. |
| 2013/0085079 A1 | 4/2013 | Gill et al. |
| 2013/0101606 A1 | 4/2013 | Zhang et al. |
| 2013/0108549 A1 | 5/2013 | Orser et al. |
| 2013/0116135 A1 | 5/2013 | Doecke et al. |
| 2013/0150707 A1 | 6/2013 | Cima et al. |
| 2013/0165344 A1 | 6/2013 | Anderberg et al. |
| 2013/0183770 A1 | 7/2013 | Kushnir et al. |
| 2013/0230854 A1 | 9/2013 | Collier et al. |
| 2013/0230871 A1 | 9/2013 | Anderberg et al. |
| 2013/0252346 A1 | 9/2013 | Goix et al. |
| 2013/0260390 A1 | 10/2013 | Goix et al. |
| 2013/0288383 A1 | 10/2013 | Goix et al. |
| 2013/0330743 A1 | 12/2013 | Zhu |
| 2013/0330744 A1 | 12/2013 | Da Silva |
| 2013/0345805 A1 | 12/2013 | Sinder et al. |
| 2014/0017714 A1 | 1/2014 | Katrukha et al. |
| 2014/0024046 A1 | 1/2014 | De Kleijn et al. |
| 2014/0024553 A1 | 1/2014 | Michalek et al. |
| 2014/0051773 A1 | 2/2014 | Snider |
| 2014/0065648 A1 | 3/2014 | Wienhues-Thelen et al. |
| 2014/0120551 A1 | 5/2014 | Yang et al. |
| 2014/0147864 A1 | 5/2014 | Anderberg et al. |
| 2014/0147932 A1 | 5/2014 | Goix et al. |
| 2014/0179806 A1 | 6/2014 | Kain et al. |
| 2014/0199781 A1 | 7/2014 | Briscoe et al. |
| 2014/0206632 A1 | 7/2014 | Todd et al. |
| 2014/0227715 A1 | 8/2014 | Todd et al. |
| 2014/0242084 A1 | 8/2014 | Tan |
| 2014/0273007 A1 | 9/2014 | Love |
| 2014/0286944 A1 | 9/2014 | Snider et al. |
| 2014/0295432 A1 | 10/2014 | Evers et al. |
| 2014/0302055 A1 | 10/2014 | Zhong et al. |
| 2014/0308676 A1 | 10/2014 | Fert-Bober et al. |
| 2014/0370502 A1 | 12/2014 | Brennan et al. |
| 2014/0378377 A1 | 12/2014 | Yan et al. |
| 2015/0031049 A1 | 1/2015 | Kentsis et al. |
| 2015/0065372 A1 | 3/2015 | Amir et al. |
| 2015/0073820 A1 | 3/2015 | McEneaney |
| 2015/0079615 A1 | 3/2015 | Wienhues-Thelen et al. |
| 2015/0111776 A1 | 4/2015 | Chen |
| 2015/0119269 A1 | 4/2015 | McPherson et al. |
| 2015/0119275 A1 | 4/2015 | Todd et al. |
| 2015/0133326 A1 | 5/2015 | McManus et al. |
| 2015/0141273 A1 | 5/2015 | Bosch et al. |
| 2015/0168423 A1 | 6/2015 | Gill et al. |
| 2015/0177239 A1 | 6/2015 | Evers et al. |
| 2016/0305959 A1* | 10/2016 | Levy .......... G01N 33/6893 |
| 2018/0340022 A1* | 11/2018 | Lee .......... C07K 14/4703 |

FOREIGN PATENT DOCUMENTS

| | | |
|---|---|---|
| EP | 0784683 | 2/2001 |
| EP | 0965043 | 4/2002 |
| EP | 0938678 | 9/2003 |
| EP | 0915974 | 3/2004 |
| EP | 0821728 | 8/2004 |
| EP | 0776337 | 9/2005 |
| EP | 1473567 | 7/2006 |
| EP | 1485717 | 2/2007 |
| EP | 1633854 | 3/2009 |
| EP | 1322957 | 8/2009 |
| EP | 1786931 | 1/2010 |
| EP | 1666881 | 2/2010 |
| EP | 1649064 | 6/2011 |
| EP | 2372364 | 10/2011 |
| EP | 1532269 | 11/2011 |
| EP | 2211183 | 3/2013 |
| EP | 1423705 | 4/2013 |
| EP | 2026071 | 7/2013 |
| EP | 2336779 | 7/2013 |
| EP | 2359142 | 7/2013 |
| EP | 1896851 | 8/2013 |
| EP | 0935140 | 10/2013 |
| EP | 2121965 | 11/2013 |
| EP | 2232269 | 11/2013 |
| EP | 2305833 | 4/2014 |
| EP | 2532748 | 10/2014 |
| EP | 2386860 | 11/2014 |
| EP | 2325338 | 1/2015 |
| EP | 2664923 | 2/2015 |
| EP | 2521918 | 3/2015 |
| EP | 2386858 | 7/2015 |
| WO | WO 1996/011269 | 4/1996 |
| WO | WO 1997/026534 | 7/1997 |
| WO | WO 1998/029726 | 7/1998 |
| WO | WO 2002/063302 | 8/2002 |
| WO | WO 2003/097872 | 11/2003 |
| WO | WO 2004/005924 | 1/2004 |
| WO | WO 2004/092410 | 10/2004 |
| WO | WO 2006/120391 | 11/2006 |
| WO | 2007/002677 | 1/2007 |
| WO | WO 2007/070021 | 6/2007 |
| WO | WO-2008079269 A2 * | 7/2008 .......... C12Q 1/6886 |
| WO | WO 2009/108073 | 9/2009 |
| WO | WO 2009/118185 | 10/2009 |
| WO | 2010046411 A1 | 4/2010 |
| WO | WO 2011/017077 | 2/2011 |
| WO | WO 2011/123386 | 10/2011 |
| WO | WO 2011/143574 | 11/2011 |
| WO | WO 2012/001613 | 1/2012 |
| WO | WO 2012/052757 | 4/2012 |
| WO | 2013/049674 A1 | 4/2013 |
| WO | WO-2013049674 A1 * | 4/2013 .......... G01N 33/6893 |
| WO | WO 2013/085367 | 6/2013 |
| WO | WO 2013/152047 | 10/2013 |
| WO | WO 2013/169890 | 11/2013 |
| WO | WO 2014/004889 | 1/2014 |
| WO | WO 2014/093397 | 6/2014 |
| WO | WO 2014/122467 | 8/2014 |
| WO | WO 2014/144605 | 9/2014 |
| WO | WO 2014/187884 | 11/2014 |
| WO | WO 2015/034897 | 3/2015 |
| WO | WO 2015/036582 | 3/2015 |
| WO | WO 2015/042465 | 3/2015 |
| WO | WO 2015/063187 | 5/2015 |
| WO | WO 2015/085368 | 6/2015 |

OTHER PUBLICATIONS

Ayhan et al., "OP-276: Is There Association Between Acute Coronary Syndromes and Levels of Prostate Specific Antigen," International Journal of Cardiology 155(1):S1-S89 (2012).

Shlipak et al., "Biomarkers to Predict Recurrent Cardiovascular Disease: The Heart and Soul Study," The American Journal of Medicine, vol. 121, No. 1, Jan. 8, 2008, pp. 50-57.

Jguirim-Souissi et al., "Plasma Metalloproteinase-12 and Tissue Inhibitor of Metalloproteinase-1 Levels and Presence, Severity, and Outcome of Coronary Artery Disease," American Journal of Cardiology, vol. 100, No. 1, Jun. 25, 2007, pp. 23-27, Abstract.

Scholtes et al., "Carotid Atherosclerotic Plaque Matrix Metalloproteinase-12-Positive Macrophage Subpopulation Predicts Adverse Outcome After Endarterectomy," Journal of American Heart Association, vol. 1, No. 6, Nov. 29, 2002, pp. 1-15.

Motterle et al., "Influence of matrix metalloproteinase-12 on fibrinogen level," Atherosclerosis, vol. 220, No. 2, Nov. 11, 2011, Abstract.

International Search Report and Written Opinion issued in corresponding PCT Application No. PCT/US2014/063714, dated Aug. 26, 2015, 19 pages.

Ganz, "Aging," Presentation Slides from May 17, 2014, presented at the Goldlab Symposium 2014, 31 pages.

Williams, "Aphrodite and Medusa: Portraying the beauty and biology and the Gorgon of disease," Presentation Slides from May 17, 2014, presented at the Goldlab Symposium 2014, 40 pages.

(56) References Cited

OTHER PUBLICATIONS

Loffredo et al., "Growth Differentiation Factor 11 is a Circulating Factor that Reverses Age-Related Cardiac Hypertrophy," Cell, 153(4):828-839, May 9, 2013.

* cited by examiner

CARDIOVASCULAR RISK EVENT PREDICTION AND USES THEREOF

This application is a national phase entry pursuant to 35 U.S.C. § 371 of International Application No. PCT/US2014/063714, filed Nov. 3, 2014, which claims the benefit of U.S. Provisional Application No. 62/055,984, filed Sep. 26, 2014, each of which is incorporated by reference herein in its entirety for any purpose.

FIELD OF THE INVENTION

The present application relates generally to the detection of biomarkers and a method of evaluating the risk of a future cardiovascular event in an individual and, more specifically, to one or more biomarkers, methods, devices, reagents, systems, and kits used to assess an individual for the prediction of risk of developing a Cardiovascular (CV) Event over a 1 to 5 year period. Such Events include but are not limited to myocardial infarction, stroke, congestive heart failure or death.

BACKGROUND

The following description provides a summary of information relevant to the present application and is not an admission that any of the information provided or publications referenced herein is prior art to the present application.

Cardiovascular disease is the leading cause of death in the USA. There are a number of existing and important predictors of risk of primary events (D'Agostino, R et al., "General Cardiovascular Risk Profile for Use in Primary Care: The Framingham Heart Study" Circulation 117:743-53 (2008); and Ridker, P. et al., "Development and Validation of Improved Algorithms for the Assessment of Global Cardiovascular Risk in Women" JAMA 297(6):611-619 (2007)) and secondary events (Shlipak, M. et al. "Biomarkers to Predict Recurrent Cardiovascular Disease: The Heart & Soul Study" Am. J. Med. 121:50-57 (2008)) which are widely used in clinical practice and therapeutic trials. Unfortunately, the receiver-operating characteristic curves, hazard ratios, and concordance show that the performance of existing risk factors and biomarkers is modest (AUCs of ~0.75 mean that these factors are only halfway between a coin-flip and perfection). In addition to a need for improved diagnostic performance, there is a need for a risk product which is both near-term and personally responsive within individuals to beneficial (and destructive) interventions and lifestyle changes. The commonly utilized Framingham equation has three main problems. Firstly, it is too long term: it gives 10-year risk calculations but humans discount future risks and are reluctant to make behavior and lifestyle modifications based on them. Secondly, it is not very responsive to interventions: it is heavily dependent on chronological age, which cannot decline; and gender, which cannot change. Thirdly, within the high risk population envisioned here, the Framingham factors fail to discriminate well between high and low risk: the hazard ratio between high and low quartiles is only 2, and when one attempts to use Framingham scores to personalize risk by stratifying subjects into finer layers (deciles for example) the observed event rates are similar for many of the deciles.

Risk factors for cardiovascular disease are widely used to drive the intensity and the nature of medical treatment, and their use has undoubtedly contributed to the reduction in cardiovascular morbidity and mortality that has been observed over the past two decades. These factors have routinely been combined into algorithms but unfortunately they do not capture all of the risk (the most common initial presentation for heart disease is still death). In fact they probably only capture half the risk. An area under the ROC curve of ~0.76 is typical for such risk factors in primary prevention, with much worse performance in secondary prevention (0.62 is typical), numbers only about one quarter to one half of the performance between a coin-flip at 0.5 and perfection at 1.0.

The addition of novel biomarkers to clinical risk scores has been disappointing. For example, in the Framingham study (Wang et al., "Multiple Biomarkers for the Prediction of First Major Cardiovascular Events and Death" N. Eng. J. Med. 355:2631-2637 (2006)) in 3209 people, the addition of 10 biomarkers (CRP, BNP, NT-proBNP, aldosterone, renin, fibrinogen, D-dimer, plasminogen-activator inhibitor type 1, homocysteine and the urinary albumin to creatinine ratio), did not significantly improve the AUC when added to existing risk factors: the AUC for events 0-5 years was 0.76 with age, sex and conventional risk factors and 0.77 with the best combination of biomarkers added to the mix, and for secondary prevention the situation is worse.

Early identification of patients with higher risk of a cardiovascular event within a 1-5 year window is important because more aggressive treatment of individuals with elevated risk may improve outcome. Thus, optimal management requires aggressive intervention to reduce the risk of a cardiovascular event in those patients who are considered to have a higher risk, while patients with a lower risk of a cardiovascular event can be spared expensive and potentially invasive treatments, which are likely to have no beneficial effect to the patient.

Biomarker selection for the prediction of risk of having specific disease state or condition within a defined time period involves first the identification of markers that have a measurable and statistically significant relationship with the probability and/or timing of an event for a specific medical application. Biomarkers can include secreted or shed molecules that are either on the causal pathway to the condition of interest, or which are downstream or parallel to the disease or condition development or progression, or both. They are released into the blood stream from cardiovascular tissue or from other organs and surrounding tissues and circulating cells in response to the biological processes which predispose to a cardiovascular event or they may be reflective of downstream effects of the pathophysiology such as a decline in kidney function. Biomarkers can include small molecules, peptides, proteins, and nucleic acids. Some of the key issues that affect the identification of biomarkers include over-fitting of the available data and bias in the data.

A variety of methods have been utilized in an attempt to identify biomarkers and diagnose or predict the risk of having disease or a condition. For protein-based markers, these include two-dimensional electrophoresis, mass spectrometry, and immunoassay methods. For nucleic acid markers, these include mRNA expression profiles, microRNA profiles, FISH, serial analysis of gene expression (SAGE), large scale gene expression arrays, gene sequencing and genotyping (SNP or small variant analysis).

The utility of two-dimensional electrophoresis is limited by low detection sensitivity; issues with protein solubility, charge, and hydrophobicity; gel reproducibility; and the possibility of a single spot representing multiple proteins. For mass spectrometry, depending on the format used, limitations revolve around the sample processing and separation, sensitivity to low abundance proteins, signal to noise considerations, and inability to immediately identify the detected protein. Limitations in immunoassay approaches to biomarker discovery are centered on the inability of antibody-based multiplex assays to measure a large number of analytes. One might simply print an array of high-quality antibodies and, without sandwiches, measure the analytes bound to those antibodies. (This would be the formal equivalent of using a whole genome of nucleic acid sequences to measure by hybridization all DNA or RNA sequences in an organism or a cell. The hybridization experiment works because hybridization can be a stringent test for identity.) However, even very good antibodies are typically not stringent enough in selecting their binding partners to work in the context of blood or even cell extracts because the protein ensemble in those matrices have widely varying abundances, which can lead to poor signal to noise ratios. Thus, one must use a different approach with immunoassay-based approaches to biomarker discovery—one would need to use multiplexed ELISA assays (that is, sandwiches) to get sufficient stringency to measure many analytes simultaneously to decide which analytes are indeed biomarkers. Sandwich immunoassays do not scale to high content, and thus biomarker discovery using stringent sandwich immunoassays is not possible using standard array formats. Lastly, antibody reagents are subject to substantial lot variability and reagent instability. The instant platform for protein biomarker discovery overcomes this problem.

Many of these methods rely on or require some type of sample fractionation prior to the analysis. Thus the sample preparation required to run a sufficiently powered study designed to identify and discover statistically relevant biomarkers in a series of well-defined sample populations is extremely difficult, costly, and time consuming. During fractionation, a wide range of variability can be introduced into the various samples. For example, a potential marker could be unstable to the process, the concentration of the marker could be changed, inappropriate aggregation or disaggregation could occur, and inadvertent sample contamination could occur and thus obscure the subtle changes anticipated in early disease.

It is widely accepted that biomarker discovery and detection methods using these technologies have serious limitations for the identification of diagnostic or predictive biomarkers. These limitations include an inability to detect low-abundance biomarkers, an inability to consistently cover the entire dynamic range of the proteome, irreproducibility in sample processing and fractionation, and overall irreproducibility and lack of robustness of the method. Further, these studies have introduced biases into the data and not adequately addressed the complexity of the sample populations, including appropriate controls, in terms of the distribution and randomization required to identify and validate biomarkers within a target disease population.

Although efforts aimed at the discovery of new and effective biomarkers have gone on for several decades, the efforts have been largely unsuccessful. Biomarkers for various diseases typically have been identified in academic laboratories, usually through an accidental discovery while doing basic research on some disease process. Based on the discovery and with small amounts of clinical data, papers were published that suggested the identification of a new biomarker. Most of these proposed biomarkers, however, have not been confirmed as real or useful biomarkers, primarily because the small number of clinical samples tested provide only weak statistical proof that an effective biomarker has in fact been found. That is, the initial identification was not rigorous with respect to the basic elements of statistics. In each of the years 1994 through 2003, a search of the scientific literature shows that thousands of references directed to biomarkers were published. During that same time frame, however, the FDA approved for diagnostic use, at most, three new protein biomarkers a year, and in several years no new protein biomarkers were approved.

Based on the history of failed biomarker discovery efforts, theories have been proposed that further promote the general understanding that biomarkers for diagnosis, prognosis or prediction of risk of developing diseases and conditions are rare and difficult to find. Biomarker research based on 2D gels or mass spectrometry supports these notions. Very few useful biomarkers have been identified through these approaches. However, it is usually overlooked that 2D gel and mass spectrometry measure proteins that are present in blood at approximately 1 nM concentrations and higher, and that this ensemble of proteins may well be the least likely to change with disease or the development of a particular condition. Other than the instant biomarker discovery platform, proteomic biomarker discovery platforms that are able to accurately measure protein expression levels at much lower concentrations do not exist.

Much is known about biochemical pathways for complex human biology. Many biochemical pathways culminate in or are started by secreted proteins that work locally within the pathology; for example, growth factors are secreted to stimulate the replication of other cells in the pathology, and other factors are secreted to ward off the immune system, and so on. While many of these secreted proteins work in a paracrine fashion, some operate distally in the body. One skilled in the art with a basic understanding of biochemical pathways would understand that many pathology-specific proteins ought to exist in blood at concentrations below (even far below) the detection limits of 2D gels and mass spectrometry. What must precede the identification of this relatively abundant number of disease biomarkers is a proteomic platform that can analyze proteins at concentrations below those detectable by 2D gels or mass spectrometry.

As is discussed above, cardiovascular events may be prevented by aggressive treatment if the propensity for such events can be accurately determined, and by targeting such interventions at the people who need them the most and/or away from people who need them the least, medical resourcing efficiency can be improved and costs may be lowered at the same time. Additionally, when the patient has the knowledge of accurate and near-term information about their personal likelihood of cardiovascular events, this is less deniable than long-term population-based information and will lead to improved lifestyle choices and improved compliance with medication which will add to the benefits. Existing multi-marker tests either require the collection of multiple samples from an individual or require that a sample be partitioned between multiple assays. Optimally, an improved test would require only a single blood, urine or other sample, and a single assay. Accordingly, a need exists for biomarkers, methods, devices, reagents, systems, and kits that enable the prediction of Cardiovascular Events within a 5 year period.

SUMMARY OF THE INVENTION

The present application includes biomarkers, methods, reagents, devices, systems, and kits for the prediction of risk of having a Cardiovascular (CV) Event within a 1 year period, 2 year period, 3 year period, or 4 year period. The biomarkers of the present application were identified using a multiplex slow off rate aptamer (SOMAmer)-based assay which is described in detail herein. By using the SOMAmer-based biomarker identification method described herein, this application describes a set of biomarkers that are useful for predicting the likelihood of a CV event within 1 year, 2 years, 3 years, or 4 years.

Cardiovascular events may be avoided by aggressive treatment if the propensity for such events can be accurately determined. Prior art multi-marker tests either require the collection of multiple samples from an individual, or require that a sample be partitioned between multiple assays. It would be preferred to provide a prognostic assay that would require only a single biological sample, measured in a single assay, rather than multiple samples for different analyte types (lipids, proteins, metabolites) or panels of analytes. The central benefit to a single sample test is simplicity at the point of use, since a test with multiple sample collections and/or multiple types of technology (such as integrating blood results with one or more complimentary sources of information such as demographics, echocardiography, imaging, urine testing, blood pressure or vascular compliance) is more complex to administer and this forms a barrier to adoption. An additional advantage derives from running that single sample in a single assay for multiple proteins. A single assay should mitigate unwanted variation due to calibrating multiple assay results or technology formats together. The test which forms the basis of this application is such a "single sample, single assay" test. This combination of single sample and single assay is a novel feature of this cardiovascular event risk test which addresses the logistic complexity of collecting multiple samples and using multiple measurement modalities and the problems and biohazards involved in splitting samples into multiple aliquots for multiple independent analytical procedures.

Cardiovascular disease is known to involve multiple biological processes and tissues. Well known examples of biological systems and processes associated with cardiovascular disease are inflammation, thrombosis, disease-associated angiogenesis, platelet activation, macrophage activation, liver acute response, extracellular matrix remodeling, and renal function. These processes can be observed as a function of gender, menopausal status, and age, and according to status of coagulation and vascular function. Since these systems communicate partially through protein based signaling systems, and multiple proteins may be measured in a single blood sample, the invention provides a single sample, single assay multiple protein based test focused on proteins from the specific biological systems and processes involved in cardiovascular disease.

As is discussed herein, one of the central functions of measuring risk for a cardiovascular event is to enable the assessment of progress in response to treatment and behavioral changes such as diet and exercise. Current risk prediction methods such as the Framingham equation, include clearly unresponsive clinical covariate information, key factors are the age and gender of the subject. This makes the Framingham equation less useful for monitoring the change in an individual's risk, although it may be accurate for a population. A novel feature of this CV event risk test is that it does not require age as a part of the prognostic model. The subject invention is based on the premise that, within the biology of aging, there are underlying biological factors which are more directly associated with risk, but which are variable between individuals and thus better used to assess risk than chronological age. The invention is premised on the belief that age itself is not a causal factor in the disease, and that age is acting as a surrogate or proxy for the underlying biology. While age is indeed prognostic of CV events, it cannot be used to assess individual improvement, and presumably the effect of age is mediated through biological function. This effect can be better determined through measurement of the relevant biology. In this invention, the proteins that are targeted are involved in the biology of the disease. Thus, the invention captures the biological information that is reflected in the correlation between age and risk of a CV event.

The strategy to identify proteins from multiple processes involved in cardiovascular disease necessitated choosing parameters that provided a wide range/diversity of CV disease patients presenting with a variety of events or symptoms. Events due to cardiovascular disease are heterogeneous, involving sudden death of unknown cause, and two main classes of known event: thrombotic (stroke, transient ischemic attacks, myocardial infarction) and CHF related events. Some presenting events may lack specific diagnostic information (e.g., death at home). In view of these characteristics of CV disease, the inventive test was developed by measuring proteins involved from the biological processes associated with CV disease, on blood samples from a broad range of events. This strategy resulted in the inclusion of information from multiple processes involved in the disease (e.g., angiogenesis, platelet activation, macrophage activation, liver acute response, other lymphocyte inflammation, extracellular matrix remodeling, and renal function). In order to develop a multiple protein based prognostic single sample test for CV disease, the chosen study population was a cohort study of high risk group of subjects with apparently stable coronary heart disease: the "Heart & Soul" study. By choosing this set of subjects with a high rate of CV events, it was possible to determine risk associated with protein measurements more accurately than would have been possible in the general population (within which events are rarer). The development of the subject test on this high risk group, permitted identification of protein biomarker combinations that could be generalized due to common biology. As a result, the subject inventive test and biomarkers are likely to be effective beyond event prediction in a larger population than those individuals matching the entry criteria of the "Heart & Soul" study.

In some embodiments, methods for screening a subject for the risk of a cardiovascular event (CV) event are provided. In some embodiments, a method comprises
(a) forming a biomarker panel comprising N biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin, wherein N is an integer from 2 to 9; and
(b) detecting the level of each of the N biomarkers of the panel in a sample from the subject.

In some embodiments, methods for predicting the likelihood that a subject will have a CV event are provided. In some embodiments, a method comprises
(a) forming a biomarker panel comprising N biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin, wherein N is an integer from 2 to 9; and
(b) detecting the level of each of the N biomarkers of the panel in a sample from the subject.

In some embodiments, methods for screening a subject for the risk of a cardiovascular event (CV) event are provided, comprising detecting the level of at least five, at least six, at least seven, at least eight, or all nine biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin in a sample from the subject.

In some embodiments, methods for predicting the likelihood that a subject will have a CV event are provided, comprising detecting the level of at least five, at least six, at least seven, at least eight, or all nine biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin in a sample from the subject.

In some embodiment, the likelihood of the subject having a CV event within 4 years is high if the level of at least five, at least six, or all seven biomarkers selected from the level of MMP12, angiopoetin-2, complement C7, cardiac troponin I, angiopoietin-related protein 4, CCL18/PARC and alpha1-antichymotrypsin complex is higher than a control level of the respective protein, and if the level of at least one biomarker or both biomarkers selected from GDF11 and alpha2-antiplasmin is lower than a control level level of the respective protein.

In some embodiments, methods for screening a subject for the risk of a cardiovascular event (CV) event are provided, comprising detecting the level of GDF11 and FSTL3 in a sample from the subject.

In some embodiments, methods for predicting the likelihood that a subject will have a CV event are provided, comprising detecting the level of GDF11 and FSTL3 in a sample from the subject. In some embodiments, methods for predicting the likelihood that a subject will have a thrombotic event are provided, comprising detecting the level of GDF11 and FSTL3 in a sample from the subject. In some embodiments, the thrombotic even is selected from myocardial infarction, stroke, and transient ischemic attack.

In some embodiments, the likelihood of the subject having a CV event (such as a thrombotic event) within 4 years is high if the level of GDF11 is lower than a control level of GDF11 and/or the level of FSTL3 is higher than a control level of FSTL3.

In some embodiments, the method comprises detecting the level of MMP12. In some embodiments, the method comprises detecting the level of angiopoietin-2. In some embodiments, the method comprises detecting the level of complement C7. In some embodiments, the method comprises detecting the level of cardiac troponin I. In some embodiments, the method comprises detecting the level of angiopoietin-related protein 4. In some embodiments, the method comprises detecting the level of CCL18/PARC. In some embodiments, the method comprises detecting the level of alpha-1-antichymotrypsin complex. In some embodiments, the method comprises detecting the level of GDF11. In some embodiments, the method comprises detecting the level of and alpha-2-antiplasmin. In some embodiments, the method comprises detecting the level of MMP12, angiopoietin-2, complement C7, cardiac troponin I, angiopoietin-related protein 4, CCL18/PARC, alpha-1-antichymotrypsin complex, GDF11 and alpha-2-antiplasmin.

In some embodiments, the subject has coronary artery disease. In some embodiments, the subject does not have a history of CV events. In some embodiments, the subject has a high American College of Cardiology (ACC) risk score. In some embodiments, the subject has an intermediate ACC risk score. In some embodiments, the subject has a low ACC risk score. In some embodiments, the subject has had at least one CV event. In some embodiments, the CV event is selected from myocardial infarction, stroke, congestive heart failure, transgenic ischemic attack, and death.

In some embodiments, the sample is selected from a blood sample, a serum sample, a plasma sample, and a urine sample. In some embodiments, the sample is a plasma sample. In some embodiments, the method is performed in vitro.

In some embodiments, each biomarker is a protein biomarker. In some embodiments, the method comprises contacting biomarkers of the sample from the subject with a set of biomarker capture reagents, wherein each biomarker capture reagent of the set of biomarker capture reagents specifically binds to a different biomarker being detected. In some embodiments, each biomarker capture reagent is an antibody or an aptamer. In some embodiments, each biomarker capture reagent is an aptamer. In some embodiments, at least one aptamer is a slow off-rate aptamer. In some embodiments, at least one slow off-rate aptamer comprises at least one, at least two, at least three, at least four, at least five, at least six, at least seven, at least eight, at least nine, or at least 10 nucleotides with modifications. In some embodiments, each slow off-rate aptamer binds to its target protein with an off rate (t½) of ≥30 minutes, ≥60 minutes, ≥90 minutes, ≥120 minutes, ≥150 minutes, ≥180 minutes, ≥210 minutes, or ≥240 minutes.

In some embodiments, the likelihood of a CV event is based on the biomarker levels and at least one item of additional biomedical information selected from a) information corresponding to the presence of cardiovascular risk factors selected from the group consisting of prior myocardial infarction, angiographic evidence of greater than 50% stenosis in one or more coronary vessels, exercise-induced ischemia by treadmill or nuclear testing or prior coronary revascularization, b) information corresponding to physical descriptors of said individual, c) information corresponding to a change in weight of said individual, d) information corresponding to the ethnicity of said individual, e) information corresponding to the gender of said individual, f) information corresponding to said individual's smoking history, g) information corresponding to said individual's alcohol use history, h) information corresponding to said individual's occupational history, i) information corresponding to said individual's family history of cardiovascular disease or other circulatory system conditions, j) information corresponding to the presence or absence in said individual of at least one genetic marker correlating with a higher risk of cardiovascular disease in said individual or a family member of said individual, k) information corresponding to clinical symptoms of said individual, l) information corresponding to other laboratory tests, m) information corresponding to gene expression values of said individual, and n) information corresponding to said individual's consumption of known cardiovascular risk factors such as diet high in saturated fats, high salt, high cholesterol, o) information corresponding to the individual's imaging results obtained by techniques selected from the group consisting of electrocardiogram, echocardiography, carotid ultrasound for intima-media thickness, flow mediated dilation, pulse wave velocity, ankle-brachial index, stress echocardiography, myocardial perfusion imaging, coronary calcium by CT, high resolution CT angiography, MM imaging, and other imaging modalities, p) information regarding the individual's medications, and q) information regarding the individual's kidney function.

In some embodiments, the method comprises determining the likelihood of a CV Event for the purpose of determining a medical insurance premium or life insurance premium. In some embodiments, the method further comprises determining coverage or premium for medical insurance or life insurance. In some embodiments, the method further comprises using information resulting from the method to predict and/or manage the utilization of medical resources. In some embodiments, the method further comprises using information resulting from the method to enable a decision to acquire or purchase a medical practice, hospital, or company.

In some embodiments, a computer-implemented method for evaluating the risk of a cardiovascular (CV) event is provided. In some embodiments, the method comprises retrieving on a computer biomarker information for a subject, wherein the biomarker information comprises the levels of at least five, at least six, at least seven, at least eight, or all nine biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin in a sample from the subject; performing with the computer a classification of each of said biomarker values; indicating a result of the evaluation of risk for a CV event for said individual based upon a plurality of classifications. In some embodiments, indicating the result of the evaluation of risk of a CV event for the subject comprises displaying the result on a computer display.

DETAILED DESCRIPTION

Figure 1:
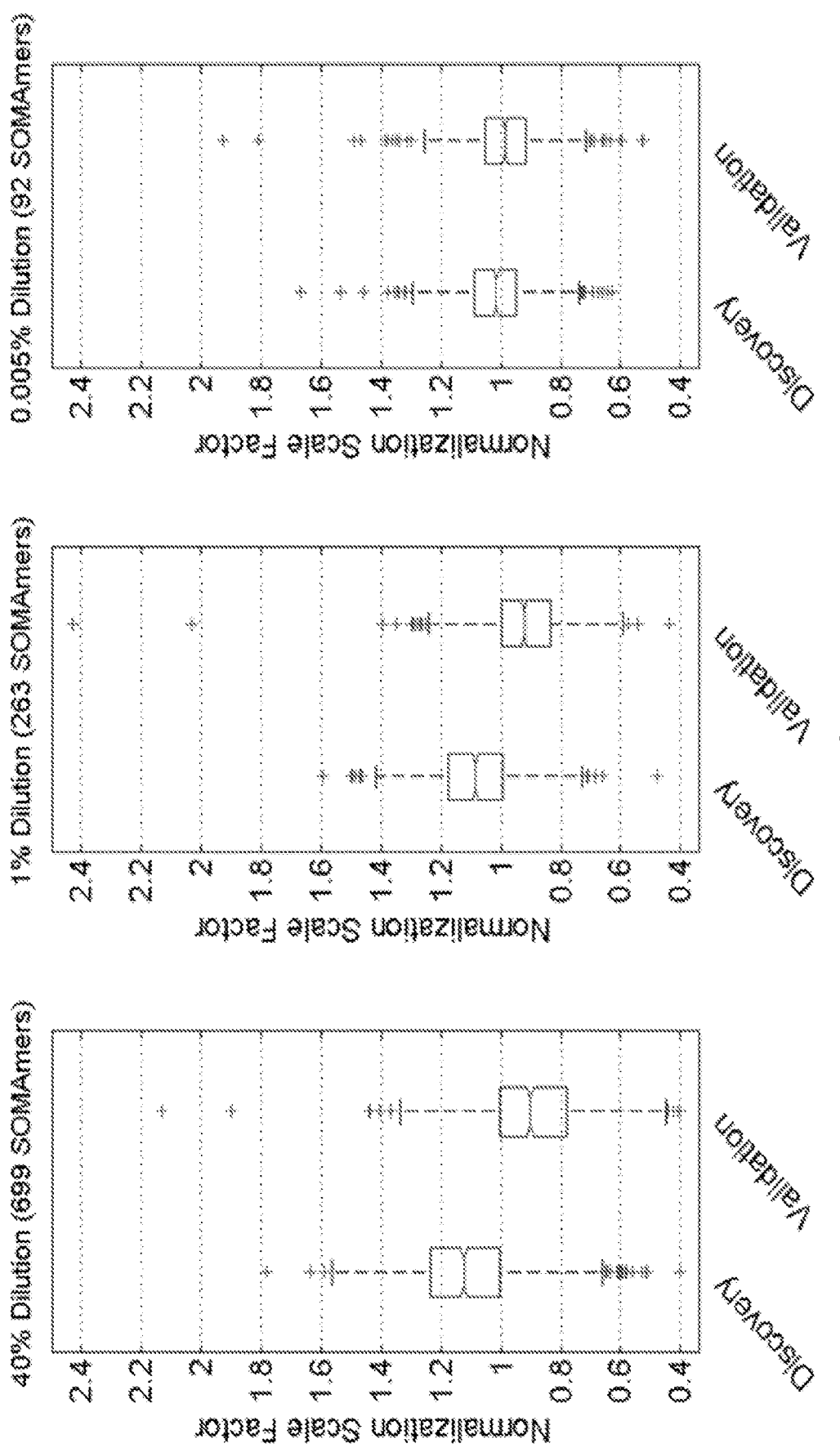
FIG. 1 shows box plots of normalization scale factor distribution for proteins measured in discovery and validation sets at each sample dilution. In the box plots the red line indicates median value, the extent of the box displays the inter-quartile range containing 50% of the data and the whiskers extend 1.5× the inter-quartile range out from the box. Samples with extreme normalization scale factors are marked with red "+" sign. Normalization increases (decreases) median signal levels in discovery (validation) set to compensate for the systematic intensity bias evident in protein signal measured in the validation samples.

While the invention will be described in conjunction with certain representative embodiments, it will be understood that the invention is defined by the claims, and is not limited to those embodiments.

One skilled in the art will recognize many methods and materials similar or equivalent to those described herein may be used in the practice of the present invention. The present invention is in no way limited to the methods and materials described.

Unless defined otherwise, technical and scientific terms used herein have the meaning commonly understood by one of ordinary skill in the art to which this invention belongs. Although any methods, devices, and materials similar or equivalent to those described herein can be used in the practice of the invention, certain methods, devices, and materials are described herein.

All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include the plural, unless the context clearly dictates otherwise, and may be used interchangeably with "at least one" and "one or more." Thus, reference to "an aptamer" includes mixtures of aptamers, reference to "a probe" includes mixtures of probes, and the like.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements may include other elements not expressly listed.

The present application includes biomarkers, methods, devices, reagents, systems, and kits for the prediction of risk of near-term CV events within a defined period of time, such as within 1 year, within 2 years, within 3 years, or within 4 years.

"Cardiovascular Event" means a failure or malfunction of any part of the circulatory system. In one embodiment, "Cardiovascular Event" means stroke, transient ischemic attack (TIA), myocardial infarction (MI), sudden death attributable to malfunction of the circulatory system, and/or heart failure, or sudden death of unknown cause in a population where the most likely cause is cardiovascular. In another embodiment, "Cardiovascular Event" means any of the foregoing malfunctions and/or unstable angina, need for stent or angioplasty, or the like.

Cardiovascular Events include "Congestive Heart Failure" or "CHF" and "thrombotic events." Thrombotic Events include MIs, transient ischemic attacks (TIA), stroke, acute coronary syndrome and need for coronary re-vascularization.

In certain embodiments, biomarkers are provided for use either alone or in various combinations to evaluate the risk of sudden death or a future CV event within a 4 year time period with CV events defined as myocardial infarction, stroke, death and congestive heart failure. Thrombotic events consist of myocardial infarction and stroke combined. As described in detail below, exemplary embodiments include the biomarkers provided in Table 3, which were identified using a multiplex SOMAmer-based assay that is described generally in the Examples.

While certain of the described CV event biomarkers may be useful alone for evaluating the risk of a CV event, methods are also described herein for the grouping of multiple subsets of the CV event biomarkers, where each grouping or subset selection is useful as a panel of three or more biomarkers, interchangeably referred to herein as a "biomarker panel" and a panel. Thus, various embodiments of the instant application provide combinations comprising at least five, art least six, at least seven, at least eight, or all nine of the biomarkers in Table 3.

In one embodiment, the number of biomarkers useful for a biomarker subset or panel is based on the sensitivity and specificity value for the particular combination of biomarker values. The terms "sensitivity" and "specificity" are used herein with respect to the ability to correctly classify an individual, based on one or more biomarker values detected in their biological sample, as having an increased risk of having a CV Event within 4 years or not having increased risk of having a CV event within the same time period. "Sensitivity" indicates the performance of the biomarker(s) with respect to correctly classifying individuals that have increased risk of a CV event. "Specificity" indicates the performance of the biomarker(s) with respect to correctly classifying individuals who do not have increased risk of a CV event. For example, 85% specificity and 90% sensitivity for a panel of markers used to test a set of Event Negative samples and Event Positive samples indicates that 85% of the control samples were correctly classified as Event Negative samples by the panel, and 90% of the Event Positive samples were correctly classified as Event Positive samples by the panel.

In an alternate method, scores may be reported on a continuous range, with a threshold of high, intermediate or low risk of a CV event within a defined unit of time, with thresholds determined based on clinical findings; an alternate expression of the same data is to fix the threshold of probability (such as 50%) and to predict the time at which this proportion of subjects would have their event (e.g., analogous to half-life in radioactive decay, the time at which half the isotope would have decayed).

A factor that can affect the number of biomarkers to be used in a subset or panel of biomarkers is the procedures used to obtain biological samples from individuals who are being assessed for risk of a CV event. In a carefully controlled sample procurement environment, the number of biomarkers necessary to meet desired sensitivity and specificity and/or threshold values will be lower than in a situation where there can be more variation in sample collection, handling and storage. Alternatively, a higher sensitivity and specificity may be obtained by using more markers that are less robust to the sample procurement (e.g., which do not survive in a variable collection situation) along with sample handling markers that enable rejection of poorly collected samples or the elimination of sensitive markers from the risk prediction algorithm.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, urine, saliva, peritoneal washings, ascites, cystic fluid, glandular fluid, lymph fluid, bronchial aspirate, synovial fluid, joint aspirate, organ secretions, cells, a cellular extract, and cerebrospinal fluid. This also includes experimentally separated fractions of all of the preceding. For example, a blood sample can be fractionated into serum, plasma, or into fractions containing particular types of blood cells, such as red blood cells or white blood cells (leukocytes). In some embodiments, a blood sample is a dried blood spot. In some embodiments, a plasma sample is a dried plasma spot. In some embodiments, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Exemplary tissues susceptible to fine needle aspiration include lymph node, lung, thyroid, breast, pancreas, and liver. Samples can also be collected, e.g., by micro dissection (e.g., laser capture micro dissection (LCM) or laser micro dissection (LIVID)), bladder wash, smear (e.g., a PAP smear), or ductal lavage. A "biological sample" obtained or derived from an individual includes any such sample that has been processed in any suitable manner after being obtained from the individual. In some embodiments, a biological sample is a plasma sample.

Further, in some embodiments, a biological sample may be derived by taking biological samples from a number of individuals and pooling them, or pooling an aliquot of each individual's biological sample. The pooled sample may be treated as described herein for a sample from a single individual, and, for example, if a poor prognosis is established in the pooled sample, then each individual biological sample can be re-tested to determine which individual(s) have an increased or decreased risk of a CV event.

For purposes of this specification, the phrase "data attributed to a biological sample from an individual" is intended to mean that the data in some form derived from, or were generated using, the biological sample of the individual. The data may have been reformatted, revised, or mathematically altered to some degree after having been generated, such as by conversion from units in one measurement system to units in another measurement system; but, the data are understood to have been derived from, or were generated using, the biological sample.

"Target", "target molecule", and "analyte" are used interchangeably herein to refer to any molecule of interest that may be present in a biological sample. A "molecule of interest" includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule", "target", or "analyte" refers to a set of copies of one type or species of molecule or multi-molecular structure. "Target molecules", "targets", and "analytes" refer to more than one type or species of molecule or multi-molecular structure. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing. In some embodiments, a target molecule is a protein, in which case the target molecule may be referred to as a "target protein."

As used herein, a "capture agent' or "capture reagent" refers to a molecule that is capable of binding specifically to a biomarker. A "target protein capture reagent" refers to a molecule that is capable of binding specifically to a target protein. Nonlimiting exemplary capture reagents include aptamers, antibodies, adnectins, ankyrins, other antibody mimetics and other protein scaffolds, autoantibodies, chimeras, small molecules, nucleic acids, lectins, ligand-binding receptors, imprinted polymers, avimers, peptidomimetics, hormone receptors, cytokine receptors, synthetic receptors, and modifications and fragments of any of the aforementioned capture reagents. In some embodiments, a capture reagent is selected from an aptamer and an antibody.

The term "antibody" refers to full-length antibodies of any species and fragments and derivatives of such antibodies, including Fab fragments, F(ab')2 fragments, single chain antibodies, Fv fragments, and single chain Fv fragments. The term "antibody" also refers to synthetically-derived antibodies, such as phage display-derived antibodies and fragments, affybodies, nanobodies, etc.

As used herein, "marker" and "biomarker" are used interchangeably to refer to a target molecule that indicates or is a sign of a normal or abnormal process in an individual or of a disease or other condition in an individual. More specifically, a "marker" or "biomarker" is an anatomic, physiologic, biochemical, or molecular parameter associated with the presence of a specific physiological state or process, whether normal or abnormal, and, if abnormal, whether chronic or acute. Biomarkers are detectable and measurable by a variety of methods including laboratory assays and medical imaging. In some embodiments, a biomarker is a target protein.

As used herein, "biomarker level" and "level" refer to a measurement that is made using any analytical method for detecting the biomarker in a biological sample and that indicates the presence, absence, absolute amount or concentration, relative amount or concentration, titer, a level, an expression level, a ratio of measured levels, or the like, of, for, or corresponding to the biomarker in the biological sample. The exact nature of the "level" depends on the specific design and components of the particular analytical method employed to detect the biomarker.

When a biomarker indicates or is a sign of an abnormal process or a disease or other condition in an individual, that biomarker is generally described as being either over-expressed or under-expressed as compared to an expression level or value of the biomarker that indicates or is a sign of a normal process or an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

A "control level" of a target molecule refers to the level of the target molecule in the same sample type from an individual that does not have the disease or condition, or from an individual that is not suspected or at risk of having the disease or condition, or from an individual that has had a primary or first cardiovascular event but not a secondary cardiovascular event, or from an individual that has stable cardiovascular disease. Control level may refer to the average level of the target molecule in samples from a population of individuals that does not have the disease or condition, or that is not suspected or at risk of having the disease or condition, or that has had a primary or first cardiovascular event but not a secondary cardiovascular event, or that has stable cardiovascular disease or a combination thereof.

As used herein, "individual," "subject," and "patient" are used interchangeably to refer to a mammal. A mammalian individual can be a human or non-human. In various embodiments, the individual is a human. A healthy or normal individual is an individual in which the disease or condition of interest (including, for example, Cardiovascular Events such as myocardial infarction, stroke and congestive heart failure) is not detectable by conventional diagnostic methods.

"Diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (i.e., a diagnosis of the absence of a disease or condition) or diagnosed as ill/abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual. The prediction of risk of a CV event includes distinguishing individuals who have an increased risk of a CV event from individuals who do not.

"Prognose", "prognosing", "prognosis", and variations thereof refer to the prediction of a future course of a disease or condition in an individual who has the disease or condition (e.g., predicting patient survival), and such terms encompass the evaluation of disease or condition response after the administration of a treatment or therapy to the individual.

"Evaluate", "evaluating", "evaluation", and variations thereof encompass both "diagnose" and "prognose" and also encompass determinations or predictions about the future course of a disease or condition in an individual who does not have the disease as well as determinations or predictions regarding the risk that a disease or condition will recur in an individual who apparently has been cured of the disease or has had the condition resolved. The term "evaluate" also encompasses assessing an individual's response to a therapy, such as, for example, predicting whether an individual is likely to respond favorably to a therapeutic agent or is unlikely to respond to a therapeutic agent (or will experience toxic or other undesirable side effects, for example), selecting a therapeutic agent for administration to an individual, or monitoring or determining an individual's response to a therapy that has been administered to the individual. Thus, "evaluating" risk of a CV event can include, for example, any of the following: predicting the future risk of a CV event in an individual; predicting the risk of a CV event in an individual who apparently has no CV issues; predicting a particular type of CV event; predicting the time to a CV event; or determining or predicting an individual's response to a CV treatment or selecting a CV treatment to administer to an individual based upon a determination of the biomarker values derived from the individual's biological sample. Evaluation of risk of a CV event can include embodiments such as the assessment of risk of a CV event on a continuous scale, or classification of risk of a CV event in escalating classifications. Classification of risk includes, for example, classification into two or more classifications such as "No Elevated Risk of a CV Event;" "Elevated Risk of a CV Event;" and/or "Below Average Risk of CV Event." In some embodiments, the evaluation of risk of a CV event is for a defined period. Nonlimiting exemplary defined periods include 1 year, 2 years, 3 years, 4 years, 5 years and more than 5 years.

As used herein, "additional biomedical information" refers to one or more evaluations of an individual, other than using any of the biomarkers described herein, that are associated with CV risk or, more specifically, CV event risk. "Additional biomedical information" includes any of the following: physical descriptors of an individual, including the height and/or weight of an individual; the age of an individual; the gender of an individual; change in weight; the ethnicity of an individual; occupational history; family history of cardiovascular disease (or other circulatory system disorders); the presence of a genetic marker(s) correlating with a higher risk of cardiovascular disease (or other circulatory system disorders) in the individual or a family member alterations in the carotid intima thickness; clinical symptoms such as chest pain, weight gain or loss gene expression values; physical descriptors of an individual, including physical descriptors observed by radiologic imaging; smoking status; alcohol use history; occupational history; dietary habits—salt, saturated fat and cholesterol intake; caffeine consumption; and imaging information such as electrocardiogram, echocardiography, carotid ultrasound for intima-media thickness, flow mediated dilation, pulse wave velocity, ankle-brachial index, stress echocardiography, myocardial perfusion imaging, coronary calcium by CT, high resolution CT angiography, MRI imaging, and other imaging modalities; and the individual's medications. Testing of biomarker levels in combination with an evaluation of any additional biomedical information, including other laboratory tests (e.g., HDL, LDL testing, CRP levels, Nt-proBNP testing, BNP testing, high sensitivity troponin testing, galectin-3 testing, serum albumin testing, creatine testing), may, for example, improve sensitivity, specificity, and/or AUC for prediction of CV events as compared to biomarker testing alone or evaluating any particular item of additional biomedical information alone (e.g., carotid intima thickness imaging alone). Additional biomedical information can be obtained from an individual using routine techniques known in the art, such as from the individual themselves by use of a routine patient questionnaire or health history questionnaire, etc., or from a medical practitioner, etc. Testing of biomarker levels in combination with an evaluation of any additional biomedical information may, for example, improve sensitivity, specificity, and/or thresholds for prediction of CV events (or other cardiovascular-related uses) as compared to biomarker testing alone or evaluating any particular item of additional biomedical information alone (e.g., CT imaging alone).

As used herein, "detecting" or "determining" with respect to a biomarker value includes the use of both the instrument used to observe and record a signal corresponding to a biomarker level and the material/s required to generate that signal. In various embodiments, the biomarker level is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like.

As used herein, an "American College of Cardiology (ACC) risk score" is determined according to Goff et al., "2013 ACC/AHA Guideline on the Assessment of Cardiovascular Risk: A Report of the American College of Cardiology/American Heart Association Task Force on Practice Guidelines," published online in *Circulation* on Nov. 12, 2013 (Print ISSN: 0009-7322, Online ISSN: 1524-4539). As used herein, a "high" risk score is a 20.0% or greater predicted 10-year risk for a hard atherosclerotic/cardiovascular disease (ASCVD) event (defined as first occurrence of nonfatal myocardial infarction or coronary heart disease (CHD) death, or fatal or nonfatal stroke); an "intermediate" risk score is a 10.0-19.9% predicted 10-year risk for a hard ASCVD event; and a "low" risk score is a <10.0% predicted 10-year risk for a hard ASCVD event. See Goff at page 16, Table 5.

"Solid support" refers herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate, and polymethylpentene. Suitable solid support particles that can be used include, e.g., encoded particles, such as Luminex®-type encoded particles, magnetic particles, and glass particles.

Exemplary Uses of Biomarkers

In various exemplary embodiments, methods are provided for evaluating risk of a CV event in an individual by detecting one or more biomarker values corresponding to one or more biomarkers that are present in the circulation of an individual, such as in serum or plasma, by any number of analytical methods, including any of the analytical methods described herein. These biomarkers are, for example, differentially expressed in individuals with increased risk of a CV event as compared to individuals without increased risk of a CV event. Detection of the differential expression of a biomarker in an individual can be used, for example, to permit the prediction of risk of a CV event within a 1 year, 2 year, 3 year, 4 year, or 5 year time frame.

In addition to testing biomarker levels as a stand-alone diagnostic test, biomarker levels can also be done in conjunction with determination of single nucleotide polymorphisms (SNPs) or other genetic lesions or variability that are indicative of increased risk of susceptibility of disease or condition. (See, e.g., Amos et al., Nature Genetics 40, 616-622 (2009)).

In addition to testing biomarker levels as a stand-alone diagnostic test, biomarker levels can also be used in conjunction with radiologic screening. Biomarker levels can also be used in conjunction with relevant symptoms or genetic testing. Detection of any of the biomarkers described herein may be useful after the risk of CV event has been evaluated to guide appropriate clinical care of the individual, including increasing to more aggressive levels of care in high risk individuals after the CV event risk has been determined. In addition to testing biomarker levels in conjunction with relevant symptoms or risk factors, information regarding the biomarkers can also be evaluated in conjunction with other types of data, particularly data that indicates an individual's risk for cardiovascular events (e.g., patient clinical history, symptoms, family history of cardiovascular disease, history of smoking or alcohol use, risk factors such as the presence of a genetic marker(s), and/or status of other biomarkers, etc.). These various data can be assessed by automated methods, such as a computer program/software, which can be embodied in a computer or other apparatus/device.

In addition to testing biomarker levels in conjunction with radiologic screening in high risk individuals (e.g., assessing biomarker levels in conjunction with blockage detected in a coronary angiogram), information regarding the biomarkers can also be evaluated in conjunction with other types of data, particularly data that indicates an individual's risk for having a CV event (e.g., patient clinical history, symptoms, family history of cardiovascular disease, risk factors such as whether or not the individual is a smoker, heavy alcohol user and/or status of other biomarkers, etc.). These various data can be assessed by automated methods, such as a computer program/software, which can be embodied in a computer or other apparatus/device.

Testing of biomarkers can also be associated with guidelines and cardiovascular risk algorithms currently in use in clinical practice. For example, the Framingham Risk Score uses risk factors to provide a risk score, such risk factors including LDL-cholesterol and HDL-cholesterol levels, impaired glucose levels, smoking, systolic blood pressure, and diabetes. The frequency of high-risk patients increases with age, and men comprise a greater proportion of high-risk patients than women.

Any of the described biomarkers may also be used in imaging tests. For example, an imaging agent can be coupled to any of the described biomarkers, which can be used to aid in prediction of risk of a Cardiovascular Event, to monitor response to therapeutic interventions, to select for target populations in a clinical trial among other uses.

Detection and Determination of Biomarkers and Biomarker Levels

A biomarker level for the biomarkers described herein can be detected using any of a variety of known analytical methods. In one embodiment, a biomarker value is detected using a capture reagent. In various embodiments, the capture reagent can be exposed to the biomarker in solution or can be exposed to the biomarker while the capture reagent is immobilized on a solid support. In other embodiments, the capture reagent contains a feature that is reactive with a secondary feature on a solid support. In these embodiments, the capture reagent can be exposed to the biomarker in solution, and then the feature on the capture reagent can be used in conjunction with the secondary feature on the solid support to immobilize the biomarker on the solid support. The capture reagent is selected based on the type of analysis to be conducted. Capture reagents include but are not limited to aptamers, antibodies, adnectins, ankyrins, other antibody mimetics and other protein scaffolds, autoantibodies, chimeras, small molecules, F(ab')2 fragments, single chain antibody fragments, Fv fragments, single chain Fv fragments, nucleic acids, lectins, ligand-binding receptors, affybodies, nanobodies, imprinted polymers, avimers, peptidomimetics, hormone receptors, cytokine receptors, and synthetic receptors, and modifications and fragments of these.

In some embodiments, a biomarker level is detected using a biomarker/capture reagent complex.

In some embodiments, the biomarker level is derived from the biomarker/capture reagent complex and is detected indirectly, such as, for example, as a result of a reaction that is subsequent to the biomarker/capture reagent interaction, but is dependent on the formation of the biomarker/capture reagent complex.

In some embodiments, the biomarker level is detected directly from the biomarker in a biological sample.

In some embodiments, biomarkers are detected using a multiplexed format that allows for the simultaneous detection of two or more biomarkers in a biological sample. In some embodiments of the multiplexed format, capture reagents are immobilized, directly or indirectly, covalently or non-covalently, in discrete locations on a solid support. In some embodiments, a multiplexed format uses discrete solid supports where each solid support has a unique capture reagent associated with that solid support, such as, for example quantum dots. In some embodiments, an individual device is used for the detection of each one of multiple biomarkers to be detected in a biological sample. Individual devices can be configured to permit each biomarker in the biological sample to be processed simultaneously. For example, a microtiter plate can be used such that each well in the plate is used to uniquely analyze one or more biomarkers to be detected in a biological sample.

In one or more of the foregoing embodiments, a fluorescent tag can be used to label a component of the biomarker/capture reagent complex to enable the detection of the biomarker level. In various embodiments, the fluorescent label can be conjugated to a capture reagent specific to any of the biomarkers described herein using known techniques, and the fluorescent label can then be used to detect the corresponding biomarker level. Suitable fluorescent labels include rare earth chelates, fluorescein and its derivatives, rhodamine and its derivatives, dansyl, allophycocyanin, PBXL-3, Qdot 605, Lissamine, phycoerythrin, Texas Red, and other such compounds.

In some embodiments, the fluorescent label is a fluorescent dye molecule. In some embodiments, the fluorescent dye molecule includes at least one substituted indolium ring system in which the substituent on the 3-carbon of the indolium ring contains a chemically reactive group or a conjugated substance. In some embodiments, the dye molecule includes an AlexFluor molecule, such as, for example, AlexaFluor 488, AlexaFluor 532, AlexaFluor 647, AlexaFluor 680, or AlexaFluor 700. In other embodiments, the dye molecule includes a first type and a second type of dye molecule, such as, e.g., two different AlexaFluor molecules. In some embodiments, the dye molecule includes a first type and a second type of dye molecule, and the two dye molecules have different emission spectra.

Fluorescence can be measured with a variety of instrumentation compatible with a wide range of assay formats. For example, spectrofluorimeters have been designed to analyze microtiter plates, microscope slides, printed arrays, cuvettes, etc. See Principles of Fluorescence Spectroscopy, by J. R. Lakowicz, Springer Science+Business Media, Inc., 2004. See Bioluminescence & Chemiluminescence: Progress & Current Applications; Philip E. Stanley and Larry J. Kricka editors, World Scientific Publishing Company, January 2002.

In one or more embodiments, a chemiluminescence tag can optionally be used to label a component of the biomarker/capture complex to enable the detection of a biomarker level. Suitable chemiluminescent materials include any of oxalyl chloride, Rodamin 6G, Ru(bipy)$_3^{2+}$, TMAE (tetrakis(dimethylamino)ethylene), Pyrogallol (1,2,3-trihydroxibenzene), Lucigenin, peroxyoxalates, Aryl oxalates, Acridinium esters, dioxetanes, and others.

In some embodiments, the detection method includes an enzyme/substrate combination that generates a detectable signal that corresponds to the biomarker level. Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like.

In some embodiments, the detection method can be a combination of fluorescence, chemiluminescence, radionuclide or enzyme/substrate combinations that generate a measurable signal. In some embodiments, multimodal signaling could have unique and advantageous characteristics in biomarker assay formats.

In some embodiments, the biomarker levels for the biomarkers described herein can be detected using any analytical methods including, singleplex aptamer assays, multiplexed aptamer assays, singleplex or multiplexed immunoassays, mRNA expression profiling, miRNA expression profiling, mass spectrometric analysis, histological/cytological methods, etc. as discussed below.

Determination of Biomarker Levels Using Aptamer-Based Assays

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands"; see also, e.g., U.S. Pat. Nos. 6,242,246, 6,458,543, and 6,503,715, each of which is entitled "Nucleic Acid Ligand Diagnostic Biochip". Once the microarray is contacted with a sample, the aptamers bind to their respective target molecules present in the sample and thereby enable a determination of a biomarker level corresponding to a biomarker.

As used herein, an "aptamer" refers to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Any of the aptamer methods disclosed herein can include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers can have either the same tag or a different tag.

An aptamer can be identified using any known method, including the SELEX process. Once identified, an aptamer can be prepared or synthesized in accordance with any known method, including chemical synthetic methods and enzymatic synthetic methods.

The terms "SELEX" and "SELEX process" are used interchangeably herein to refer generally to a combination of (1) the selection of aptamers that interact with a target molecule in a desirable manner, for example binding with high affinity to a protein, with (2) the amplification of those selected nucleic acids. The SELEX process can be used to identify aptamers with high affinity to a specific target or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH2), 2'-fluoro (2'-F), and/or 2'-O-methyl (2'-OMe). See also, U.S. Patent Application Publication 20090098549, entitled "SELEX and PHOTOSELEX", which describes nucleic acid libraries having expanded physical and chemical properties and their use in SELEX and photoSELEX.

Figure 14:
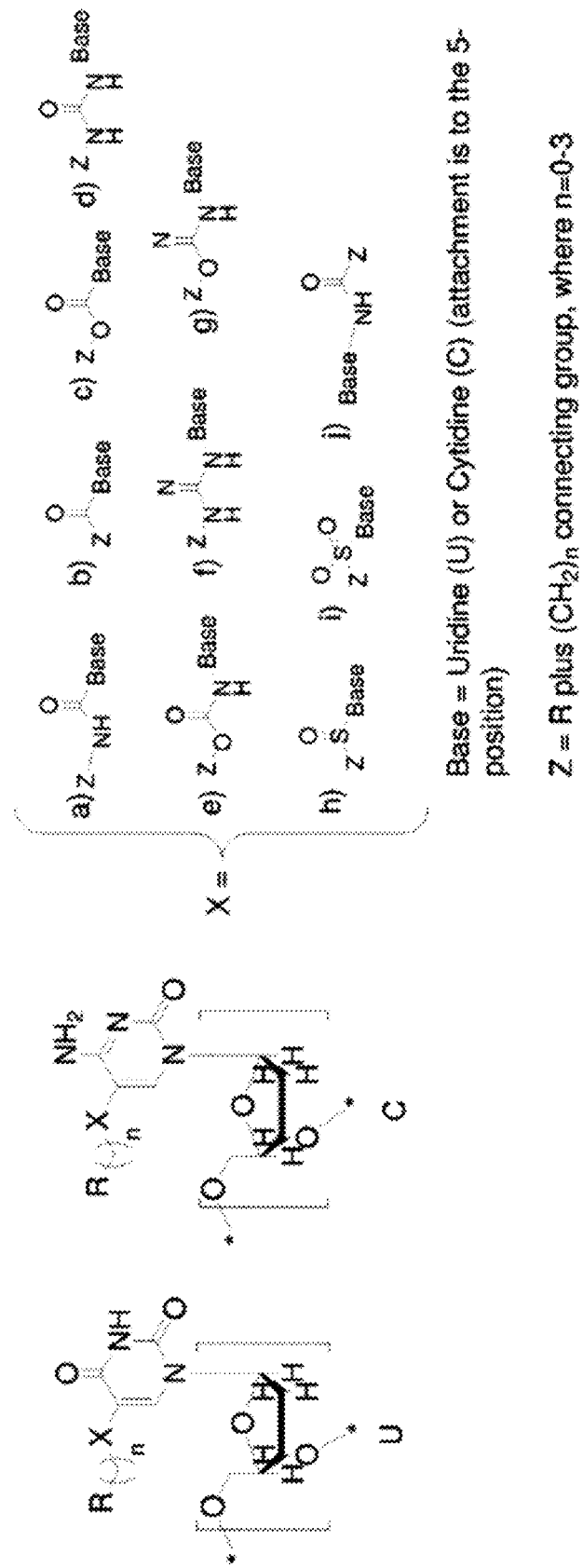
FIG. 14 shows certain exemplary modified pyrimidines that may be incorporated into aptamers, such as slow off-rate aptamers.
Figure 14:
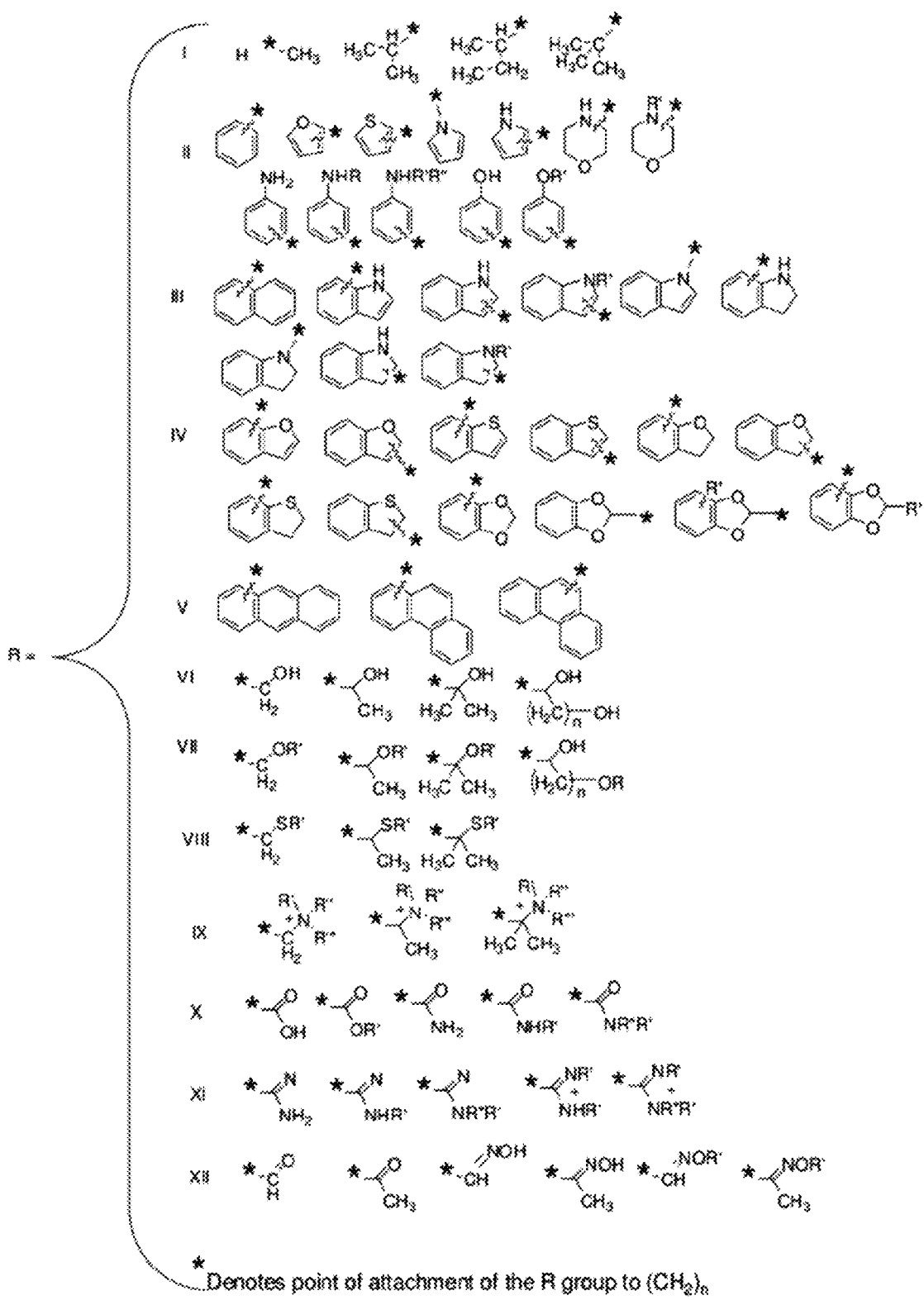

SELEX can also be used to identify aptamers that have desirable off-rate characteristics. See U.S. Publication No. 20090004667, entitled "Method for Generating Aptamers with Improved Off-Rates", which describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers with improved off-rate performance. Nonlimiting exemplary modified nucleotides include, for example, the modified pyrimidines shown in FIG. 14. In some embodiments, an aptamer comprises at least one nucleotide with a modification, such as a base modification. In some embodiments, an aptamer comprises at least one nucleotide with a hydrophobic modification, such as a hydrophobic base modification, allowing for hydrophobic contacts with a target protein. Such hydrophobic contacts, in some embodiments, contribute to greater affinity and/or slower off-rate binding by the aptamer. Nonlimiting exemplary nucleotides with hydrophobic modifications are shown in FIG. 14. In some embodiments, an aptamer comprises at least two, at least three, at least four, at least five, at least six, at least seven, at least eight, at least nine, or at least 10 nucleotides with hydrophobic modifications, where each hydrophobic modification may be the same or different from the others. In some embodiments, at least one, at least two, at least three, at least four, at least five, at least six, at least seven, at least eight, at least nine, or at least 10 hydrophobic modifications in an aptamer may be independently selected from the hydrophobic modifications shown in FIG. 14.

In some embodiments, a slow off-rate aptamer (including an aptamers comprising at least one nucleotide with a hydrophobic modification) has an off-rate (t½) of ≥30 minutes, ≥60 minutes, ≥90 minutes, ≥120 minutes, ≥150 minutes, ≥180 minutes, ≥210 minutes, or ≥240 minutes.

In some embodiments, an assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers. In this manner, the assay enables the detection of a biomarker level corresponding to a biomarker in the test sample.

In some assay formats, the aptamers are immobilized on the solid support prior to being contacted with the sample. Under certain circumstances, however, immobilization of the aptamers prior to contact with the sample may not provide an optimal assay. For example, pre-immobilization of the aptamers may result in inefficient mixing of the aptamers with the target molecules on the surface of the solid support, perhaps leading to lengthy reaction times and, therefore, extended incubation periods to permit efficient binding of the aptamers to their target molecules. Further, when photoaptamers are employed in the assay and depending upon the material utilized as a solid support, the solid support may tend to scatter or absorb the light used to effect the formation of covalent bonds between the photoaptamers and their target molecules. Moreover, depending upon the method employed, detection of target molecules bound to their aptamers can be subject to imprecision, since the surface of the solid support may also be exposed to and affected by any labeling agents that are used. Finally, immobilization of the aptamers on the solid support generally involves an aptamer-preparation step (i.e., the immobilization) prior to exposure of the aptamers to the sample, and this preparation step may affect the activity or functionality of the aptamers.

Aptamer assays that permit an aptamer to capture its target in solution and then employ separation steps that are designed to remove specific components of the aptamer-target mixture prior to detection have also been described (see U.S. Publication No. 20090042206, entitled "Multi-plexed Analyses of Test Samples"). The described aptamer assay methods enable the detection and quantification of a non-nucleic acid target (e.g., a protein target) in a test sample by detecting and quantifying a nucleic acid (i.e., an aptamer). The described methods create a nucleic acid surrogate (i.e, the aptamer) for detecting and quantifying a non-nucleic acid target, thus allowing the wide variety of nucleic acid technologies, including amplification, to be applied to a broader range of desired targets, including protein targets.

Aptamers can be constructed to facilitate the separation of the assay components from an aptamer biomarker complex (or photoaptamer biomarker covalent complex) and permit isolation of the aptamer for detection and/or quantification. In one embodiment, these constructs can include a cleavable or releasable element within the aptamer sequence. In other embodiments, additional functionality can be introduced into the aptamer, for example, a labeled or detectable component, a spacer component, or a specific binding tag or immobilization element. For example, the aptamer can include a tag connected to the aptamer via a cleavable moiety, a label, a spacer component separating the label, and the cleavable moiety. In one embodiment, a cleavable element is a photocleavable linker. The photocleavable linker can be attached to a biotin moiety and a spacer section, can include an NHS group for derivatization of amines, and can be used to introduce a biotin group to an aptamer, thereby allowing for the release of the aptamer later in an assay method.

Homogenous assays, done with all assay components in solution, do not require separation of sample and reagents prior to the detection of signal. These methods are rapid and easy to use. These methods generate signal based on a molecular capture or binding reagent that reacts with its specific target. In some embodiments of the methods described herein, the molecular capture reagents comprise an aptamer or an antibody or the like and the specific target may be a biomarker shown in Table 3.

In some embodiments, a method for signal generation takes advantage of anisotropy signal change due to the interaction of a fluorophore-labeled capture reagent with its specific biomarker target. When the labeled capture reacts with its target, the increased molecular weight causes the rotational motion of the fluorophore attached to the complex to become much slower changing the anisotropy value. By monitoring the anisotropy change, binding events may be used to quantitatively measure the biomarkers in solutions. Other methods include fluorescence polarization assays, molecular beacon methods, time resolved fluorescence quenching, chemiluminescence, fluorescence resonance energy transfer, and the like.

An exemplary solution-based aptamer assay that can be used to detect a biomarker level in a biological sample includes the following: (a) preparing a mixture by contacting the biological sample with an aptamer that includes a first tag and has a specific affinity for the biomarker, wherein an aptamer affinity complex is formed when the biomarker is present in the sample; (b) exposing the mixture to a first solid support including a first capture element, and allowing the first tag to associate with the first capture element; (c) removing any components of the mixture not associated with the first solid support; (d) attaching a second tag to the biomarker component of the aptamer affinity complex; (e) releasing the aptamer affinity complex from the first solid support; (f) exposing the released aptamer affinity complex to a second solid support that includes a second capture element and allowing the second tag to associate with the second capture element; (g) removing any non-complexed aptamer from the mixture by partitioning the non-complexed aptamer from the aptamer affinity complex; (h) eluting the aptamer from the solid support; and (i) detecting the biomarker by detecting the aptamer component of the aptamer affinity complex.

Any means known in the art can be used to detect a biomarker value by detecting the aptamer component of an aptamer affinity complex. A number of different detection methods can be used to detect the aptamer component of an affinity complex, such as, for example, hybridization assays, mass spectroscopy, or QPCR. In some embodiments, nucleic acid sequencing methods can be used to detect the aptamer component of an aptamer affinity complex and thereby detect a biomarker value. Briefly, a test sample can be subjected to any kind of nucleic acid sequencing method to identify and quantify the sequence or sequences of one or more aptamers present in the test sample. In some embodiments, the sequence includes the entire aptamer molecule or any portion of the molecule that may be used to uniquely identify the molecule. In other embodiments, the identifying sequencing is a specific sequence added to the aptamer; such sequences are often referred to as "tags," "barcodes," or "zipcodes." In some embodiments, the sequencing method includes enzymatic steps to amplify the aptamer sequence or to convert any kind of nucleic acid, including RNA and DNA that contain chemical modifications to any position, to any other kind of nucleic acid appropriate for sequencing.

In some embodiments, the sequencing method includes one or more cloning steps. In other embodiments the sequencing method includes a direct sequencing method without cloning.

In some embodiments, the sequencing method includes a directed approach with specific primers that target one or more aptamers in the test sample. In other embodiments, the sequencing method includes a shotgun approach that targets all aptamers in the test sample.

In some embodiments, the sequencing method includes enzymatic steps to amplify the molecule targeted for sequencing. In other embodiments, the sequencing method directly sequences single molecules. An exemplary nucleic acid sequencing-based method that can be used to detect a biomarker value corresponding to a biomarker in a biological sample includes the following: (a) converting a mixture of aptamers that contain chemically modified nucleotides to unmodified nucleic acids with an enzymatic step; (b) shotgun sequencing the resulting unmodified nucleic acids with a massively parallel sequencing platform such as, for example, the 454 Sequencing System (454 Life Sciences/Roche), the Illumina Sequencing System (Illumina), the ABI SOLiD Sequencing System (Applied Biosystems), the HeliScope Single Molecule Sequencer (Helicos Biosciences), or the Pacific Biosciences Real Time Single-Molecule Sequencing System (Pacific BioSciences) or the Polonator G Sequencing System (Dover Systems); and (c) identifying and quantifying the aptamers present in the mixture by specific sequence and sequence count.

A nonlimiting exemplary method of detecting biomarkers in a biological sample using aptamers is described in Example 1. See also Kraemer et al., 2011, *PLoS One* 6(10): e26332.

Determination of Biomarker Levels Using Immunoassays

Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies and fragments thereof are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results are generated through the use of a standard curve created with known concentrations of the specific analyte to be detected. The response or signal from an unknown sample is plotted onto the standard curve, and a quantity or level corresponding to the target in the unknown sample is established.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes (I') or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or for quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 386 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Determination of Biomarker Levels Using Gene Expression Profiling

Measuring mRNA in a biological sample may, in some embodiments, be used as a surrogate for detection of the level of the corresponding protein in the biological sample. Thus, in some embodiments, a biomarker or biomarker panel described herein can be detected by detecting the appropriate RNA.

In some embodiments, mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

Detection of Biomarkers Using In Vivo Molecular Imaging Technologies

In some embodiments, a biomarker described herein may be used in molecular imaging tests. For example, an imaging agent can be coupled to a capture reagent, which can be used to detect the biomarker in vivo.

In vivo imaging technologies provide non-invasive methods for determining the state of a particular disease in the body of an individual. For example, entire portions of the body, or even the entire body, may be viewed as a three dimensional image, thereby providing valuable information concerning morphology and structures in the body. Such technologies may be combined with the detection of the biomarkers described herein to provide information concerning the biomarker in vivo.

The use of in vivo molecular imaging technologies is expanding due to various advances in technology. These advances include the development of new contrast agents or labels, such as radiolabels and/or fluorescent labels, which can provide strong signals within the body; and the development of powerful new imaging technology, which can detect and analyze these signals from outside the body, with sufficient sensitivity and accuracy to provide useful information. The contrast agent can be visualized in an appropriate imaging system, thereby providing an image of the portion or portions of the body in which the contrast agent is located. The contrast agent may be bound to or associated with a capture reagent, such as an aptamer or an antibody, for example, and/or with a peptide or protein, or an oligonucleotide (for example, for the detection of gene expression), or a complex containing any of these with one or more macromolecules and/or other particulate forms.

The contrast agent may also feature a radioactive atom that is useful in imaging. Suitable radioactive atoms include technetium-99m or iodine-123 for scintigraphic studies. Other readily detectable moieties include, for example, spin labels for magnetic resonance imaging (MRI) such as, for example, iodine-123 again, iodine-131, indium-111, fluorine-19, carbon-13, nitrogen-15, oxygen-17, gadolinium, manganese or iron. Such labels are well known in the art and could easily be selected by one of ordinary skill in the art.

Standard imaging techniques include but are not limited to magnetic resonance imaging, computed tomography scanning, positron emission tomography (PET), single photon emission computed tomography (SPECT), and the like. For diagnostic in vivo imaging, the type of detection instrument available is a major factor in selecting a given contrast agent, such as a given radionuclide and the particular biomarker that it is used to target (protein, mRNA, and the like). The radionuclide chosen typically has a type of decay that is detectable by a given type of instrument. Also, when selecting a radionuclide for in vivo diagnosis, its half-life should be long enough to enable detection at the time of maximum uptake by the target tissue but short enough that deleterious radiation of the host is minimized.

Exemplary imaging techniques include but are not limited to PET and SPECT, which are imaging techniques in which a radionuclide is synthetically or locally administered to an individual. The subsequent uptake of the radiotracer is measured over time and used to obtain information about the targeted tissue and the biomarker. Because of the high-energy (gamma-ray) emissions of the specific isotopes employed and the sensitivity and sophistication of the instruments used to detect them, the two-dimensional distribution of radioactivity may be inferred from outside of the body.

Commonly used positron-emitting nuclides in PET include, for example, carbon-11, nitrogen-13, oxygen-15, and fluorine-18. Isotopes that decay by electron capture and/or gamma-emission are used in SPECT and include, for example iodine-123 and technetium-99m. An exemplary method for labeling amino acids with technetium-99m is the reduction of pertechnetate ion in the presence of a chelating precursor to form the labile technetium-99m-precursor complex, which, in turn, reacts with the metal binding group of a bifunctionally modified chemotactic peptide to form a technetium-99m-chemotactic peptide conjugate.

Antibodies are frequently used for such in vivo imaging diagnostic methods. The preparation and use of antibodies for in vivo diagnosis is well known in the art. Similarly, aptamers may be used for such in vivo imaging diagnostic methods. For example, an aptamer that was used to identify a particular biomarker described herein may be appropriately labeled and injected into an individual to detect the biomarker in vivo. The label used will be selected in accordance with the imaging modality to be used, as previously described. Aptamer-directed imaging agents could have unique and advantageous characteristics relating to tissue penetration, tissue distribution, kinetics, elimination, potency, and selectivity as compared to other imaging agents.

Such techniques may also optionally be performed with labeled oligonucleotides, for example, for detection of gene expression through imaging with antisense oligonucleotides. These methods are used for in situ hybridization, for example, with fluorescent molecules or radionuclides as the label. Other methods for detection of gene expression include, for example, detection of the activity of a reporter gene.

Another general type of imaging technology is optical imaging, in which fluorescent signals within the subject are detected by an optical device that is external to the subject. These signals may be due to actual fluorescence and/or to bioluminescence. Improvements in the sensitivity of optical detection devices have increased the usefulness of optical imaging for in vivo diagnostic assays.

For a review of other techniques, see N. Blow, Nature Methods, 6, 465-469, 2009.

Determination of Biomarker Levels Using Mass Spectrometry Methods

A variety of configurations of mass spectrometers can be used to detect biomarker levels. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al. Anal. Chem. 70:647 R-716R (1998); Kinter and Sherman, New York (2000)).

Protein biomarkers and biomarker levels can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS)N, atmospheric pressure photoionization mass spectrometry (APPI-MS), APPI-MS/MS, and APPI-(MS)N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker levels. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

Determination of Biomarker Levels Using a Proximity Ligation Assay

A proximity ligation assay can be used to determine biomarker values. Briefly, a test sample is contacted with a pair of affinity probes that may be a pair of antibodies or a pair of aptamers, with each member of the pair extended with an oligonucleotide. The targets for the pair of affinity probes may be two distinct determinates on one protein or one determinate on each of two different proteins, which may exist as homo- or hetero-multimeric complexes. When probes bind to the target determinates, the free ends of the oligonucleotide extensions are brought into sufficiently close proximity to hybridize together. The hybridization of the oligonucleotide extensions is facilitated by a common connector oligonucleotide which serves to bridge together the oligonucleotide extensions when they are positioned in sufficient proximity. Once the oligonucleotide extensions of the probes are hybridized, the ends of the extensions are joined together by enzymatic DNA ligation.

Each oligonucleotide extension comprises a primer site for PCR amplification. Once the oligonucleotide extensions are ligated together, the oligonucleotides form a continuous DNA sequence which, through PCR amplification, reveals information regarding the identity and amount of the target protein, as well as, information regarding protein-protein interactions where the target determinates are on two different proteins. Proximity ligation can provide a highly sensitive and specific assay for real-time protein concentration and interaction information through use of real-time PCR. Probes that do not bind the determinates of interest do not have the corresponding oligonucleotide extensions brought into proximity and no ligation or PCR amplification can proceed, resulting in no signal being produced.

The foregoing assays enable the detection of biomarker values that are useful in methods for prediction of risk of CV events, where the methods comprise detecting, in a biological sample from an individual, at least five, at least six, at least seven, at least eight, or all nine biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin, wherein a classification, as described below, using the biomarker values indicates whether the individual has elevated risk of a CV event occurring within a 1 year, 2 year, 3 year, or 4 year time period. In accordance with any of the methods described herein, biomarker values can be detected and classified individually or they can be detected and classified collectively, as for example in a multiplex assay format.

Classification of Biomarkers and Calculation of Disease Scores

In some embodiments, a biomarker "signature" for a given diagnostic test contains a set of biomarkers, each biomarker having characteristic levels in the populations of interest. Characteristic levels, in some embodiments, may refer to the mean or average of the biomarker levels for the individuals in a particular group. In some embodiments, a diagnostic method described herein can be used to assign an unknown sample from an individual into one of two groups, either at increased risk of a CV event or not.

The assignment of a sample into one of two or more groups is known as classification, and the procedure used to accomplish this assignment is known as a classifier or a classification method. Classification methods may also be referred to as scoring methods. There are many classification methods that can be used to construct a diagnostic classifier from a set of biomarker levels. In some instances, classification methods are performed using supervised learning techniques in which a data set is collected using samples obtained from individuals within two (or more, for multiple classification states) distinct groups one wishes to distinguish. Since the class (group or population) to which each sample belongs is known in advance for each sample, the classification method can be trained to give the desired classification response. It is also possible to use unsupervised learning techniques to produce a diagnostic classifier.

Common approaches for developing diagnostic classifiers include decision trees; bagging+boosting+forests; rule inference based learning; Parzen Windows; linear models; logistic; neural network methods; unsupervised clustering; K-means; hierarchical ascending/descending; semi-supervised learning; prototype methods; nearest neighbor; kernel density estimation; support vector machines; hidden Markov models; Boltzmann Learning; and classifiers may be combined either simply or in ways which minimize particular objective functions. For a review, see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009.

To produce a classifier using supervised learning techniques, a set of samples called training data are obtained. In the context of diagnostic tests, training data includes samples from the distinct groups (classes) to which unknown samples will later be assigned. For example, samples collected from individuals in a control population and individuals in a particular disease population can constitute training data to develop a classifier that can classify unknown samples (or, more particularly, the individuals from whom the samples were obtained) as either having the disease or being free from the disease. The development of the classifier from the training data is known as training the classifier. Specific details on classifier training depend on the nature of the supervised learning technique. Training a naïve Bayesian classifier is an example of such a supervised learning technique (see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009). Training of a naïve Bayesian classifier is described, e.g., in U.S. Publication Nos: 2012/0101002 and 2012/0077695.

Since typically there are many more potential biomarker levels than samples in a training set, care must be used to avoid over-fitting. Over-fitting occurs when a statistical model describes random error or noise instead of the underlying relationship. Over-fitting can be avoided in a variety of way, including, for example, by limiting the number of biomarkers used in developing the classifier, by assuming that the biomarker responses are independent of one another, by limiting the complexity of the underlying statistical model employed, and by ensuring that the underlying statistical model conforms to the data.

An illustrative example of the development of a diagnostic test using a set of biomarkers includes the application of a naïve Bayes classifier, a simple probabilistic classifier based on Bayes theorem with strict independent treatment of the biomarkers. Each biomarker is described by a class-dependent probability density function (pdf) for the measured RFU values or log RFU (relative fluorescence units) values in each class. The joint pdfs for the set of biomarkers in one class is assumed to be the product of the individual class-dependent pdfs for each biomarker. Training a naïve Bayes classifier in this context amounts to assigning parameters ("parameterization") to characterize the class dependent pdfs. Any underlying model for the class-dependent pdfs may be used, but the model should generally conform to the data observed in the training set.

The performance of the naïve Bayes classifier is dependent upon the number and quality of the biomarkers used to construct and train the classifier. A single biomarker will perform in accordance with its KS-distance (Kolmogorov-Smirnov). The addition of subsequent biomarkers with good KS distances (>0.3, for example) will, in general, improve the classification performance if the subsequently added biomarkers are independent of the first biomarker. Using the sensitivity plus specificity as a classifier score, many high scoring classifiers can be generated with a variation of a greedy algorithm. (A greedy algorithm is any algorithm that follows the problem solving metaheuristic of making the locally optimal choice at each stage with the hope of finding the global optimum.)

Another way to depict classifier performance is through a receiver operating characteristic (ROC), or simply ROC curve or ROC plot. The ROC is a graphical plot of the sensitivity, or true positive rate, vs. false positive rate (1—specificity or 1—true negative rate), for a binary classifier system as its discrimination threshold is varied. The ROC can also be represented equivalently by plotting the fraction of true positives out of the positives (TPR=true positive rate) vs. the fraction of false positives out of the negatives (FPR=false positive rate). Also known as a Relative Operating Characteristic curve, because it is a comparison of two operating characteristics (TPR & FPR) as the criterion changes. The area under the ROC curve (AUC) is commonly used as a summary measure of diagnostic accuracy. It can take values from 0.0 to 1.0. The AUC has an important statistical property: the AUC of a classifier is equivalent to the probability that the classifier will rank a randomly chosen positive instance higher than a randomly chosen negative instance (Fawcett T, 2006. An introduction to ROC analysis. Pattern Recognition Letters. 27: 861-874). This is equivalent to the Wilcoxon test of ranks (Hanley, J. A., McNeil, B. J., 1982. The meaning and use of the area under a receiver operating characteristic (ROC) curve. Radiology 143, 29-36.). Another way of describing performance of a diagnostic test in relation to a known reference standard is the net reclassification index: the ability of the new test to correctly upgrade or downgrade risk when compared with the reference standard test. See, e.g., Pencina et al., 2011, *Stat. Med.* 30: 11-21. While the AUC under the ROC curve is optimal for assessing performance of a 2-class classifier, stratified and personalized medicine relies upon the inference that the population contains more classes than 2. For such comparisons the hazard ratio of the upper vs. lower quartiles (or other stratifications such as deciles) can be used more appropriately.

The risk predictions enabled through this invention may be applied to individuals in primary care or in specialist cardiovascular centers, or even direct to the consumer. In some embodiments, the classifiers used to predict events may involve some calibration to the population to which they are applied—for example there may be variations due to ethnicity or geography. Such calibrations, in some embodiments, may be established in advance from large population studies, so when applied to an individual patient these are incorporated prior to making a risk prediction. A venous blood sample is taken, processed appropriately and analyzed as described herein. Once the analysis is complete, the risk predictions may be made mathematically, with or without incorporating other metadata from medical records described herein such as genetic or demographic. Various forms of output of information are possible depending on the level of expertise of the consumer. For consumers seeking the simplest type of output the information may be, in some embodiments, "is this person likely to have an event in the next x years (where x is 1-4), yes/no" or alternatively akin to a "traffic light" red/orange/green or its verbal or written equivalent such as high/medium/low risk. For consumers seeking greater detail, in some embodiments, the risk may be output as a number or a graphic illustrating the probability of an event per unit time as a continuous score, or a greater number of strata (such as deciles), and/or the average time to event and/or the most likely type of event. In some embodiments, the output may include therapeutic recommendations. Longitudinal monitoring of the same patient over time will enable graphics showing response to interventions or lifestyle changes. In some embodiments, more than one type of output may be provided at the same time to fulfill the needs of the patient and of individual members of the care team with differing levels of expertise.

In some embodiments, the nine biomarkers shown in Table 3 (the "CVD9 biomarkers") are detected in a blood sample (such as a plasma sample or a serum sample) from a subject, for example, using aptamers, such as slow off-rate aptamers. The log RFU values are used to calculate a prognostic index (PI). A nonlimiting exemplary PI formula is shown below:

PI=−16.61+1.55×ANGPT2−1.22×GDF11+2.12×C7−2.64×SERPINF2+0.57×CCL18+1.02×ANGPTL4+1.43×KLK3.SERPINA3+0.72×MMP12+0.59×TNNI3,$s$=0.85 where protein levels are taken to be in log 10 RFU. One of ordinary skill in the art will appreciate that the PI formula may be re-calibrated according to the population from which the subject is taken. Such recalibration may be carried out according to the methods described herein and/or methods known in the art.

Given the PI, the probability that the subject will suffer a cardiovascular event (CV event) in the next "t" years is given by the formula:

$$Pr[T \leq t] = 1 - e^{-e^{\left(\frac{Log(t)-PI}{s}\right)}},$$

where PI is the prognostic index (or linear predictor) and s is the associated scale parameter for the extreme value distribution. In various embodiments, "t" is 5 years or less, 4 years or less, 3 years or less, or 2 years or less.

Kits

Any combination of the biomarkers described herein can be detected using a suitable kit, such as for use in performing the methods disclosed herein. Furthermore, any kit can contain one or more detectable labels as described herein, such as a fluorescent moiety, etc.

In some embodiments, a kit includes (a) one or more capture reagents (such as, for example, at least one aptamer or antibody) for detecting one or more biomarkers in a biological sample, wherein the biomarkers include at least five, at least six, at least seven, at least eight, or all nine biomarkers selected from MMP12, angiopoietin-2, complement C7, cardiac troponin I, angiopoietin-related protein 4, CCL18/PARC, alpha-1-antichymotrypsin complex, GDF11 and alpha-2-antiplasmin, and optionally (b) one or more software or computer program products for classifying the individual from whom the biological sample was obtained as either having or not having increased risk of a CV event or for determining the likelihood that the individual has increased risk of a CV event, as further described herein. Alternatively, rather than one or more computer program products, one or more instructions for manually performing the above steps by a human can be provided.

In some embodiments, a kit comprises a solid support, a capture reagent, and a signal generating material. The kit can also include instructions for using the devices and reagents, handling the sample, and analyzing the data. Further the kit may be used with a computer system or software to analyze and report the result of the analysis of the biological sample.

The kits can also contain one or more reagents (e.g., solubilization buffers, detergents, washes, or buffers) for processing a biological sample. Any of the kits described herein can also include, e.g., buffers, blocking agents, mass spectrometry matrix materials, antibody capture agents, positive control samples, negative control samples, software and information such as protocols, guidance and reference data.

In some embodiments kits are provided for the analysis of CV event risk status, wherein the kits comprise PCR primers for one or more aptamers specific to biomarkers described herein. In some embodiments, a kit may further include instructions for use and correlation of the biomarkers with prediction of risk of a CV event. In some embodiments, a kit may also include a DNA array containing the complement of one or more of the aptamers specific for the biomarkers described herein, reagents, and/or enzymes for amplifying or isolating sample DNA. In some embodiments, kits may include reagents for real-time PCR, for example, TaqMan probes and/or primers, and enzymes.

For example, a kit can comprise (a) reagents comprising at least one capture reagent for determining the level of one or more biomarkers in a test sample, and optionally (b) one or more algorithms or computer programs for performing the steps of comparing the amount of each biomarker quantified in the test sample to one or more predetermined cutoffs. In some embodiments, an algorithm or computer program assigns a score for each biomarker quantified based on said comparison and, in some embodiments, combines the assigned scores for each biomarker quantified to obtain a total score. Further, in some embodiments, an algorithm or computer program compares the total score with a predetermined score, and uses the comparison to determine whether an individual has an increased risk of a CV event. Alternatively, rather than one or more algorithms or computer programs, one or more instructions for manually performing the above steps by a human can be provided.

Computer Methods and Software

Once a biomarker or biomarker panel is selected, a method for diagnosing an individual can comprise the following: 1) obtain a biological sample; 2) perform an analytical method to detect and measure the biomarker or biomarkers in the panel in the biological sample; 3) optionally perform any data normalization or standardization; 4) determine each biomarker level; and 5) report the results. In some embodiments, the results are calibrated to the population/ethnicity of the subject. In some embodiments, the biomarker levels are combined in some way and a single value for the combined biomarker levels is reported. In this approach, in some embodiments, the score may be a single number determined from the integration of all the biomarkers that is compared to a pre-set threshold value that is an indication of the presence or absence of disease. Or the diagnostic or predictive score may be a series of bars that each represent a biomarker value and the pattern of the responses may be compared to a pre-set pattern for determination of the presence or absence of disease, condition or the increased risk (or not) of an event.

Figure 12:
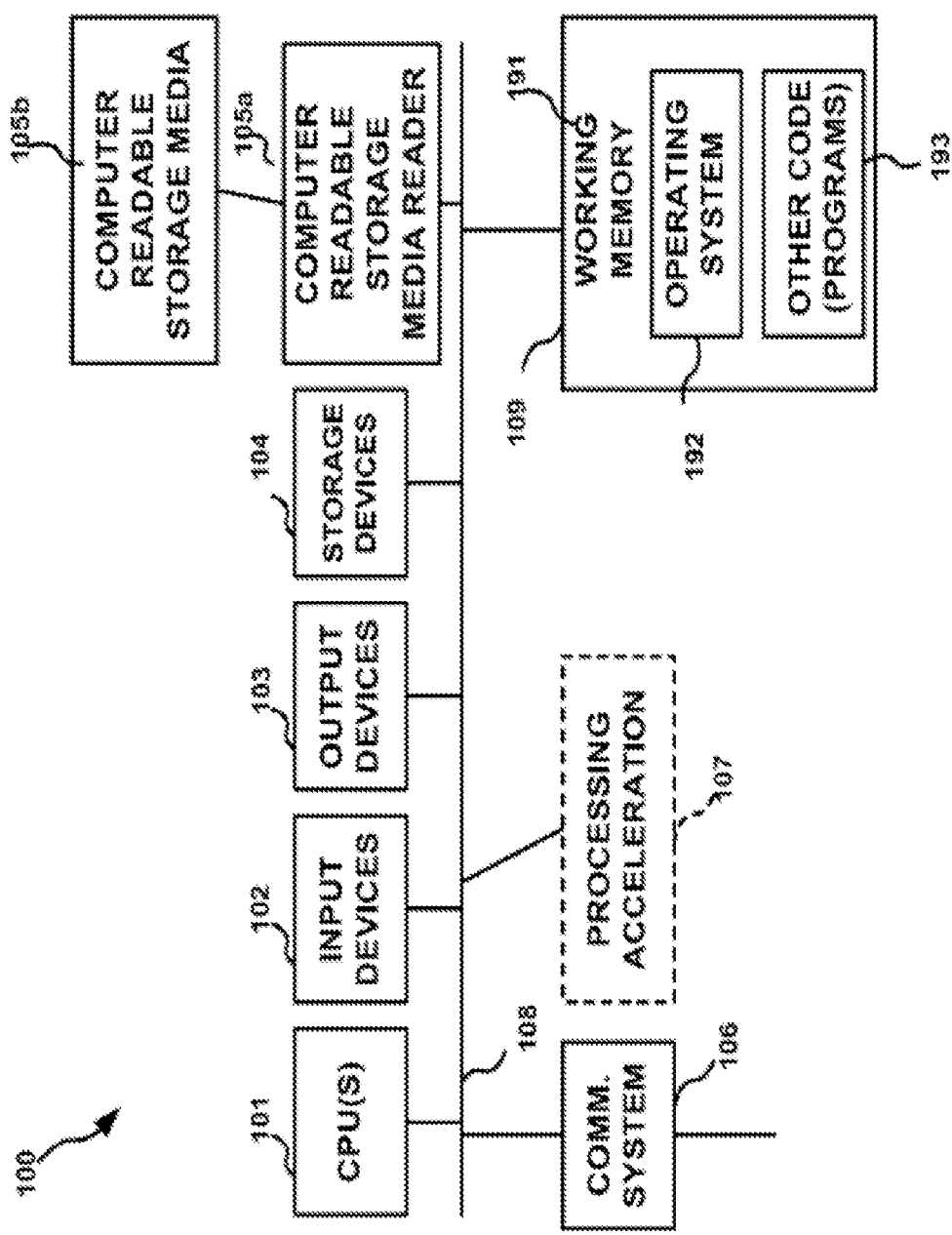
FIG. 12 illustrates a nonlimiting exemplary computer system for use with various computer-implemented methods described herein.
Figure 13:
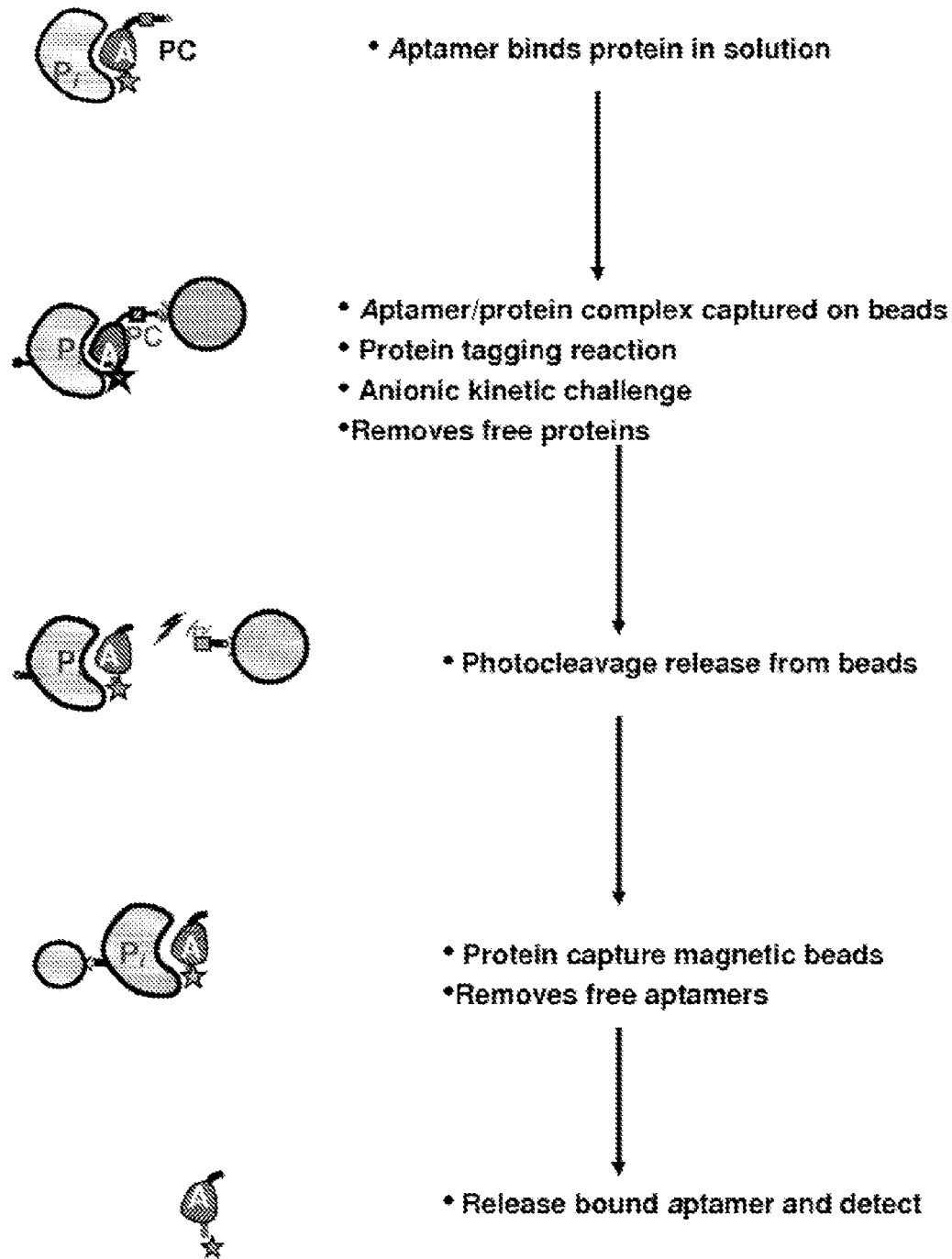
FIG. 13 illustrates a nonlimiting exemplary aptamer assay that can be used to detect one or more biomarkers in a biological sample.

At least some embodiments of the methods described herein can be implemented with the use of a computer. An example of a computer system 100 is shown in FIG. 12. With reference to FIG. 12, system 100 is shown comprised of hardware elements that are electrically coupled via bus 108, including a processor 101, input device 102, output device 103, storage device 104, computer-readable storage media reader 105a, communications system 106, processing acceleration (e.g., DSP or special-purpose processors) 107 and memory 109. Computer-readable storage media reader 105a is further coupled to computer-readable storage media 105b, the combination comprehensively representing remote, local, fixed and/or removable storage devices plus storage media, memory, etc. for temporarily and/or more permanently containing computer-readable information, which can include storage device 104, memory 109 and/or any other such accessible system 100 resource. System 100 also comprises software elements (shown as being currently located within working memory 191) including an operating system 192 and other code 193, such as programs, data and the like.

With respect to FIG. 12, system 100 has extensive flexibility and configurability. Thus, for example, a single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. For example, one or more system elements might be implemented as sub-elements within a system 100 component (e.g., within communications system 106). Customized hardware might also be utilized and/or particular elements might be implemented in hardware, software or both. Further, while connection to other computing devices such as network input/output devices (not shown) may be employed, it is to be understood that wired, wireless, modem, and/or other connection or connections to other computing devices might also be utilized.

In one aspect, the system can comprise a database containing features of biomarkers characteristic of prediction of risk of a CV event. The biomarker data (or biomarker information) can be utilized as an input to the computer for use as part of a computer implemented method. The biomarker data can include the data as described herein.

In one aspect, the system further comprises one or more devices for providing input data to the one or more processors.

The system further comprises a memory for storing a data set of ranked data elements.

In another aspect, the device for providing input data comprises a detector for detecting the characteristic of the data element, e.g., such as a mass spectrometer or gene chip reader.

The system additionally may comprise a database management system. User requests or queries can be formatted in an appropriate language understood by the database management system that processes the query to extract the relevant information from the database of training sets.

The system may be connectable to a network to which a network server and one or more clients are connected. The network may be a local area network (LAN) or a wide area network (WAN), as is known in the art. Preferably, the server includes the hardware necessary for running computer program products (e.g., software) to access database data for processing user requests.

The system may include an operating system (e.g., UNIX or Linux) for executing instructions from a database management system. In one aspect, the operating system can operate on a global communications network, such as the internet, and utilize a global communications network server to connect to such a network.

The system may include one or more devices that comprise a graphical display interface comprising interface elements such as buttons, pull down menus, scroll bars, fields for entering text, and the like as are routinely found in graphical user interfaces known in the art. Requests entered on a user interface can be transmitted to an application program in the system for formatting to search for relevant information in one or more of the system databases. Requests or queries entered by a user may be constructed in any suitable database language.

The graphical user interface may be generated by a graphical user interface code as part of the operating system and can be used to input data and/or to display inputted data. The result of processed data can be displayed in the interface, printed on a printer in communication with the system, saved in a memory device, and/or transmitted over the network or can be provided in the form of the computer readable medium.

The system can be in communication with an input device for providing data regarding data elements to the system (e.g., expression values). In one aspect, the input device can include a gene expression profiling system including, e.g., a mass spectrometer, gene chip or array reader, and the like.

The methods and apparatus for analyzing CV event risk prediction biomarker information according to various embodiments may be implemented in any suitable manner, for example, using a computer program operating on a computer system. A conventional computer system comprising a processor and a random access memory, such as a remotely-accessible application server, network server, personal computer or workstation may be used. Additional computer system components may include memory devices or information storage systems, such as a mass storage system and a user interface, for example a conventional monitor, keyboard and tracking device. The computer system may be a stand-alone system or part of a network of computers including a server and one or more databases.

The CV event risk prediction biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the CV event risk prediction biomarkers. The computer program may comprise multiple modules performing various functions or operations, such as a processing module for processing raw data and generating supplemental data and an analysis module for analyzing raw data and supplemental data to generate a CV event risk prediction status and/or diagnosis or risk calculation. Calculation of risk status for a CV event may optionally comprise generating or collecting any other information, including additional biomedical information, regarding the condition of the individual relative to the disease, condition or event, identifying whether further tests may be desirable, or otherwise evaluating the health status of the individual.

Some embodiments described herein can be implemented so as to include a computer program product. A computer program product may include a computer readable medium having computer readable program code embodied in the medium for causing an application program to execute on a computer with a database.

As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one aspect, a computer program product is provided for evaluation of the risk of a CV event. The computer program product includes a computer readable medium embodying program code executable by a processor of a computing device or system, the program code comprising: code that retrieves data attributed to a biological sample from an individual, wherein the data comprises biomarker levels that each correspond to one of the biomarkers in Table 3; and code that executes a classification method that indicates a CV event risk status of the individual as a function of the biomarker values.

In still another aspect, a computer program product is provided for indicating a likelihood of risk of a CV event. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the biomarkers provided in Table 3; and code that executes a classification method that indicates a CV event risk status of the individual as a function of the biomarker value.

While various embodiments have been described as methods or apparatuses, it should be understood that embodiments can be implemented through code coupled with a computer, e.g., code resident on a computer or accessible by the computer. For example, software and databases could be utilized to implement many of the methods discussed above. Thus, in addition to embodiments accomplished by hardware, it is also noted that these embodiments can be accomplished through the use of an article of manufacture comprised of a computer usable medium having a computer readable program code embodied therein, which causes the enablement of the functions disclosed in this description. Therefore, it is desired that embodiments also be considered protected by this patent in their program code means as well. Furthermore, the embodiments may be embodied as code stored in a computer-readable memory of virtually any kind including, without limitation, RAM, ROM, magnetic media, optical media, or magneto-optical media. Even more generally, the embodiments could be implemented in software, or in hardware, or any combination thereof including, but not limited to, software running on a general purpose processor, microcode, programmable logic arrays (PLAs), or application-specific integrated circuits (ASICs).

It is also envisioned that embodiments could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including the matter incorporated by reference.

The biomarker identification process, the utilization of the biomarkers disclosed herein, and the various methods for determining biomarker values are described in detail above with respect to evaluation of risk of a CV event. However, the application of the process, the use of identified biomarkers, and the methods for determining biomarker values are fully applicable to other specific types of cardiovascular conditions, to any other disease or medical condition, or to the identification of individuals who may or may not be benefited by an ancillary medical treatment.

Other Methods

In some embodiments, the biomarkers and methods described herein are used to determine a medical insurance premium or coverage decision and/or a life insurance premium or coverage decision. In some embodiments, the results of the methods described herein are used to determine a medical insurance premium and/or a life insurance premium. In some such instances, an organization that provides medical insurance or life insurance requests or otherwise obtains information concerning a subject's risk of a CV event and uses that information to determine an appropriate medical insurance or life insurance premium for the subject. In some embodiments, the test is requested by, and paid for by, the organization that provides medical insurance or life insurance. In some embodiments, the test is used by the potential acquirer of a practice or health system or company to predict future liabilities or costs should the acquisition go ahead.

In some embodiments, the biomarkers and methods described herein are used to predict and/or manage the utilization of medical resources. In some such embodiments, the methods are not carried out for the purpose of such prediction, but the information obtained from the method is used in such a prediction and/or management of the utilization of medical resources. For example, a testing facility or hospital may assemble information from the present methods for many subjects in order to predict and/or manage the utilization of medical resources at a particular facility or in a particular geographic area.

EXAMPLES

The following examples are provided for illustrative purposes only and are not intended to limit the scope of the application as defined by the appended claims. Routine molecular biology techniques described in the following examples can be carried out as described in standard laboratory manuals, such as Sambrook et al., Molecular Cloning:

A Laboratory Manual, 3rd. ed., Cold Spring Harbor Laboratory Press, Cold Spring Harbor, N.Y., (2001).

Example 1: Exemplary Biomarker Detection Using Aptamers

An exemplary method of detecting one or more biomarkers in a sample is described, e.g., in Kraemer et al., *PLoS One* 6(10): e26332, and is described below. Three different methods of quantification: microarray-based hybridization, a Luminex bead-based method, and qPCR, are described.

Reagents

HEPES, NaCl, KCl, EDTA, EGTA, MgCl2 and Tween-20 may be purchased, e.g., from Fisher Biosciences. Dextran sulfate sodium salt (DxSO4), nominally 8000 molecular weight, may be purchased, e.g., from AIC and is dialyzed against deionized water for at least 20 hours with one exchange. KOD EX DNA polymerase may be purchased, e.g., from VWR. Tetramethylammonium chloride and CAPSO may be purchased, e.g., from Sigma-Aldrich and streptavidin-phycoerythrin (SAPE) may be purchased, e.g., from Moss Inc. 4-(2-Aminoethyl)-benzenesulfonylfluoride hydrochloride (AEBSF) may be purchased, e.g., from Gold Biotechnology. Streptavidin-coated 96-well plates may be purchased, e.g., from Thermo Scientific (Pierce Streptavidin Coated Plates HBC, clear, 96-well, product number 15500 or 15501). NHS-PEO4-biotin may be purchased, e.g., from Thermo Scientific (EZ-Link NHS-PEO4-Biotin, product number 21329), dissolved in anhydrous DMSO, and may be stored frozen in single-use aliquots. IL-8, MIP-4, Lipocalin-2, RANTES, MMP-7, and MMP-9 may be purchased, e.g., from R&D Systems. Resistin and MCP-1 may be purchased, e.g., from PeproTech, and tPA may be purchased, e.g., from VWR.

Nucleic Acids

Conventional (including amine- and biotin-substituted) oligodeoxynucleotides may be purchased, e.g., from Integrated DNA Technologies (IDT). Z-Block is a single-stranded oligodeoxynucleotide of sequence 5'-(AC-BnBn)7-AC-3', where Bn indicates a benzyl-substituted deoxyuridine residue. Z-block may be synthesized using conventional phosphoramidite chemistry. Aptamer capture reagents may also be synthesized by conventional phosphoramidite chemistry, and may be purified, for example, on a 21.5×75 mm PRP-3 column, operating at 80° C. on a Waters Autopurification 2767 system (or Waters 600 series semi-automated system), using, for example, a timberline TL-600 or TL-150 heater and a gradient of triethylammonium bicarbonate (TEAB)/ACN to elute product. Detection is performed at 260 nm and fractions are collected across the main peak prior to pooling best fractions.

Buffers

Buffer SB18 is composed of 40 mM HEPES, 101 mM NaCl, 5 mM KCl, 5 mM MgCl2, and 0.05% (v/v) Tween 20 adjusted to pH 7.5 with NaOH. Buffer SB17 is SB18 supplemented with 1 mM trisodium EDTA. Buffer PB1 is composed of 10 mM HEPES, 101 mM NaCl, 5 mM KCl, 5 mM MgCl2, 1 mM trisodium EDTA and 0.05% (v/v) Tween-20 adjusted to pH 7.5 with NaOH. CAPSO elution buffer consists of 100 mM CAPSO pH 10.0 and 1 M NaCl. Neutralization buffer contains of 500 mM HEPES, 500 mM HCl, and 0.05% (v/v) Tween-20. Agilent Hybridization Buffer is a proprietary formulation that is supplied as part of a kit (Oligo aCGH/ChIP-on-chip Hybridization Kit). Agilent Wash Buffer 1 is a proprietary formulation (Oligo aCGH/ChIP-on-chip Wash Buffer 1, Agilent). Agilent Wash Buffer 2 is a proprietary formulation (Oligo aCGH/ChIP-on-chip Wash Buffer 2, Agilent). TMAC hybridization solution consists of 4.5 M tetramethylammonium chloride, 6 mM trisodium EDTA, 75 mM Tris-HCl (pH 8.0), and 0.15% (v/v) Sarkosyl. KOD buffer (10-fold concentrated) consists of 1200 mM Tris-HCl, 15 mM MgSO4, 100 mM KCl, 60 mM (NH4)2SO4, 1% v/v Triton-X 100 and 1 mg/mL BSA.

Sample Preparation

Serum (stored at −80° C. in 100 µL aliquots) is thawed in a 25° C. water bath for 10 minutes, then stored on ice prior to sample dilution. Samples are mixed by gentle vortexing for 8 seconds. A 6% serum sample solution is prepared by dilution into 0.94×SB17 supplemented with 0.6 mM MgCl2, 1 mM trisodium EGTA, 0.8 mM AEB SF, and 2 µM Z-Block. A portion of the 6% serum stock solution is diluted 10-fold in SB17 to create a 0.6% serum stock. 6% and 0.6% stocks are used, in some embodiments, to detect high- and low-abundance analytes, respectively.

Capture Reagent (Aptamer) and Streptavidin Plate Preparation

Aptamers are grouped into 2 mixes according to the relative abundance of their cognate analytes (or biomarkers). Stock concentrations are 4 nM for each aptamer, and the final concentration of each aptamer is 0.5 nM. Aptamer stock mixes are diluted 4-fold in SB17 buffer, heated to 95° C. for 5 min and cooled to 37° C. over a 15 minute period prior to use. This denaturation-renaturation cycle is intended to normalize aptamer conformer distributions and thus ensure reproducible aptamer activity in spite of variable histories. Streptavidin plates are washed twice with 150 µL buffer PB1 prior to use.

Equilibration and Plate Capture

Heat-cooled 2× Aptamer mixes (55 µL) are combined with an equal volume of 6% or 0.6% serum dilutions, producing equilibration mixes containing 3% and 0.3% serum. The plates are sealed with a Silicone Sealing Mat (Axymat Silicone sealing mat, VWR) and incubated for 1.5 h at 37° C. Equilibration mixes are then transferred to the wells of a washed 96-well streptavidin plate and further incubated on an Eppendorf Thermomixer set at 37° C., with shaking at 800 rpm, for two hours.

Manual Assay

Unless otherwise specified, liquid is removed by dumping, followed by two taps onto layered paper towels. Wash volumes are 150 µL and all shaking incubations are done on an Eppendorf Thermomixer set at 25° C., 800 rpm. Equilibration mixes are removed by pipetting, and plates are washed twice for 1 minute with buffer PB1 supplemented with 1 mM dextran sulfate and 500 µM biotin, then 4 times for 15 seconds with buffer PB1. A freshly made solution of 1 mM NHS-PEO4-biotin in buffer PB1 (150 µL/well) is added, and plates are incubated for 5 minutes with shaking. The NHS-biotin solution is removed, and plates washed 3 times with buffer PB1 supplemented with 20 mM glycine, and 3 times with buffer PB1. Eighty-five µL of buffer PB1 supplemented with 1 mM DxSO4 is then added to each well, and plates are irradiated under a BlackRay UV lamp (nominal wavelength 365 nm) at a distance of 5 cm for 20 minutes with shaking. Samples are transferred to a fresh, washed streptavidin-coated plate, or an unused well of the existing washed streptavidin plate, combining high and low sample dilution mixtures into a single well. Samples are incubated at room temperature with shaking for 10 minutes. Unadsorbed material is removed and the plates washed 8 times for 15 seconds each with buffer PB1 supplemented with 30% glycerol. Plates are then washed once with buffer PB1. Aptamers are eluted for 5 minutes at room temperature with 100 µL CAPSO elution buffer. 90 µL of the eluate is transferred to a 96-well HybAid plate and 10 µL neutralization buffer is added.

Semi-Automated Assay

Streptavidin plates bearing adsorbed equilibration mixes are placed on the deck of a BioTek EL406 plate washer, which is programmed to perform the following steps: unadsorbed material is removed by aspiration, and wells are washed 4 times with 300 µL of buffer PB1 supplemented with 1 mM dextran sulfate and 500 µM biotin. Wells are then washed 3 times with 300 µL buffer PB1. One hundred fifty µL of a freshly prepared (from a 100 mM stock in DMSO) solution of 1 mM NHS-PEO4-biotin in buffer PB1 is added. Plates are incubated for 5 minutes with shaking. Liquid is aspirated, and wells are washed 8 times with 300 µL buffer PB1 supplemented with 10 mM glycine. One hundred µL of buffer PB1 supplemented with 1 mM dextran sulfate are added. After these automated steps, plates are removed from the plate washer and placed on a thermoshaker mounted under a UV light source (BlackRay, nominal wavelength 365 nm) at a distance of 5 cm for 20 minutes. The thermoshaker is set at 800 rpm and 25° C. After 20 minutes irradiation, samples are manually transferred to a fresh, washed streptavidin plate (or to an unused well of the existing washed plate). High-abundance (3% serum+3% aptamer mix) and low-abundance reaction mixes (0.3% serum+0.3% aptamer mix) are combined into a single well at this point. This "Catch-2" plate is placed on the deck of BioTek EL406 plate washer, which is programmed to perform the following steps: the plate is incubated for 10 minutes with shaking. Liquid is aspirated, and wells are washed 21 times with 300 µL buffer PB1 supplemented with 30% glycerol. Wells are washed 5 times with 300 µL buffer PB1, and the final wash is aspirated. One hundred µL CAPSO elution buffer are added, and aptamers are eluted for 5 minutes with shaking. Following these automated steps, the plate is then removed from the deck of the plate washer, and 90 µL aliquots of the samples are transferred manually to the wells of a HybAid 96-well plate that contains 10 µL neutralization buffer.

Hybridization to Custom Agilent 8×15 k Microarrays

24 µL of the neutralized eluate is transferred to a new 96-well plate and 6 µL of 10× Agilent Block (Oligo aCGH/ChIP-on-chip Hybridization Kit, Large Volume, Agilent 5188-5380), containing a set of hybridization controls composed of 10 Cy3 aptamers is added to each well. Thirty µL 2× Agilent Hybridization buffer is added to each sample and mixed. Forty µL of the resulting hybridization solution is manually pipetted into each "well" of the hybridization gasket slide (Hybridization Gasket Slide, 8-microarray per slide format, Agilent). Custom Agilent microarray slides, bearing 10 probes per array complementary to 40 nucleotide random region of each aptamer with a 20×dT linker, are placed onto the gasket slides according to the manufacturers' protocol. The assembly (Hybridization Chamber Kit—SureHyb-enabled, Agilent) is clamped and incubated for 19 hours at 60° C. while rotating at 20 rpm.

Post Hybridization Washing

Approximately 400 mL Agilent Wash Buffer 1 is placed into each of two separate glass staining dishes. Slides (no more than two at a time) are disassembled and separated while submerged in Wash Buffer 1, then transferred to a slide rack in a second staining dish also containing Wash Buffer 1. Slides are incubated for an additional 5 minutes in Wash Buffer 1 with stirring. Slides are transferred to Wash Buffer 2 pre-equilibrated to 37° C. and incubated for 5 minutes with stirring. Slides are transferred to a fourth staining dish containing acetonitrile, and incubated for 5 minutes with stirring.

Microarray Imaging

Microarray slides are imaged with an Agilent G2565CA Microarray Scanner System, using the Cy3-channel at 5 µm resolution at 100% PMT setting, and the XRD option enabled at 0.05. The resulting TIFF images are processed using Agilent feature extraction software version 10.5.1.1 with the GE1_105_Dec08 protocol.

Luminex Probe Design

Probes immobilized to beads have 40 deoxynucleotides complementary to the 3' end of the 40 nucleotide random region of the target aptamer. The aptamer complementary region is coupled to Luminex Microspheres through a hexaethyleneglycol (HEG) linker bearing a 5' amino terminus. Biotinylated detection deoxyoligonucleotides comprise 17-21 deoxynucleotides complementary to the 5' primer region of target aptamers. Biotin moieties are appended to the 3' ends of detection oligos.

Coupling of Probes to Luminex Microspheres

Probes are coupled to Luminex Microplex Microspheres essentially per the manufacturer's instructions, but with the following modifications: amino-terminal oligonucleotide amounts are 0.08 nMol per $2.5 \times 10^6$ microspheres, and the second EDC addition is 5 µL at 10 mg/mL. Coupling reactions are performed in an Eppendorf ThermoShaker set at 25° C. and 600 rpm.

Microsphere Hybridization

Microsphere stock solutions (about 40000 microspheres/µL) are vortexed and sonicated in a Health Sonics ultrasonic cleaner (Model: T1.9C) for 60 seconds to suspend the microspheres. Suspended microspheres are diluted to 2000 microspheres per reaction in 1.5×TMAC hybridization solutions and mixed by vortexing and sonication. Thirty-three µL per reaction of the bead mixture are transferred into a 96-well HybAid plate. Seven µL of 15 nM biotinylated detection oligonucleotide stock in 1× TE buffer are added to each reaction and mixed. Ten µL of neutralized assay sample are added and the plate is sealed with a silicon cap mat seal. The plate is first incubated at 96° C. for 5 minutes and incubated at 50° C. without agitation overnight in a conventional hybridization oven. A filter plate (Dura pore, Millipore part number MSBVN1250, 1.2 µm pore size) is prewetted with 75 µL 1×TMAC hybridization solution supplemented with 0.5% (w/v) BSA. The entire sample volume from the hybridization reaction is transferred to the filter plate. The hybridization plate is rinsed with 75 µL 1×TMAC hybridization solution containing 0.5% BSA and any remaining material is transferred to the filter plate. Samples are filtered under slow vacuum, with 150 µL buffer evacuated over about 8 seconds. The filter plate is washed once with 75 µL 1×TMAC hybridization solution containing 0.5% BSA and the microspheres in the filter plate are resuspended in 75 µL 1×TMAC hybridization solution containing 0.5% BSA. The filter plate is protected from light and incubated on an Eppendorf Thermalmixer R for 5 minutes at 1000 rpm. The filter plate is then washed once with 75 µL 1×TMAC hybridization solution containing 0.5% BSA. 75 µL of 10 µg/mL streptavidin phycoerythrin (SAPE-100, MOSS, Inc.) in 1×TMAC hybridization solution is added to each reaction and incubated on Eppendorf Thermalmixer Rat 25° C. at 1000 rpm for 60 minutes. The filter plate is washed twice with 75 µL 1×TMAC hybridization solution containing 0.5% BSA and the microspheres in the filter plate are resuspended in 75 µL 1×TMAC hybridization solution containing 0.5% BSA. The filter plate is then incubated protected from light on an Eppendorf ThermalMixer R for 5 minutes, 1000 rpm. The filter plate is then washed once with 75 μL 1×TMAC hybridization solution containing 0.5% BSA. Microspheres are resuspended in 75 μL 1×TMAC hybridization solution supplemented with 0.5% BSA, and analyzed on a Luminex 100 instrument running XPonent 3.0 software. At least 100 microspheres are counted per bead type, under high PMT calibration and a doublet discriminator setting of 7500 to 18000.

QPCR Read-Out

Standard curves for qPCR are prepared in water ranging from 108 to 102 copies with 10-fold dilutions and a no-template control. Neutralized assay samples are diluted 40-fold into diH2O. The qPCR master mix is prepared at 2× final concentration (2×KOD buffer, 400 μM dNTP mix, 400 nM forward and reverse primer mix, 2×SYBR Green I and 0.5 U KOD EX). Ten of 2×qPCR master mix is added to 10 μL of diluted assay sample. qPCR is run on a BioRad MyIQ iCycler with 2 minutes at 96° C. followed by 40 cycles of 96° C. for 5 seconds and 72° C. for 30 seconds.

Example 2. Methods

Study Design and Sample Collection

Archived plasma samples from subjects with stable CHD were obtained from two well-known, independent cohort studies. The characteristics of the study population are shown in Table 1. We performed protein biomarker discovery and model training in 938 plasma samples from the Heart and Soul study, with subsequent follow-up of 10 years. See, e.g., Shlipak et al., *Am J Med.* 2008; 121:50-57; Whooley et al., *JAMA.* 2008; 300:2379-2388. We validated the model on 971 samples from HUNT3, a Norwegian prospective cohort study with follow-up of 5 years. See Krokstad et al., *Int J Epidemiol.* 2013; 42:968-977. We used the Heart and Soul inclusion and exclusion criteria to select all the participants with stable CHD from the larger HUNT3 cohort for this analysis. The discovery plasma samples were representative of a well-controlled academic prospective study: subjects were fasted, samples collected at the same time of day and centrifuged and frozen at −80° C. within an hour of collection. In contrast, sample collection in the HUNT3 validation set was representative of likely "real world" conditions; subjects were not fasted, were seen at varying times of day, and plasma was not separated from cells for up to 24 h while samples remained at 4° C. Assessing the model performance in this manner allows us to ascertain the robustness of the model to factors associated with practical collection of clinical samples, an important consideration for biomarker validation. See McShane et al., *Nature.* 2013; 502:317-320. Both studies were approved by the relevant institutional review boards.

TABLE 1

| | Study population characteristics | |
|---|---|---|
| | Discovery (Heart and Soul) | Validation (HUNT3) |
| Sample origin | Prospective UCSF-based cohort study in 12 outpatient clinics in the San Francisco Bay Area | Nested cohort of 1017 patients from Norwegian prospective cohort study in 50,807 participants |
| Entry criteria | Stable coronary heart disease diagnoses by prior MI, >50% stenosis on angiogram, exercise induced ischemia, prior revascularization | All subjects had stable coronary heart disease, selected by same criteria as for Heart and Soul cohort, except exercise data were not available. |
| Sample processing | Collection dates: 2000-2002<br>Fasting<br>Fixed time of day<br>EDTA plasma<br>Time to separation from cells typically <1 hr<br>Storage at −80° C. | Collection dates: 2006-2008<br>Non fasting<br>Random time of day<br>EDTA plasma<br>Time to separation from cells up to 24 h, sample held at 4° C.<br>Storage at −80° C. |
| Event and event adjudication | Composite event endpoint defined as the first of: death from any cause; hospitalization for myocardial infarction; stroke or transient ischemic attack; hospitalization for signs and symptoms of heart failure. Each event was adjudicated by 2 independent and blinded reviewers. In the event of disagreement, the adjudicators conferred, reconsidered their classification, and, if needed, requested consultation from a third blinded adjudicator. | Event definitions are the same as for discovery, adjudicated from medical record review by an experienced cardiologist |
| Follow-up Time | Date of last follow-up: 11.09 Years<br>Median (IQR) follow-up time: 7.9 (5.5) Years | Date of last follow-up: 5.57 Years<br>Median (IQR) follow-up time: 4.3(1.0) Years |
| Blinding | Laboratory technicians blinded to clinical characteristics and outcomes. Outcomes adjudication blinded to proteomic results. | Laboratory technicians blinded to clinical characteristics and outcomes. Outcomes adjudication blinded to proteomic results. |
| Model application | Biomarkers identified, models trained, models applied | No biomarkers identified, no models trained, only Heart and Soul-trained models applied |

SOMAscan Proteomic Assay

The individual affinity reagents used in the protein assay are slow off-rate modified DNA aptamers (SOMAmers) with very high affinity to their protein targets. See Vaught et al., *J Am Chem Soc.* 2010; 132:4141-4151. Chemical modifications to the DNA bases in the aptamers enhance their binding characteristics. See Davies et al., *Proc Natl Acad Sci USA.* 2012; 109:19971-19976. We used 1130 of these reagents in the SOMAscan™ multiplex assay 8-10. In brief, a sample of plasma in each well of a 96 well plate is incubated with a mixture of SOMAmers that bind to their target proteins. Two bead-based immobilization steps enable the elimination of unbound or non-specifically bound proteins and the elimination of unbound SOMAmers. Only target-protein-bound reagents survive the assay, with the number of each one quantitatively proportional to the protein concentration in the original sample. The DNA in each reagent is quantified on an Agilent hybridization array, and the samples normalized and calibrated such that the degree of fluorescence on the spot on the array relates to the concentration of a specific protein. The 1054 proteins that passed quality control had median intra-assay and inter-assay coefficient of variation <5%. See Gold et al., *PLoS One.* 2010; 5:e15004.

SOMAscan Assay and Data

Plasma samples were assayed over a period of 3 working weeks in 32 separate assay runs. Study samples were randomly assigned to assay runs along with a set of calibration and control samples. No identifying information was available to the laboratory technicians operating the assay.

Intra-run normalization and inter-run calibration were performed according to SOMAscan Version 3 assay data quality control (QC) procedures as defined in the SomaLogic good laboratory practice (GLP) quality system. Inter-run calibration is designed to remove "batch effects" between the successive assay runs while intra-run normalization removes bulk changes in protein concentration (and hence signal intensity) between samples within each run.

Briefly, inter-run calibration scales the signal level for each protein so that that observed level in the run calibration standard matches the expected level represented by the external calibration reference. QC tolerances are defined in terms of the magnitude of the multiplicative scaling required to match the median signal level on the replicate calibration standards to the signal levels generated by external reference.

Intra-run normalization controls for "bulk" signal intensity biases that can result from either differential hybridization efficiency or differential sample dilution (or other collection protocol artifacts) that change the total protein concentration in the sample. The former effect is captured by a set of controls used to monitor the hybridization reaction for each sample and the latter uses the median of the ratio of median signal levels in each sample to the median signal level over all samples within the run. It is not uncommon for differences in sample collection protocol to generate a systematic intensity bias in the signal levels for a large number of proteins. FIG. 1 shows box plots of the multiplicative scale factors in the two cohorts when the 1130 proteins are grouped by sample dilution. Proteins measured in the 40% and 1% sample dilutions had systematically higher(lower) signal levels in the validation(discovery) set resulting in corresponding normalization scale factors smaller(larger) than one. After the normalization procedure the median signal level for proteins in each of the three dilutions is the same in the discovery and validations sets.

Protein levels are reported in relative fluorescence units (RFU) and were log transformed prior to subsequent analysis.

Samples and Proteins Excluded from Analysis

Proteins were excluded from the analysis if the associated inter-run calibration quality control (QC) tolerance was exceeded in at least one of the 32 independent assay runs. This happened for 76 proteins; in many cases the majority of the runs were within the required tolerance, but for simplicity we chose to exclude all 76 proteins in the biomarker discovery analysis presented here.

Samples were excluded from the biomarker discovery analysis for the following reasons: 1) failure to meet the intra-run normalization QC tolerance, 2) an unusually high number of outliers, or 3) evidence of hemolysis as indicated by either extreme levels of hemoglobin or assay technicians noting aberrant (red) plasma color. Single protein outliers were defined as proteins with signal levels outside of the range given by the median ±6*median absolute deviations (MADN)[1]—patient samples with outliers in more than 5% of the measured proteins were excluded from the analysis. Table 2 summarizes the number of samples excluded based on each criteria.

[1] Let $\Phi^{-1}(z)$ denote the inverse of the normal cumulative distribution function. Then for normally distributed data the robust estimate $MADN(x)=\sigma*\Phi^{-1}(3/4)$, so $3*MADN\approx 2\sigma$ and the stated range is $\pm 4\sigma$ for Gaussian measurements.

TABLE 2

| | Samples excluded by criteria | | | |
| --- | --- | --- | --- | --- |
| | Normalization QC criteria failed | Potential Hemolysis | >5% Protein Outliers | Total |
| Discovery Set | 18 | 22 | 15 | 55 |
| Validation Set | 10 | 27 | 10 | 47 |
| total | 28 | 49 | 25 | |

Statistical Methods

The outcome in this study was defined as the first event among death, myocardial infarction (MI), stroke, transient ischemic attack (TIA), or heart failure hospitalization. We used Cox proportional hazards models to estimate the univariate associations between protein levels and risk of cardiovascular events, as follows.

Selection of Proteins Predictive of Cardiovascular Risk

Figure 2:
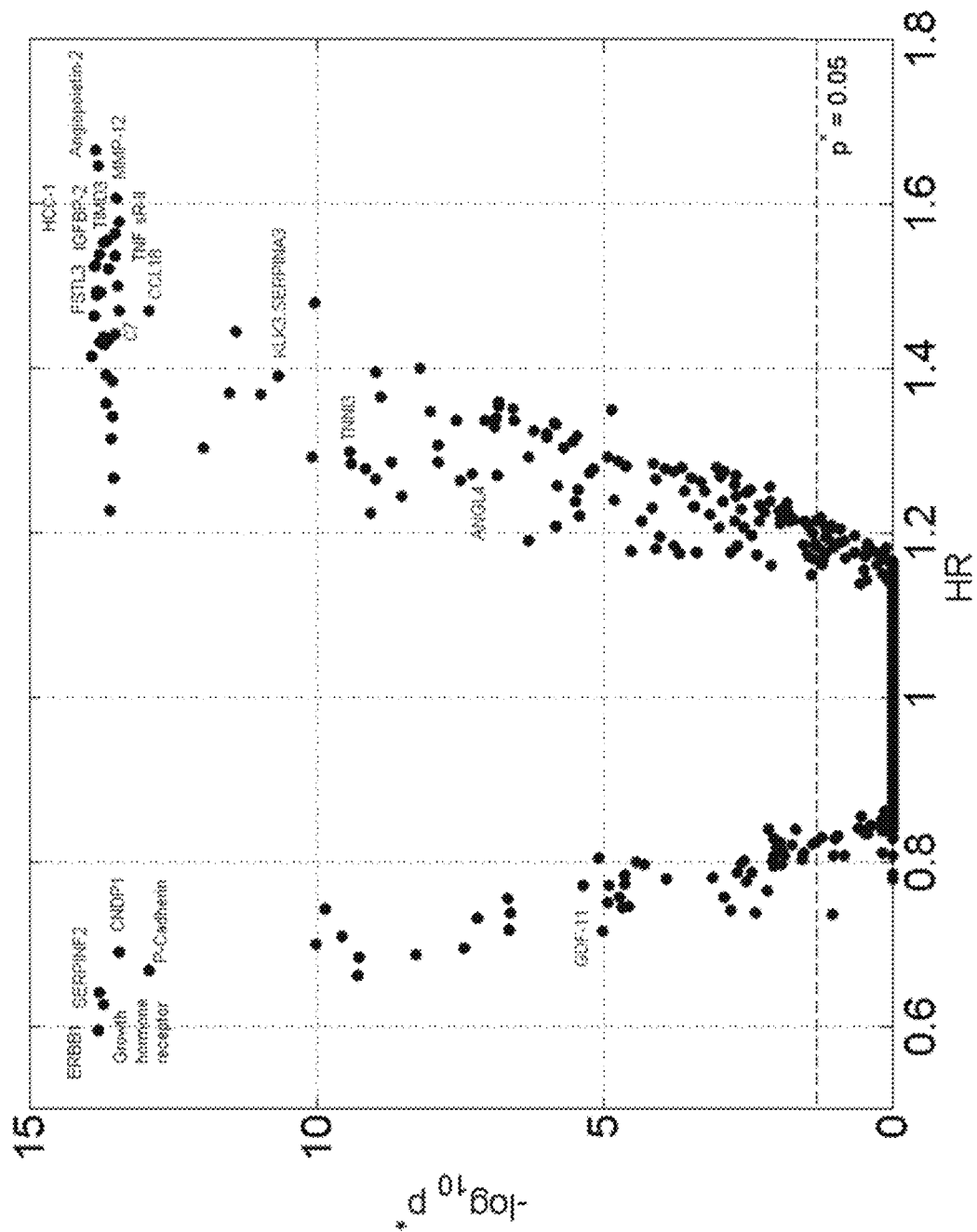
FIG. 2 shows volcano plots of the univariate Cox model hazard ratios per standard deviation of RFU (top) or between outer RFU quartiles (bottom). Horizontal dashed line indicates Bonferroni corrected p=0.05 significance level. National Center for Biotechnology Information (NCBI) gene names are used as succinct labels for proteins with extreme hazard ratios. Proteins labeled in red are included in the CVD9 model: ANGPT2="Angiopoietin-2"; C7="Complement C7"; SERPINF2="serine protease inhibitor F2" or "α2-Antiplasmin"; CCL18="Chemokine (C—C motif) ligand 18" also known as "Pulmonary and activation-regulated chemokine (PARC)"; ANGL4="Angiopoietin-related protein 4"; KLK3.SERPINA3="α1-antichymotrypsin complex"; and TNNI3="Troponin-I, cardiac".
Figure 2:
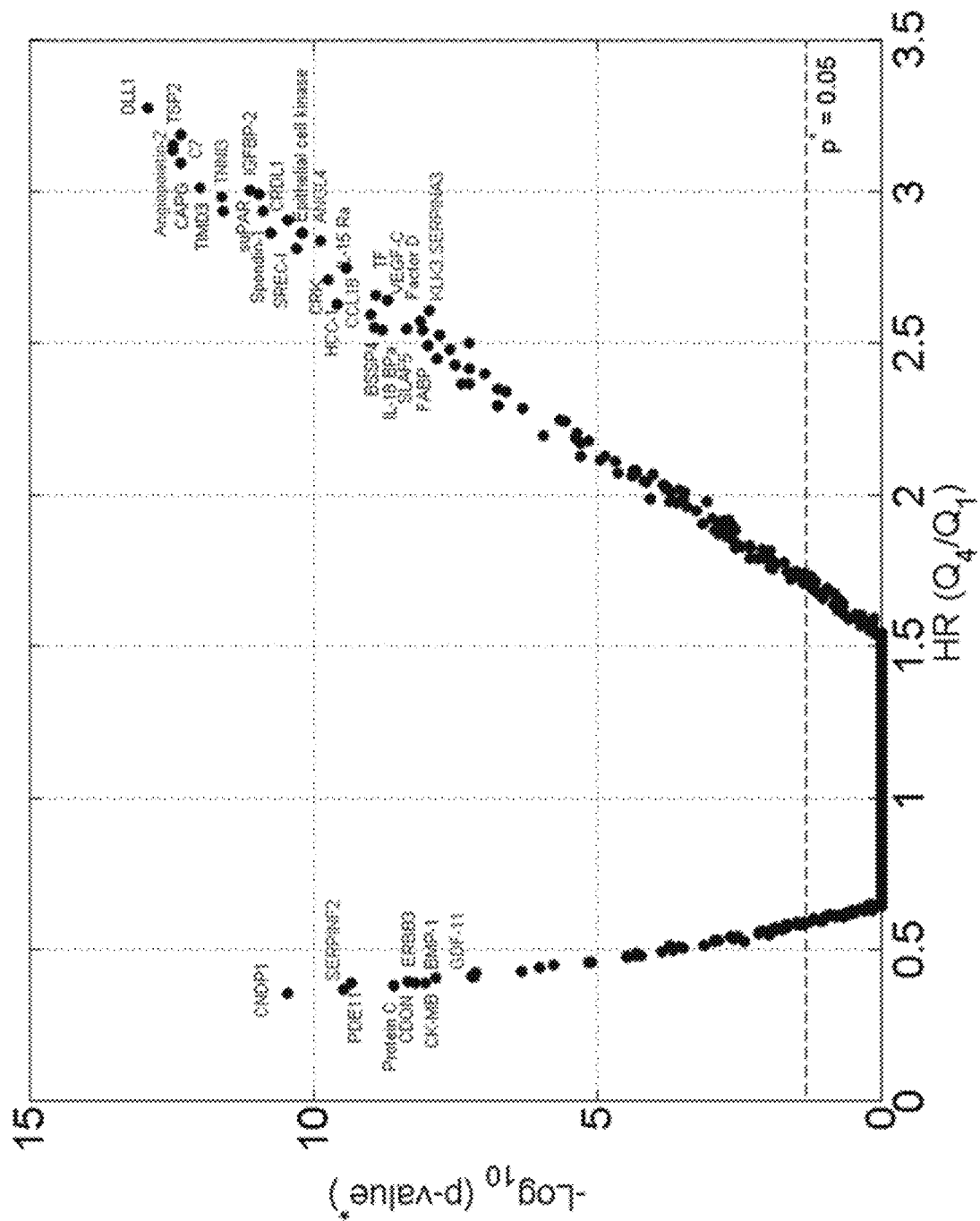

Single variable Cox proportional hazard models were used to identify a set of proteins individually associated with increased risk of secondary cardiovascular events. At a 5% Bonferroni corrected significance level, exactly 200 proteins were associated with increased risk of cardiovascular outcomes. The "volcano" plots in FIG. 2 show the negative logarithm of the Wald statistic p-value as a function of the hazard ratio either per standard deviation of relative fluorescence units (RFU) (top) or between the extreme levels of the categorical indicator for RFU quartile membership (bottom). In the latter case the reported hazard ratio gives the increase in hazard experienced by a subject in the highest risk (4th) quartile compared to a subject in the lowest risk ($1^{st}$) quartile.

Some of these 200 proteins are associated with relatively small effect sizes, but the 117 listed in Table 14 have hazard ratios outside the range [0.75-1.25]. Examining the corresponding correlation structure (data not shown) among these 200 proteins reveals several clusters of proteins with similar pair-wise correlations. A comprehensive discussion of the biological function of these protein clusters is beyond the scope of this manuscript and will be discussed elsewhere.

The LASSO (Tibshirani, *Stat Med* 1997; 16:385-95) was used as a variable screening procedure to identify a subset of proteins jointly associated with increased CV risk. Generalized cross-validation using coxnet (Simon et al., *Journal of Statistical Software* 2011; 39:1-13) in the R package glmnet (Friedman et al., *Journal of Statistical Software* 2010; 33:1-22) was used to set the LASSO regularization parameter. We used the "one standard error" heuristic (Hastie et al., Elements of Statistical Learning, Second ed. 2 ed: Springer; 2009) for setting the regularization level. Perturbing the cross-validation step was used as a simple check on the "stability" of the resulting set of selected proteins. This analysis gave us confidence that the proteins included in CVD9 are "stable" inasmuch as they would be selected the majority of the time the "LASSO followed by backward elimination" procedure was applied. To generate reproducible results for the ensuing analysis we fixed the random number seed at 1 prior to LASSO cross-validation. Initializing this value and setting the LASSO regularization parameter to the value 1 standard error above that which minimizes the cross-validated partial likelihood deviance results in a LASSO model containing the 16 proteins discussed herein.

We used LASSO for variable selection only, preferring the fully parametric (Weibull) survival model as a final prognostic model. The latter has a simple representation and a mathematical form amenable (Royston et al., *BMC medical research methodology* 2013; 13:33; van Houwelingen, *Stat Med* 2000; 19:3401-15) to calibration for use in external validation studies. Stepwise backward elimination started from the full LASSO model was used to remove proteins that were not significant predictors in the absence of the constraint imposed by the LASSO penalty. When using the Bayesian information criterion (BIC) stopping criteria to balance model performance and complexity, backward elimination discarded 7 proteins: Cathepsin H, EGF receptor, Growth hormone receptor, T cell membrane protein TIM-3, MMP-7, Cell adhesion oncogene-related CDO and Thrombospondin-2 resulting in the 9 protein CVD9 model shown in Table 3.

meaningful improvement in either the discrimination or calibration performance over that achieved with the "proteins only" model in the discovery set. This led us to designate CVD9 as our "primary" model for assessing validation performance and a model including age, sex, diabetes status and estimated glomerular filtration rate (eGFR) as a secondary model.

For an accelerated failure time model, the probability of an event occurring in the interval [0,t] is given by $$Pr[T \le t] = 1 - e^{-e^{\left(\frac{Log(t)-PI}{s}\right)}},$$

where PI is the prognostic index (or linear predictor) and s is the associated scale parameter for the extreme value distribution. When fitting the model we worked with standardized variables—here we have absorbed the population mean and standard deviation into the intercept term so we can report the prognostic index and scale factor as, PI=−16.61+1.55×ANGPT2−1.22×GDF11+2.12×C7−2.64×SERPINF2+0.57×CCL18+1.02×ANGPTL4+1.43×KLK3.SERPINA3+0.72×MMP12+0.59×TNNI3, s=0.85 where protein levels are taken to be in log 10 RFU.

Incorporating Clinical Variables

The HUNT3 study was not designed specifically as a cardiovascular disease study so some medical history parameters and clinical laboratory measurements that were available in the discovery set were not available in the validation set (e.g. echocardiographic left ventricular ejection fraction, left ventricular hypertrophy, diastolic function). With this in mind we only considered adjusting for clinical variables that were available in both collections and differed between patients with events and those without.

When added to CVD9, the clinical variables sex(male), age, diabetes(yes), ACE inhibitors(yes), and estimated glomerular filtration rate(eGFR) individually (and jointly) increased the fit of resulting combined model (p<0.001). ACE inhibitor or ARB use was not included in the final model, because medication was not available in the HUNT3 cohort.

TABLE 3

Analytical performance characteristics of the CVD9 biomarkers

| Target | % Sample Dilution | Calibrator % CV | Limits of Quantification (pg/ml) | | Range (Logs) | Inter-Assay Precision (n = 3) (% CV) | | |
|---|---|---|---|---|---|---|---|---|
| | | | Lower | upper | | Low | Med | High |
| Angiopoietin-2 | 0.01 | 5.66 | 8.4 × 10⁰ | 1.8 × 10⁴ | 3.3 | 1.6 | 2.0 | 0.6 |
| Complement C7 | 0.00 | 8.66 | 1.7 × 10¹ | 3.0 × 10⁴ | 3.2 | 7.0 | 7.2 | 6.3 |
| MMP12 | 0.40 | 4.89 | 2.8 × 10⁻¹ | 1.4 × 10⁴ | 4.7 | 1.1 | 2.0 | 2.5 |
| Troponin I, cardiac | 0.40 | 7.62 | — | — | — | — | — | — |
| Angiopoietin-related protein 4 | 0.40 | 6.46 | 1.4 × 10¹ | 1.4 × 10⁴ | 3.0 | 9.6 | 4.9 | 7.6 |
| α1-antichymotrypsin complex | 0.00 | 5.97 | 1.8 × 10⁰ | 1.9 × 10⁴ | 4.0 | 4.5 | 5.8 | 5.3 |
| GDF11 | 0.01 | 6.03 | 6.5 × 1⁰ | 4.2 × 10³ | 2.8 | 1.5 | 1.2 | 3.6 |
| CCL18/PARC | 0.00 | 6.83 | 1.6 × 10⁻¹ | 2.6 × 10³ | 4.2 | 5.1 | 1.6 | 5.6 |
| α2-Antiplasmin | 0.00 | 7.46 | 9.8 × 10⁰ | 1.7 × 10⁴ | 3.2 | 3.7 | 2.7 | 1.8 |

CVD9 Model

The final model (CVD9) contains the 9 proteins. While adjusting this model for clinical variables improved the fit slightly (see below) these adjustments failed to produce a In addition to the 9 proteins used in CVD9 we first added age and sex, and then added diabetes status and eGFR to give to additional models that combine proteins and commonly available clinical variables that were predictive of outcome. Point estimates for the coefficients of the accelerated failure time (AFT) model linear predictor and the estimated scale parameter for the extreme value distribution are listed in Table 4. In Table 4, Abbreviations are ANGPT2="Angiopoietin-2"; C7="Complement C7"; SERPINF2="α2-Antiplasmin"; CCL18="Chemokine (C—C motif) ligand 18" also known as "Pulmonary and activation-regulated chemokine (PARC)", ANGL4="Angiopoietin-related protein 4; KLK3.SERPINA3="α1-antichymotrypsin complex"; TNNI3="Troponin-I, cardiac"; and eGFR="estimated glomerular filtration rate".

comparing the enlarged model to the protein only model. Subsequent measures of discrimination are the weighted area under the incident/dynamic ROC curve ($C^τ$), the integrated discrimination index (IDI), the net reclassification index (NRI) and the fourth to first quartile hazard ratio (Q4/Q1). Calibration performance assessed with the Hosmer-Lemeshow statistic.

Adding clinical variables whose baseline values distinguish the event and no-event groups gives a slight improvement in the point estimates of IDI, NRI(>0) and Q4/Q1 hazard ratio, though the integrated AUC "C-statistic" remain essentially unchanged.

TABLE 5

Measures of discrimination and calibration performance in the discovery set for model CVD9

| Model | LR test p-value | $C^τ$ Year 1 | Year 4 | IDI | NRI NRI (>0) | Event | No Event | Hazard Ratio Q4/Q1 | Calibration Hosmer-Lemeshow $χ^2$ | p-value |
|---|---|---|---|---|---|---|---|---|---|---|
| Protein Only (CVD9) | NA | 0.76 (0.72-0.79) | 0.74 (0.71-0.77) | 0.15 (0.11-0.18) | 0.57 (0.42-0.70) | 0.16 (0.01-0.30) | 0.41 (0.35-0.47) | 8.2 | 8.14 | 0.42 |
| CVD9 + Age + Male | 0.0002 | 0.76 (0.73-0.79) | 0.75 (0.72-0.77) | 0.16 (0.12-0.20) | 0.64 (0.50-0.76) | 0.19 (0.08-0.30) | 0.45 (0.37-0.50) | 10.0 | 2.69 | 0.95 |
| CVD9 + Age + Male + Diabetes + eGFR[2] | 6.3e-6 | 0.77 (0.73-0.79) | 0.75 (0.72-0.77) | 0.17 (0.13-0.20) | 0.68 (0.54-0.80) | 0.22 (0.11-0.32) | 0.46 (0.39-0.52) | 10.3 | 3.81 | 0.87 |

[2]CKD-EPI 2009 eGFR formula was used because it was available in both discovery and validation set.

TABLE 4

Estimated coefficients for 3 candidate models

| Model Term | CVD9 | CVD9 + Age + Sex | CVD9 + Age + Sex + Diabetes + eGFR |
|---|---|---|---|
| Scale | 0.848 | 0.849 | 0.845 |
| Intercept | -16.612 | -18.614 | -17.478 |
| Diabetes = Yes | 0 | 0 | 0.277 |
| eGFR | 0 | 0 | -0.005 |
| Age | 0 | 0.012 | 0.012 |
| Sex = Male | 0 | 0.358 | 0.391 |
| ANGPT2 | 1.547 | 1.712 | 1.510 |
| GDF11 | -1.224 | -1.320 | -1.347 |
| C7 | 2.115 | 2.092 | 2.025 |
| SERPINF2 | -2.643 | -2.057 | -1.663 |
| CCL18 | 0.574 | 0.554 | 0.375 |
| ANGL4 | 1.022 | 0.902 | 0.848 |
| KLK3.SERPINA3 | 1.433 | 1.409 | 1.361 |
| MMP12 | 0.718 | 0.522 | 0.436 |
| TNNI3 | 0.588 | 0.587 | 0.610 |

Several different measures of discrimination performance are commonly reported—we report a "c-statistic", the Integrated Discrimination Index (IDI) and the category-free net reclassification index (NRI).

Table 5 lists these discrimination measures along with the Q4/Q1 hazard ratio and the Hosmer-Lemeshow statistic to summarized calibration performance for the 3 models. Confidence intervals reported are empirical 95% CI generated using 100 bootstrap samples. The first column lists the p-value for the likelihood ratio test comparing the enlarged models to the baseline (protein only) model. The first column gives the p-value for the likelihood ratio (LR) test Re-Calibrating CVD9 for Validation Before comparing the performance of CVD9 to the Framingham score both models were re-calibrated for its use in the validation set. As in van Houwelingen (*Stat Med* 2000; 19:3401-15) we used a Weibull accelerated failure time calibration model to re-calibrate the model coefficients for use in the validation population. If we let PI be the prognostic index and H(t|PI) denote the cumulative hazard function, then the calibration model is $$\log(H(t|PI)) = γ_0 + γ_1 PI + γ_2 e$$

where the error term e, has an extreme value distribution. Denoting the baseline cumulative hazard by $H_0(t)$ and using $H(t|PI) = H_0(t) e^{PI}$ gives, $$\log(H_0(t)) = γ_0 + (γ_1 - 1)PI + γ_2 e. \quad (1)$$

A formal calibration assessment (called "validation by calibration" by Van Houwelingen) involves testing the perfect calibration hypothesis, $H_0$: $γ_0=0$, $γ_1=0$, $γ_2=1$. Fitting the model (1) using survreg from the R package survival (Therneau, A Package for Survival Analysis in S. R package version 237-7 2014) gives the calibration coefficients listed in Table 6.

TABLE 6

Coefficients for Weibull calibration model applied to CVD9 for use in the validation set.
CVD9

| | Estimate | 95% CI | | p-value |
|---|---|---|---|---|
| $\hat{γ}_0$ | -0.230 | -0.4189 | -0.0412 | 0.02 |
| $\hat{γ}_1 - 1$ | -0.998 | -1.1752 | -0.8212 | 0.98 |
| $\log(\hat{γ}_2)$ | 0.149 | 0.0384 | 0.2598 | 0.008 |

The intercept ($\hat{S}_0$) and scale term ($\hat{S}_0$) indicate that CVD9 needs calibration before being applied to the validation cohort, though as discussed below the systematic intensity bias in the validation set is responsible for most of the contribution to the intercept term.

Blood samples in the HUNT3 validation set were collected using a more lenient collection protocol than in the discovery set and as a result we observed a systematic intensity bias across most of the 1054 proteins measured in the validation samples. As discussed herein, this bias was largely removed by the normalization steps, though as shown below a small residual bias remains in the signal levels for the 9 proteins used in the model CVD9. This bias is an artifact of the normalization process (validation samples have higher signal levels than discovery samples before normalization but lower signal levels after) and as shown below it is largely responsible for the estimated value of the coefficient, $\hat{S}_0$.

Figure 3:
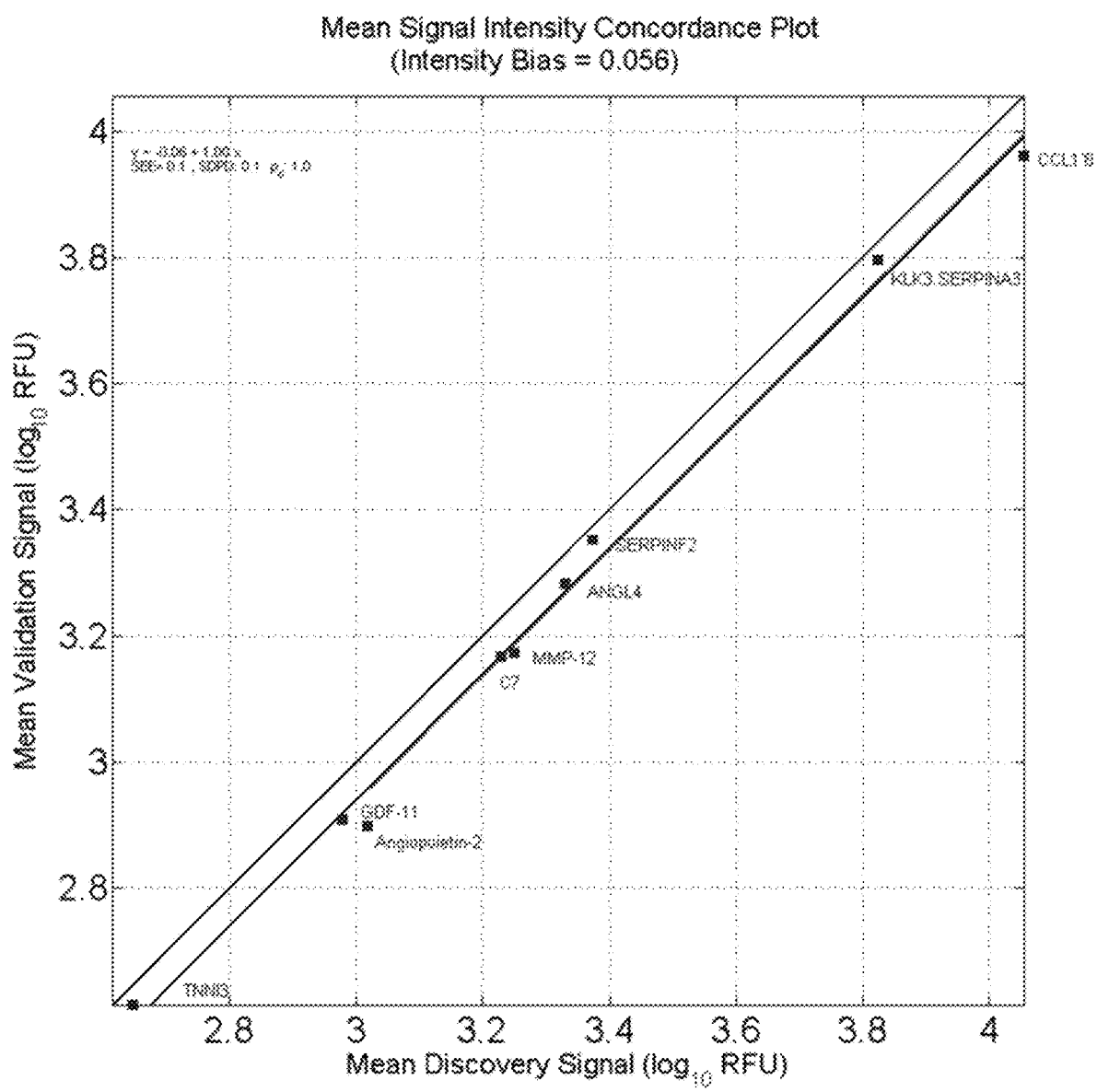
FIG. 3 shows mean signal levels of the CVD9 proteins in discovery and validation sets and robust linear regression model used to estimate residual intensity bias resulting from the normalization procedure.

The intercept of the robust regression line in FIG. 3 gives an estimate of the intensity bias common to all 9 proteins in CVD9. If we let $\Delta$ denote the estimated bias and $\beta_j$ and $\sigma_j$ be the model coefficient and population standard deviation for the $j^{th}$ protein, then applying CVD9 to the validation data results in the addition of the constant factor, $$\Delta \sum_{j=1}^{9} \frac{\beta_j}{\sigma_j}, \quad (2)$$

over what would otherwise be the contribution of the model intercept. In this manner the intensity bias in the protein signals appears as a discrepancy in the time scale of the baseline survivor function in the discovery and validation sets, precisely the term associated with the parameter $\gamma_0$ in calibration model (1). Using the estimate $\Delta=-0.056$ generated by the intercept of the robust linear regression in (2) along with the CVD9 model coefficients and population standard deviations subtracts 0.23145 from the linear predictor, almost exactly the value $(\hat{S}_0)$ estimated for the intercept in the calibration model. Thus the "residual" intensity bias remaining after the normalization procedure is largely responsible for the magnitude of $(\hat{S}_0)$ rather than an actual discrepancy between the baseline survivor functions in the discovery and validation cohorts.

The signal intensity bias in the HUNT3 sample collection is an aspect of this particular validation set that we do not expect to generalize to samples collected under more stringent collection protocols. With this in mind we assessed performance in the validation set using the re-calibrated CVD9 model described below.

When the event time distribution is Weibull with scale a and shape b, the corresponding baseline survivor function is $$Pr_{cal}[T \geq t] = e^{-(\frac{t}{a})^b},$$

which we write in terms of the cumulative baseline hazard $(H_0)$ as $\log(H_0)=b \log(t/a)$. Substituting this into the left side of equation (1), and using the calibration coefficients in Table 6, the resulting expression to generate risk scores can be put in the form of the accelerated failure time model, $$\log(t|z) = \beta_0^{cal} + \beta^{cal T} z + s^{cal} e$$

with "calibrated" model coefficients:

$$\beta_0^{cal} = \log(ae^{\frac{\gamma_0}{b}}), \beta_j^{cal} = -\frac{(\gamma_1 - 1)}{b} \beta_j^{cox}, s^{cal} = \frac{\gamma_2}{b}.$$

Using these model coefficients, the associated calibrated risk score is generated using $$Pr_{cal}[T \leq t | z] = 1 - e^{-e^{u^{cal}(z)}}, \text{ where}$$

$$u^{cal}(z) = \frac{(\log t - [\beta_0^{cal} + \beta^{cal T} z])}{(s^{cal})}.$$

The resulting prognostic index (PI) and extreme value scale factor for the re-calibrated CVD9 model used in the validation set are:

$$\{PI = -16.39 + 1.55 \times ANGPT2 - 1.22 \times GDF11 + 2.11 \times C7 -$$
$$2.64 \times SERPINF2 + 0.57 \times CCL18 + 1.02 \times ANGPTL4 +$$
$$1.43 \times KLK3 \cdot SERPINA3 + 0.72 \times MMP12 + 0.59 \times TNNI3 \ s = 0.98$$

Similar calibration models were constructed for the variants of CVD9 that include clinical variables. The resulting calibration model coefficients are listed in Table 7. As was the case for CVD9, the models that include clinical variables had the same systematic Intensity bias in the 9 proteins and together this bias generated a contribution of $-0.254$ and $-0.245$ to the $(\hat{S}_0)$ estimates in the respective calibration models.

TABLE 7

Coefficients for Weibull calibration models applied to variants of CVD9 that include clinical variables.

| | Estimate | 95% CI | | p-value |
|---|---|---|---|---|
| CVD9 + Age + Sex = "Male" | | | | |
| $\hat{\gamma}_0$ | −0.275 | −0.4633 | −0.08623 | 0.004 |
| $\hat{\gamma}_1$-1 | −1.042 | −1.2388 | −0.8460 | 0.67 |
| $\log(\hat{\gamma}_2)$ | 0.1577 | | | 0.005 |
| CVD9 + Age + Sex = "Male" + Diabetes = "Yes" + eGFR | | | | |
| $\hat{\gamma}_0$ | −0.228 | −0.4228 | −0.03383 | 0.03 |
| $\hat{\gamma}_1$-1 | −1.079 | −1.3041 | −0.8532 | 0.49 |
| $\log(\hat{\gamma}_2)$ | 0.1737 | | | 0.002 |

After identification of proteins significantly associated with cardiovascular events (after Bonferroni correction at a 5% significance level), we utilized L1 penalized (LASSO; see Tibshirani, *Stat Med.* 1997; 16:385-395) Cox regression for variable (protein) selection purposes. By virtue of simultaneously selecting variables and shrinking attendant coefficients, the LASSO yields good predictive models, as has been widely demonstrated. See Hastie et al., *Elements of statistical learning*, second ed. Springer; 2009. Such L1 penalization approaches are especially effective in high dimensional predictor settings exemplified by our 1054 proteins. To obtain a fully parametric model, we applied step-wise backward elimination to a Weibull accelerated failure time using the full set of LASSO selected proteins. This removed the 7 least important contributors and resulted in the parsimonious 9-protein model (CVD9), a fully parametric prognostic model in the spirit of Framingham.

As a respected comparative reference standard, risk predictions were generated from the Framingham secondary event risk model (D'Agostino, et al., *Am Heart J.* 2000; 139:272-281) recalibrated for use in the discovery and validation data sets, as follows.

D'Agostino presents the following accelerated failure time model for secondary cardiovascular event prediction:

$$Pr[T \leq t] = 1 - e^{-e^{\left(\frac{Log(t) - PI_{FR}}{s}\right)}},$$

where the prognostic index and scale parameter for males is

Male: $\begin{cases} PI_{FR} = 4.995 - 0.0145 \times Age - 0.6738 \times \text{Ln}\left(\frac{TotalChol}{HDL}\right) - \\ \qquad 0.3042 \times DiabetesStatus, \\ s = 0.9994 \end{cases}$ Female: $\begin{cases} PI_{FR} = 13.537 - 0.0225 \times Age - 0.834 \times \text{Ln}\left(\frac{TotalChol}{HDL}\right) - \\ 0.7829 \times DiabetesStatus - 1.3713 \times \text{Ln}(SBP) - 0.3669 \times Smoker, \\ s = 1.031 \end{cases}$ Before comparing the Framingham model to CVD9, we re-calibrated the model for use in the discovery and validation sets.

Recalibrating Framingham for Discovery and Validation Sets

To re-calibrate the Framingham secondary risk score for use in the discovery set and validation set we used a single variable Cox proportional hazard calibration (van Houwelingen, *Stat Med* 2000; 19:3401-15; Steyerberg. Clinical Prediction Models: Springer; 2010) model. Denoting the baseline survivor function by $S_0(t)$, the calibrated 4-year Framingham risk score is $$Pr_{cal}[T \leq t] = 1 - \widehat{S}_0(4) e^{\widehat{\beta}^* \times PI_{FR}}$$

where $\widehat{\beta}^*$ is the estimate from the calibration model fit to the values of the Framingham prognostic index in the particular sample set and $\widehat{S}_0(t)$ is the Kaplan-Meir estimate of the survivor function in that population. Table 8 lists the resulting calibration model coefficients.

TABLE 8

Calibration coefficients for single variable Cox proportional hazard calibration model used to re-calibrate the Framingham secondary risk for the respective discovery or validation set

| | Estimated Cox Calibration Coefficient ($\widehat{\beta}^*$) | Standard Error | p-value |
|---|---|---|---|
| Discovery | 0.472 | 0.066 | <0.001 |
| Validation | 0.396 | 0.067 | <0.001 |

Figure 4:
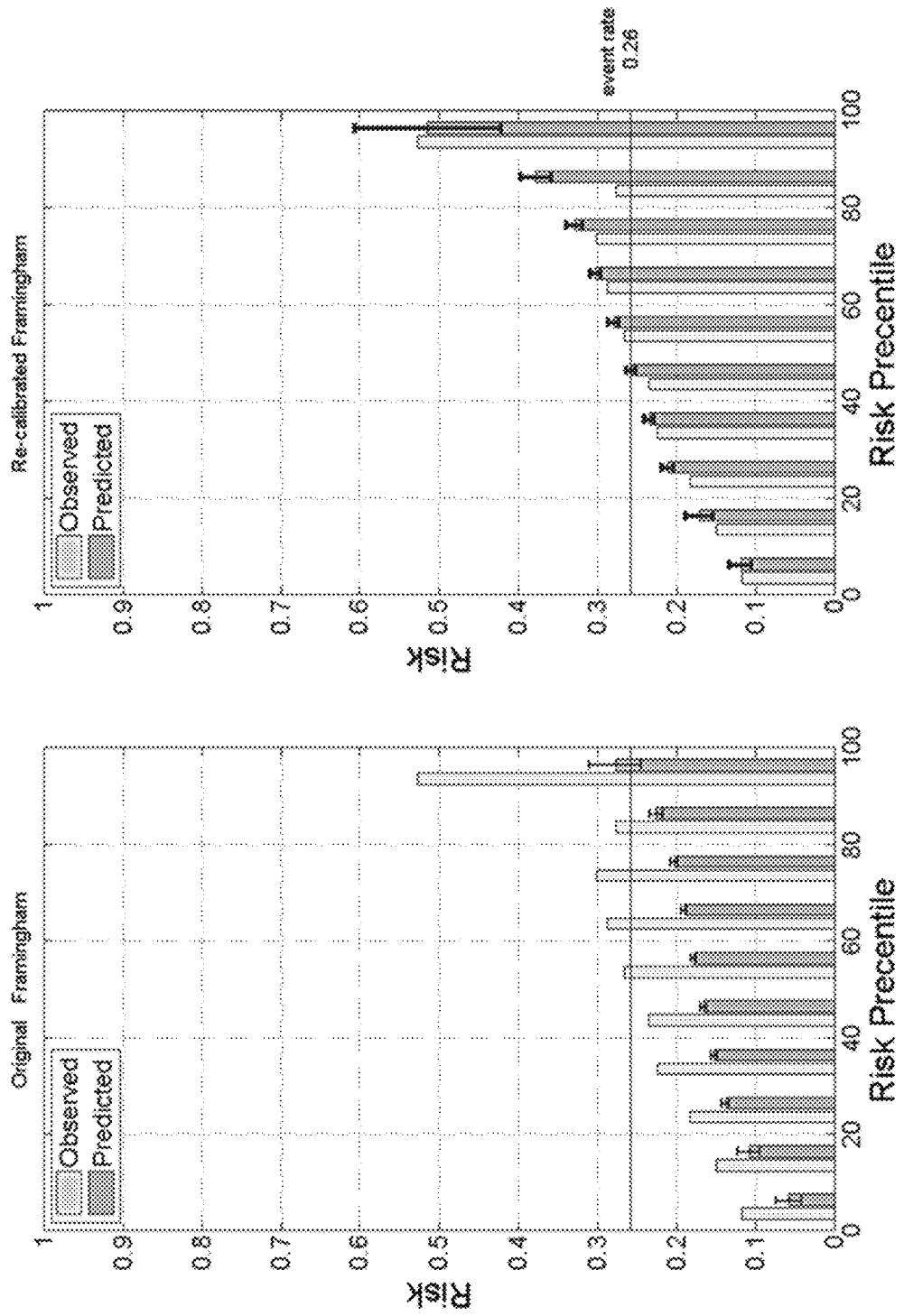
FIG. 4 shows a comparison of predicted and actual risk generated by the Framingham model in the discovery set before (left) and after (right) re-calibration with Cox calibration model.

Calibration performance was evaluated by assessing the agreement between the frequency of observed and predicted events. FIG. 4 shows the frequency of predicted and observed events for each decile of risk for the Framingham model in the discovery and FIG. 5 in the validation sets. In each case the left frame shows the original Framingham score and the right frame shows the re-calibrated score using the model with coefficients listed in Table 8.

Figure 5:
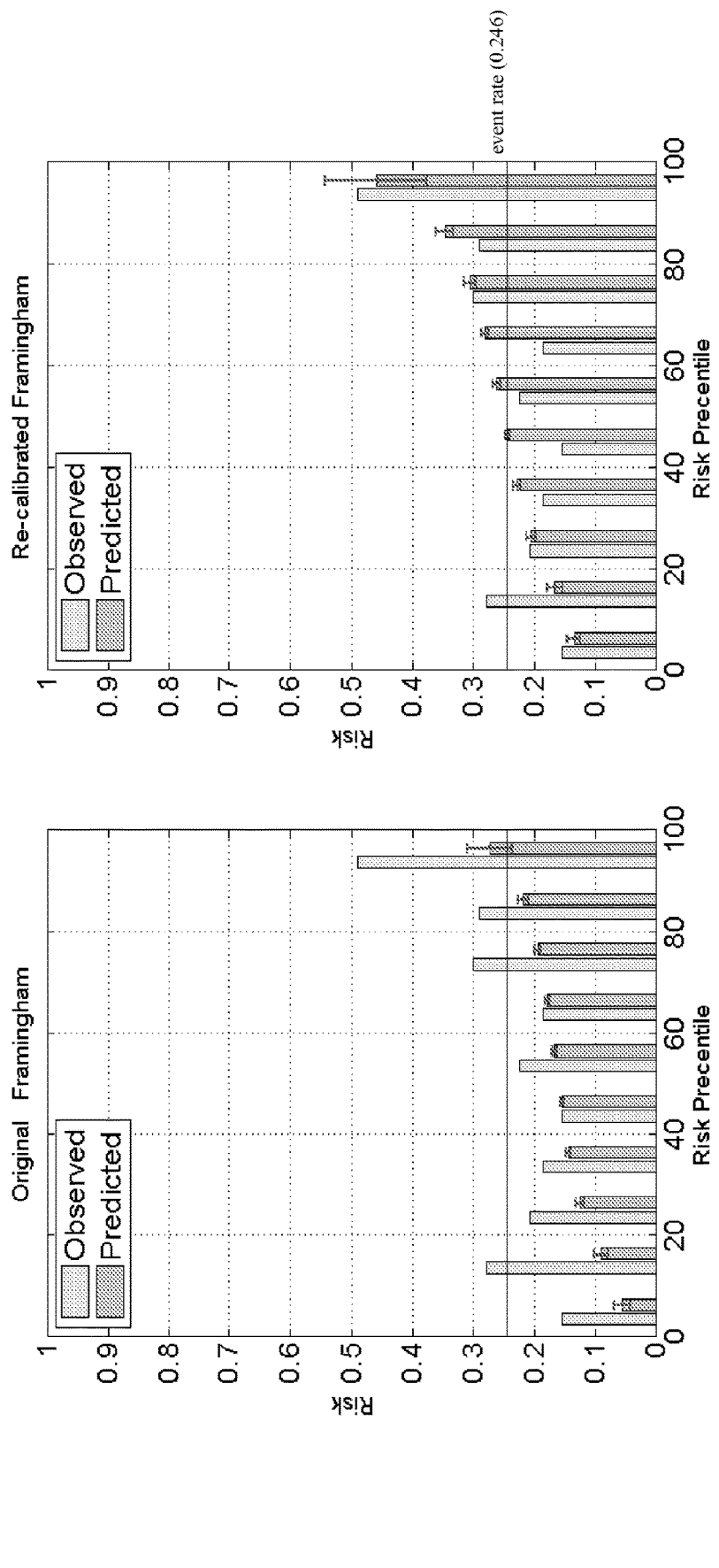
FIG. 5 shows a comparison of predicted and actual risk generated by the Framingham model in the HUNT3 validation set before (left) and after (right) re-calibration with Cox calibration model.

While calibration performance was acceptable in the discovery cohort, a similar level of agreement between predicted and observed event frequencies was not achieved in the validation cohort as can be seen in FIG. 5. We report the $\chi^2$ (Hosmer-Lemeshow) statistic to summarize the calibration performance shown graphically in FIG. 4 and FIG. 5—this statistic and associated p-value were computed with the plotCalibration function in the R package predictABLE. Kundu et al., PredictABEL: Assessment of risk prediction models. R package version 12-1 2012. The p-values of 0.70 and 0.02 for the Hosmer-Lemeshow test are consistent with good calibration of the Framingham model in the discovery and poor calibration in the validation cohort.

The entries in Table 9 summarize the discrimination and calibration performance of the re-calibrated Framingham scores in both the discovery and validation sets. As discussed in greater detail herein, we report two measures of discrimination performance, the hazard ratio between the fourth and first quartiles and the "C-statistic". For the latter concordance index we report the weighted area under the incident/dynamic ROC curve, $C^\tau$ with for $\tau=4$ years. The c-statistics are consistent with relatively poor discrimination of the Framingham model in the discovery and validation cohorts.

TABLE 9

Discrimination and Calibration Performance of re-calibrated Framingham models in the discovery and validation sets.

| | Discrimination | | | Calibration | |
|---|---|---|---|---|---|
| Data Set | $C^1$ (Year 1) | $C^4$ (Year 4) | HR Q4/Q1 | Hosmer-Lemeshow $\chi^2$ | p-value |
| Discovery | 0.620 | 0.615 | 2.8 | 5.54 | 0.70 |
| Validation | 0.616 | 0.609 | 2.3 | 18.75 | 0.02 |

Figure 6:
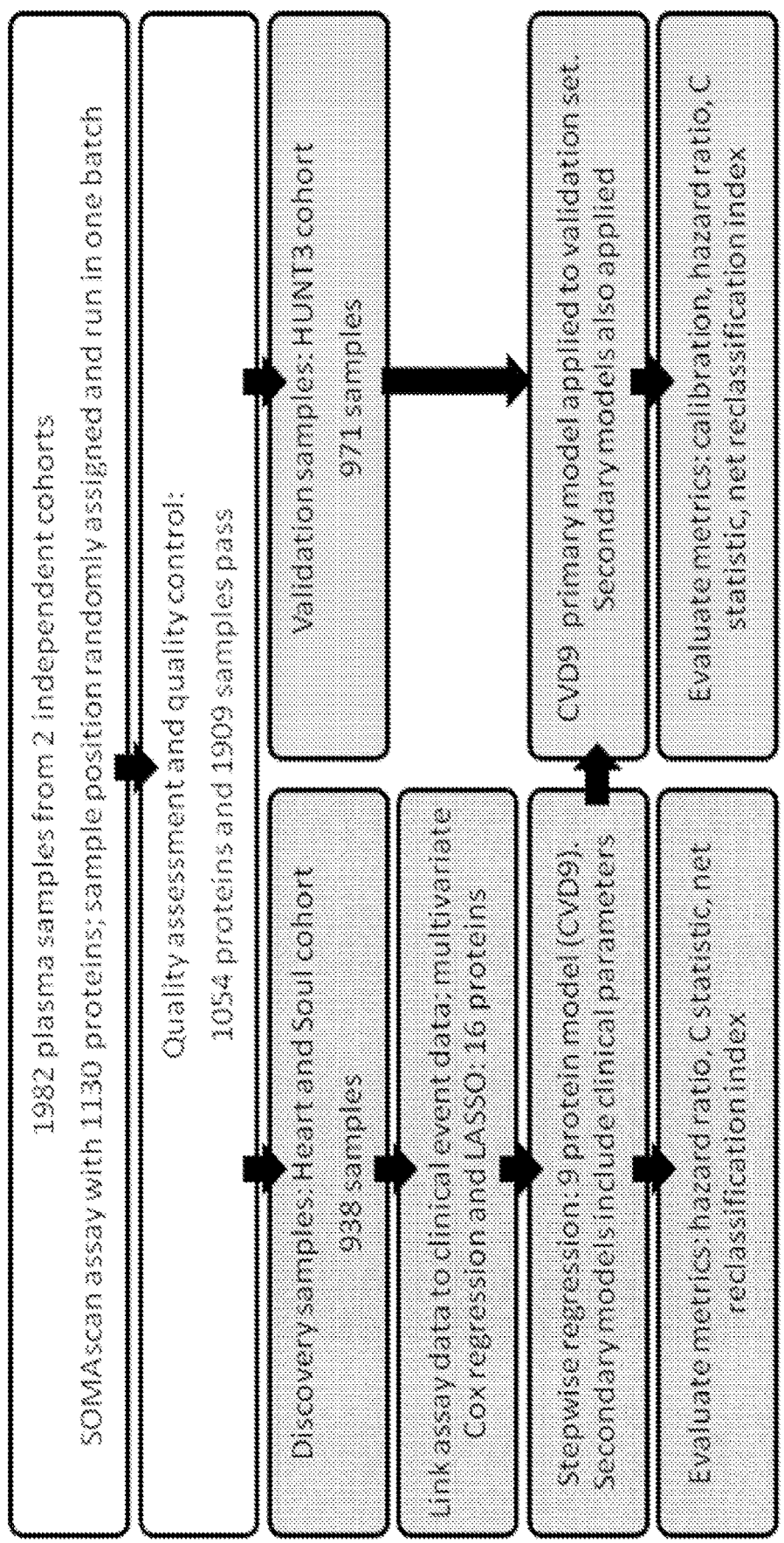
FIG. 6 shows sample and statistical process flowchart as applied to the discovery (left, gray) and validation (right, pink) sample sets.

As this score was validated for predictions up to and including 4 years, we used the four-year time interval for performance comparisons with the CVD9 protein model. We also calculated the category-free net reclassification index (NRI; Pencina et al., *Stat Med.* 2011; 30:11-21) for the CVD9 protein model vs. Framingham as discussed below. The Framingham risk score was previously validated only for predictions of MI and death but we are also predicting stroke and heart failure events. We retain the Framingham secondary event risk score as a comparator because in this study its performance is similar across all event types and because it is viewed as the most likely score of interest to the scientific community for this population. The process that generated the multi-protein cardiovascular risk prediction model and the metrics that compare it to the Framingham secondary event risk score (D'Agostino et al., *Am Heart J.* 2000; 139:272-281) are summarized in FIG. 6 and discussed below. The impact of adding commonly available clinical parameters (selected from variables that were available in both cohorts and differed between patients with events and those without) to CVD9 was also evaluated in secondary models (see above). All statistical computing was performed using the R Language for Statistical Computing. See R Core Team RFfSC, Vienna, Austria R: A language and environment for statistical computing. Manual. 2013.

Validation Performance

Figure 7:
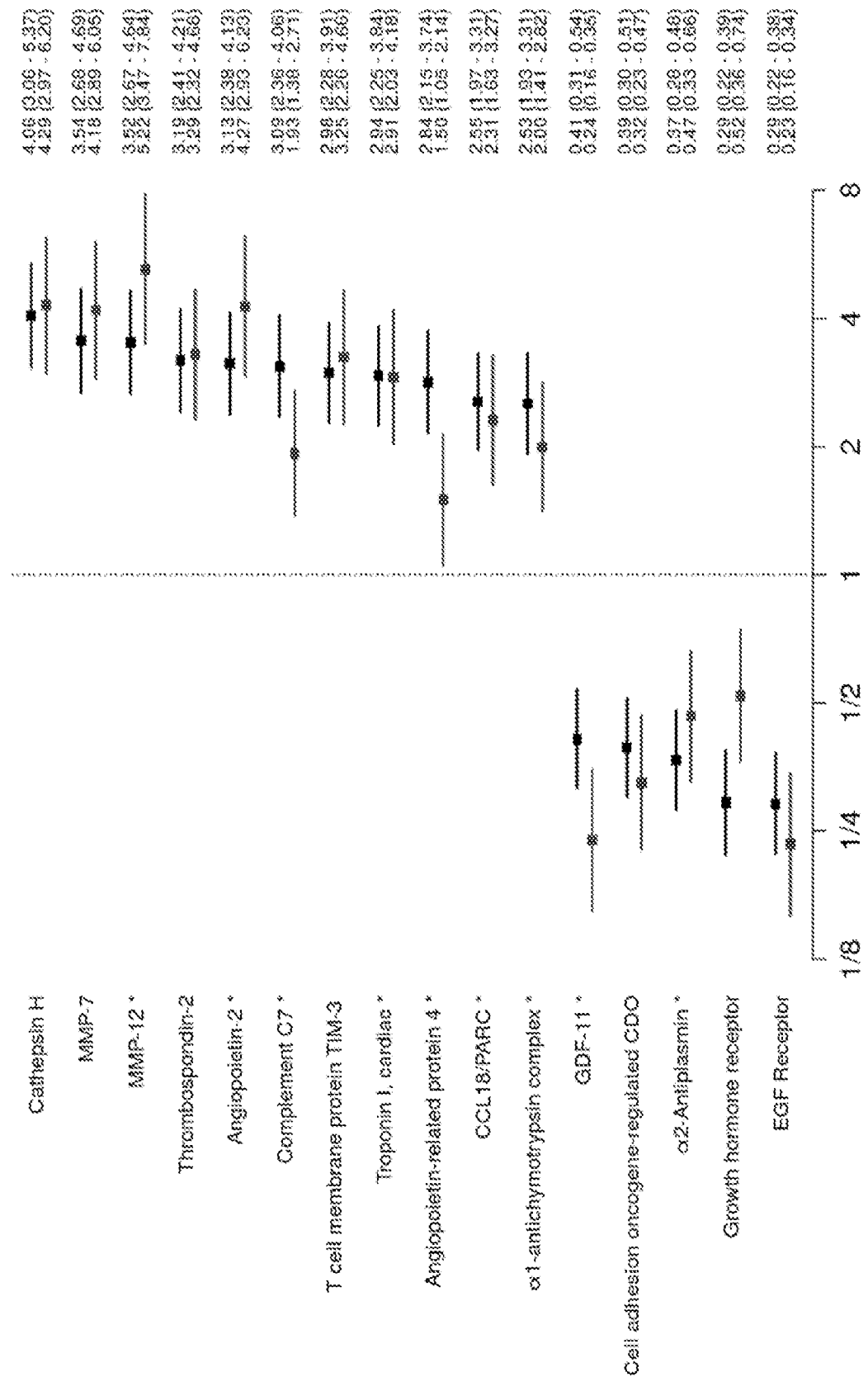
FIG. 7 shows the ratio of univariate fourth to first quartile hazard ratios (with 95% confidence intervals) for a complementary group of 16 proteins selected by the multivariate LASSO procedure in the discovery set (black symbols, top line of each pair of lines) and same proteins from the validation set (red symbols, bottom line of each pair of lines). Proteins marked with asterisks are included in the final parametric model (CVD9) after step-wise backwards elimination of the least important proteins. For relevant biological properties of these 16 proteins, see Examples. Legend: MMP-7=matrix metalloproteinase 7; MMP12=matrix metalloproteinase 12; TIM3=T-cell immunoglobulin and mucin domain-containing protein 3; CCL18=Chemokine (C—C motif) ligand 18, previously known as PARC=Pulmonary and activation-regulated chemokine; GDF=Growth differentiation factor 11; CDO=Cell adhesion associated oncogene regulated; EGF=epidermal growth factor.

The forest plot shown in FIG. 7 shows a comparison of the hazard ratios for the 16 LASSO proteins in both the discovery and validation sets. With the exception of Angiopoietin-related protein 4 and Complement C7, the hazard ratios for the individual proteins in the CVD9 model are similar in the discovery and validation sets. This is a measure of the validation performance of the individual proteins—the remainder of this section discusses the validation performance of the specific combination of those proteins that results in the model CVD9.

Calibration performance is particularly important when model predictions are used to inform clinical decisions. We first evaluated the CVD9 estimates of absolute risk in the validation population as in Steyerberg (*Epidemiology* 2010; 21:128-38) and then assessed the discrimination performance in terms of change in C-statistic and risk reclassification relative to the Framingham model.

Calibration

Figure 8:
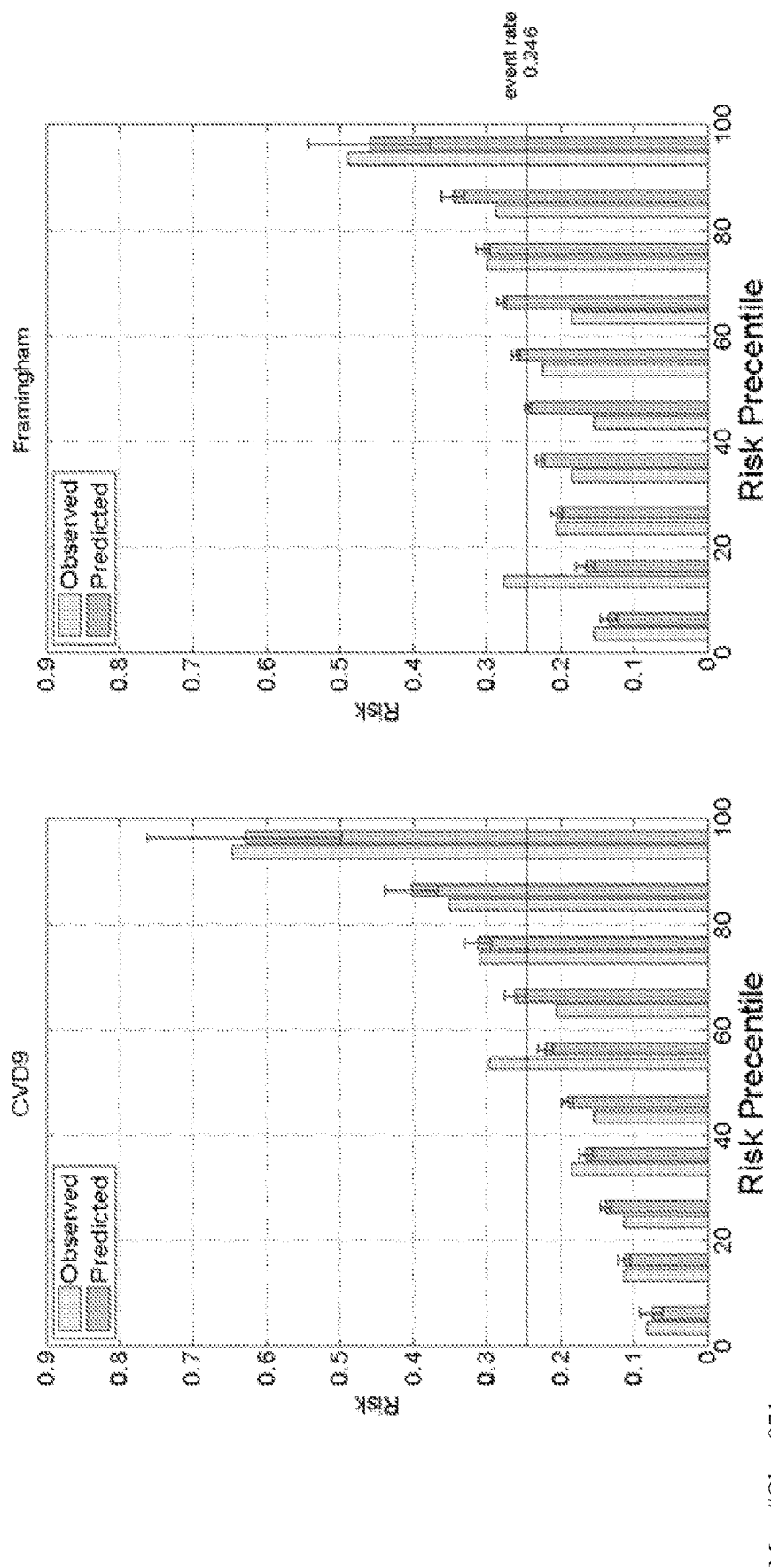
FIG. 8 shows calibration performance by decile of predicted risk in the HUNT-3 validation set for CVD9 (left) and Framingham (right).

Calibration performance was evaluated by assessing the agreement between the frequency of observed and predicted events in the four-year interval following the baseline blood sample. FIG. 8 shows the frequency of predicted and observed events for each decile of risk in the validation set for CVD9 (left) and the Framingham model (right) re-calibrated for use in the validation set.

Across the full range the predicted event frequency in a given risk decile generated by CVD9 is within 8 (and typically within 3) percent of the observed event frequency. Each right bar of each pair of bars represents roughly 100 patients and as the error bars indicate, risk scores for patients in each decile are more similar to each other than those of patients in the neighboring risk deciles. It is in this sense that we speak of "individualized" risk assessment when considering the information provided by the proteins in CVD9.

Figure 9:
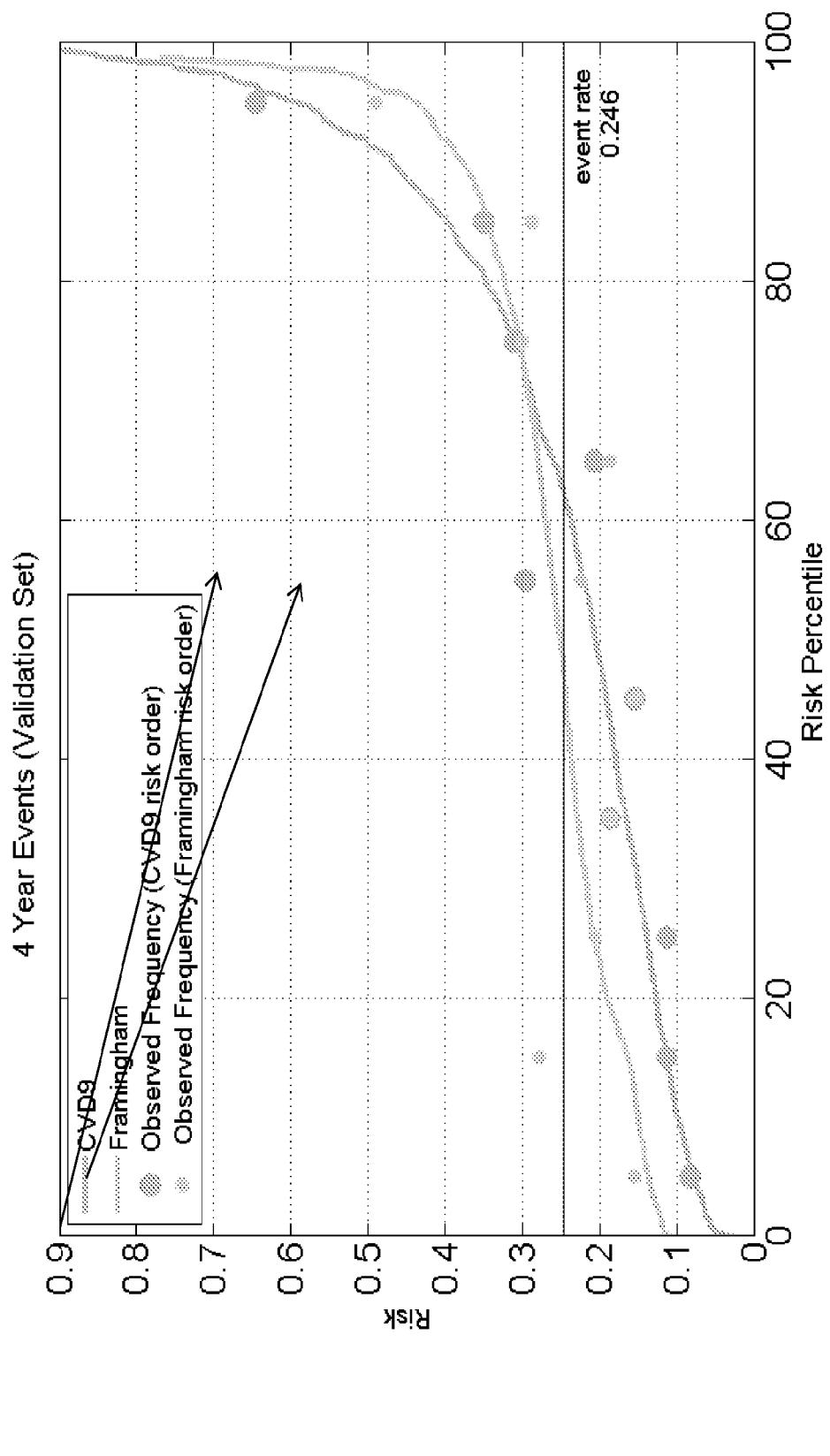
FIG. 9 shows predicted risk for CVD9 (pink) and Framingham (grey) versus percentile of CVD9 risk. Solid points indicate the observed event frequency for patients in each decile of predicted risk generated by the CVD9 (pink) and Framingham(grey) models. The horizontal line indicates the 4-year event incidence.

In general the agreement between predicted and observed event frequencies is weaker in the Framingham model (particularly for the patients in the 10-20$^{th}$ risk percentiles). FIG. 9 shows the predictiveness curves (Pepe et al., *Stat Med* 2013; 32:1467-82) for CVD9 and the Framingham score re-calibrated for use in the validation set.

With the risk scores from the two models on the same scale in FIG. 9, we see that the CVD9 model generates a more accurate representation of absolute risk than Framingham at both ends of the risk spectrum by correctly predicting the (low) risk of the subjects below the 10th percentile and the catastrophically (65%) high risk for subjects above the 90th risk percentile. In addition the slope of the predictiveness curve for CVD9 is steeper over the upper half of risk percentiles indicating that CVD9 provides a finer resolution estimate of absolute risk for the patients in each risk decile than the traditional Framingham model.

Discrimination

The entries in Table 10 summarize the discrimination performance of the CVD9 and Framingham models re-calibrated for the validation cohort. As a concordance index we report the weighted area under the incident/dynamic ROC curve, $C^\tau$, associated with the fixed follow-up interval $[0,\tau]$ (Heagerty et al., *Biometrics* 2005; 61:92-105), which is equivalent to Harrell, Pencina and D'Agostonio's "C-statistic". See, e.g., Harrell et al., *Stat Med* 1996; 15:361-87; and Pencina et al., *Stat Med* 2012; 31:1543-53. We calculated $C^\tau$ for $\tau=1$ and 4 years using the risksetAUC function in the R package riskSetROC. See Heagerty et al., risksetROC: Riskset ROC curve estimation from censored survival data. R Package version 104 2012.

TABLE 10

Discrimination and Calibration Performance Summary for CVD and Framingham models re-calibrated for use in validation cohort.

| | $C^\tau$ | | NRI | | | | | Calibration | |
|---|---|---|---|---|---|---|---|---|---|
| Model | Year 1 | Year 4 | NRI (>0) | Event | No Event | IDI | Hazard Ratio Q4/Q1 | Hosmer-Lemeshow $\chi^2$ | p-value |
| CVD9 | 0.71 (0.68-0.74) | 0.70 (0.67-0.73) | 52% (37-67%) | 18% (5-31%) | 34% (26-41%) | 0.10 (0.07-0.13) | 6.0 | 7.90 | 0.44 |
| CVD9 + Age + Male | 0.69 (0.66, 0.73) | 0.68 (0.65, 0.71) | 41% (27-55%) | 16% (3-29%) | 26% (19-33%) | 0.08 (0.05-0.12) | 4.9 | 1.51 | 0.99 |
| CVD9 + Age + Male + Diabetes + eGFR | 0.67 (0.64-0.71) | 0.65 (0.63-0.69) | 35% (22-51%) | 11% (1-25%) | 24% (18-30%) | 0.07 (0.04-0.09) | 4.6 | 9.99 | 0.266 |
| Framingham | 0.616 (0.58-0.66) | 0.609 (0.58, 0.64) | — | — | — | 0.02 | 2.3 | 18.75 | 0.02 |

ROC Curves

Figure 10:
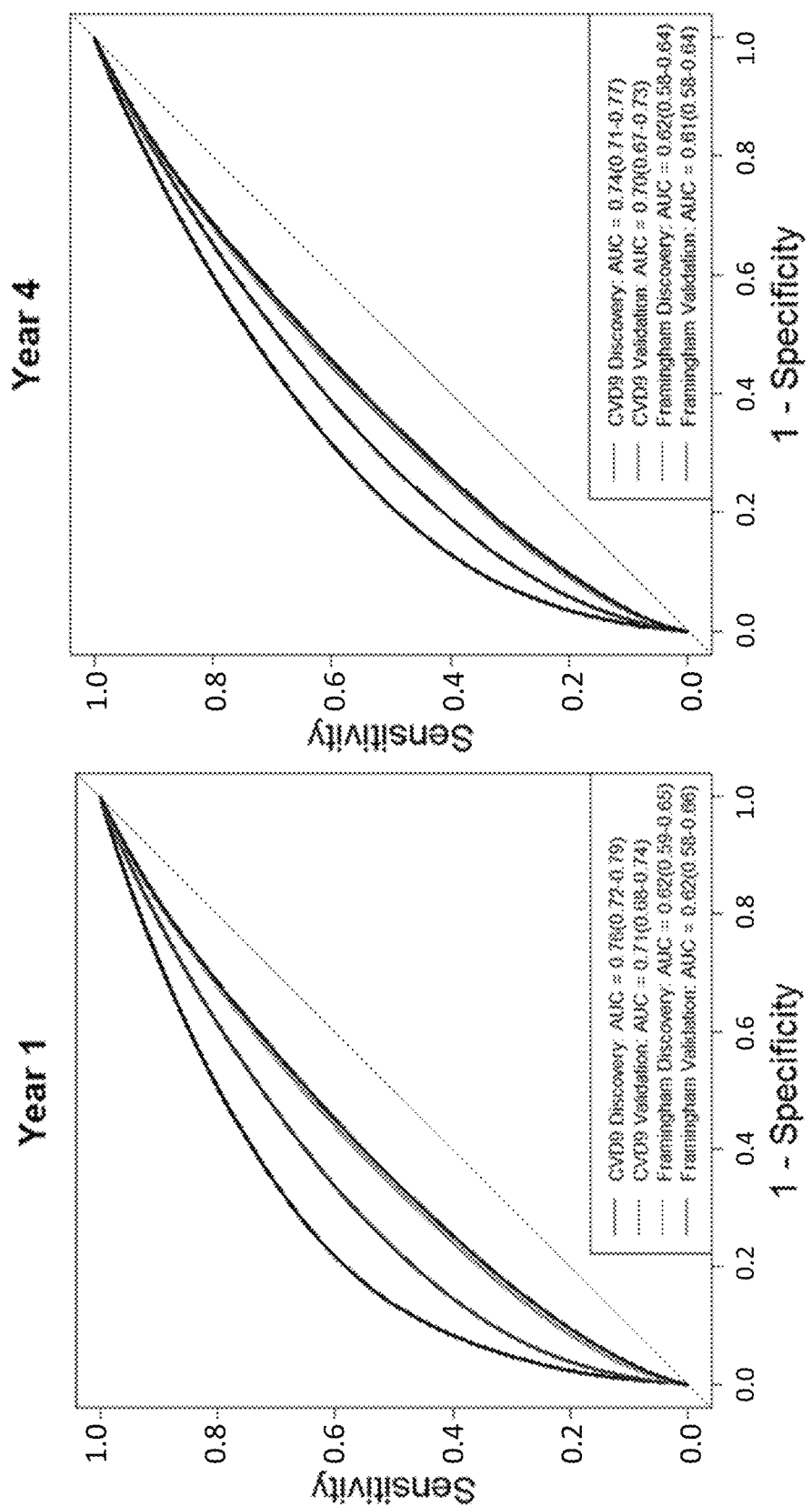
FIG. 10 shows ROC curves for model applied to the discovery set (black, indicated by arrow) and independent validation set (red, indicated by arrow) at year 1 and year 4, the maximum valid time for the Framingham score in this population. Also included are the ROC curves for the Framingham score in the discovery (green) and validation (blue) cohort.

FIG. 10 shows ROC curves for the CVD9 and Framingham models generated with the riskSetROC package for both the discovery and validation sets. We generated ROC curves at years one and four for each model.

Risk Reclassification

Four-year event probabilities were generated with CVD9 and the Framingham secondary model with the latter re-calibrated for use in the discovery set. The category free net reclassification index[19] NRI(>0), was calculated using the R package nricens. See Eisuke. NRI for risk prediction models with time to event and binary response data. R package version 12 2013.

Table 11 lists the terms in NRI(>0) and the reclassification probabilities comparing CVD9 to Framingham in both the discovery and validation sets. Confidence intervals reported are empirical 95% intervals computed with 100 bootstrap samples. Both CVD9 and the Framingham model were re-calibrated for use in the validation set prior to this computation.

TABLE 11

Net Reclassification Indices and reclassification probabilities
for CVD9 compared to the Framingham model in the discovery set.

|  | Discovery | | | Validation | | |
|---|---|---|---|---|---|---|
|  | Point Estimate | 95% CI lower | 95% CI Upper | Point Estimate | 95% CI lower | 95% CI Upper |
| NRI (>0) | 0.57 | 0.43 | 0.71 | 0.52 | 0.38 | 0.67 |
| Event NRI | 0.16 | 0.04 | 0.29 | 0.18 | 0.06 | 0.31 |
| No Event NRI | 0.41 | 0.34 | 0.47 | 0.34 | 0.27 | 0.41 |
| Pr (Risk Up\|Event) | 0.58 | 0.52 | 0.64 | 0.59 | 0.53 | 0.65 |
| Pr (Risk Down\|Event) | 0.42 | 0.36 | 0.48 | 0.41 | 0.35 | 0.47 |
| Pr(Risk Down\| noEvent) | 0.71 | 0.67 | 0.74 | 0.67 | 0.63 | 0.70 |
| Pr(Risk Up\| noEvent) | 0.29 | 0.26 | 0.33 | 0.33 | 0.30 | 0.37 |

Example 3. Results

Baseline Characteristics

The clinical characteristics of the two study populations at baseline are summarized in Table 12. As expected, known risk factors are significantly more prevalent in the groups with events. There were fewer overall events in HUNT3 than in Heart and Soul, due to shorter follow up; nonetheless, the populations were generally comparable in the event rates per unit time and the distribution of the event types. In Table 12, P-values are associated with Fisher's exact test for categorical covariates and the Mann-Whitney U test for continuous covariates. Continuous values summarized with median and inter-quartile range (IQR). The HUNT3 validation set was not designed as a CHD study and as a result some clinical information was not available and is marked N/A. Legends: BMI=body mass index; ACE=angiotensin converting enzyme; ARB=angiotensin receptor blocker; LDL-C=low density lipoprotein cholesterol; HDL-C=high density lipoprotein cholesterol; TG=triglycerides; eGFR=estimated glomerular filtration rate.

TABLE 12

Study population baseline characteristics

| | Discovery Set (Heart and Soul) | | | Validation Set (HUNT3) | | |
|---|---|---|---|---|---|---|
| Event Summary | No Event (10 years) | Event (10 years) | P-value | No Event (5 years) | Event (5 years) | P-value |
| # Subjects | 473 | 465 | | 699 | 272 | |
| Demographic Variables: median (inter-quartile range) | | | | | | |
| Age (years) | 64.0 (57.0-71.0) | 71.0 (63.0-78.0) | <0.001 | 67.6 (60.0-75.3) | 75.9 (67.9-81.0) | <0.001 |
| Male (%) | 361 (76.3) | 412 (88.6) | <0.001 | 508 (72.7) | 192 (70.6) | <0.001 |
| Caucasian (%) | 275 (58.1) | 290 (62.5) | 0.18 | NA | NA | NA |
| Diabetes (%) | 96 (20.3) | 151 (32.6) | <0.001 | 84 (12.0) | 49 (18.0) | 0.02 |
| Smoking, current (%) | 88 (18.6) | 96 (20.7) | 0.46 | 142 (20.3) | 56 (20.6) | 0.93 |
| BMI (kg/m$^2$) | 28.2 (25.2-31.6) | 27.1 (24.4-30.5) | <0.001 | 27.9 (25.8-30.7) | 28.0 (25.3-30.8) | 0.89 |
| Cardiovascular Medications | | | | | | |
| Statin (%) | 275 (58.1) | 290 (62.5) | 0.17 | NA | NA | NA |
| ACE/ARB (%) | 89 (23.5) | 89 (39.9) | <0.001 | NA | NA | NA |
| Beta-blocker (%) | 88 (18.6) | 96 (20.7) | 0.69 | NA | NA | NA |
| Aspirin (%) | 28.2 (25.2-31.6) | 27.1 (24.4-30.5) | 0.26 | NA | NA | NA |
| Laboratory Tests | | | | | | |
| LDL-C (mg/dL) | 98.0 (83.0-121) | 100 (81.2-124.0) | 0.76 | NA | NA | NA |
| HDL-C (mg/dL) | 44 (36-54) | 42 (35-52) | 0.044 | 46.4 (38.7-54.1) | 42.5 (34.8-50.3) | 0.002 |
| Total Cholesterol (mg/dL) | 174 (152-196) | 169 (146-201) | 0.29 | 174 (151-197) | 178 (147-209) | 0.32 |
| TG (mg/dL) | 110.0 (74.8-169) | 111.0 (74.0-163.0) | 0.78 | 142.0 (106.9-195.0) | 142.0 (106.0, 195.0) | 0.22 |
| eGFR[3] (mL/min) | 78.2 (65.3-91.9) | 65.8 (52.3-82.7) | <0.001 | 70.9 (58.5-82.9) | 60.3 (46.7-73.6) | <0.001 |
| Creatinine (mg/dL) | 1.0 (0.8-1.1) | 1.1 (0.9-1.3) | <0.001 | 1.0 (0.9-1.1) | 1.1 (0.9-1.3) | <0.001 |

[1]CKD-EPI 2009 in the Validation Set and CKD-EPI 2012 in discovery set where possible with CKD-EPI 2009 when missing values prevented computation of the 2012 formula.
[3]CKD-EPI 2009 in the Validation Set and CKD-EPI 2012 in discovery set where possible with CKD-EPI 2009 when missing values prevented computation of the 2012 formula.

Proteins Related to Cardiovascular (CV) Risk

At a 5% Bonferroni corrected significance level, univariate Cox regression analysis revealed that 117 of the 1054 proteins that passed quality control were associated with increased risk of cardiovascular events and also had univariate fourth to first quartile hazard ratios of >1.25 or <0.75 (these 117 proteins are listed in Table 14 below). Some of these proteins were correlated, suggesting the presence of far fewer than 117 distinct biologic processes; the biology of these proteins will be the target of further analysis. The hazard ratios for the 16 proteins selected from this list by the LASSO process and the subset of 9 proteins chosen for the final CVD9 model are shown in FIG. 7. The relevant biological properties of the LASSO-selected 16 proteins are summarized below.

The biomarkers identified in this analysis not only serve to derive a powerful cardiovascular risk prediction model, but also inform understanding of the biology of cardiovascular disease (CVD) and identify potential drug targets and treatment options. Below, we give a brief description of the known function(s) of the 16 proteins selected by LASSO into the CV risk prediction model.

Growth and Remodeling

Growth Differentiation Factor 11 (GDF11) is an example of biological discovery using unbiased proteomics assay tool with findings of potential clinical significance. Using SOMAscan, Lee and colleagues pinpointed age-related loss of GDF11 as the cause of age-related cardiac hypertrophy in mice. See Loffredo et al., *Cell* 2013; 153:828-39. GDF11 is now under active investigation for its role in suppressing cardiac hypertrophy and diastolic heart failure in humans. See, e.g., Olson et al., *Journal of the American College of Cardiology* 2014; 63:A780. Interestingly, while GFD-11 concentrations are reduced with increasing cardiovascular event risk in our study, an inhibitor of GDF11 activity, Follistatin-like 3 is positively associated with increasing cardiovascular risk (see Table 14).

Epidermal Growth Factor (EGF) receptor (EGFR) is expressed on monocytes and macrophages in atherosclerotic lesions. Activation by ligand binding stimulates cellular proliferation and chemotaxis. Dreux et al., Atherosclerosis 2006; 186:38-53. Evidence from animal studies shows EGF receptor protects against cardiac hypertrophy and supports appropriate vascular wall architecture and vessel reactivity. Schreier et al, *Hypertension* 2013; 61:333-40.

Soluble forms of the Growth hormone receptor (GHR) and the epidermal growth factors can serve as both reservoirs and inhibitors of the circulating factors involved in mitogenesis, cell function, and have well-known roles in cancer. Interestingly, growth hormone receptor signaling, via stimulation of its anabolic mediator Insulin-like growth factor I, has already been shown to have a negative correlation with risk of developing coronary artery disease. Juul et al., *Circulation* 2002; 106:939-44.

Angiopoietin-2 (ANGPT2), which antagonizes Angiopoietin-1 activity on the Tyrosine-protein kinase receptor Tie-2 receptor and acts in concert with Angiopoietin-1 during angiogenesis, promotes relaxation of cell-matrix contacts and may induce endothelial cell apoptosis and vessel disruption during angiogenesis[26]. Maisonpierre et al., *Science* 1997; 277:55-60. A member of the same gene family, Angiopoietin-related Protein 4 (ANGPTL4) is induced by hypoxia and not only affects vascular function and matrix-endothelial cell interaction, but also lipid metabolism as a potent inhibitor of lipoprotein lipase[27]. Li et al., *Current opinion in lipidology* 2006; 17:152-6.

Controlled interactions of the extracellular matrix and cells are vital for normal organ physiology, during normal development, in response to vascular and myocardial injury, and during cancer metastasis. Matrix metalloproteinases and their inhibitors have several targets in the vascular extracellular matrix and have been associated with atherosclerotic plaque stability, aneurysm formation and other cardiovascular diseases. Dollery et al., *Cardiovascular research* 2006; 69:625-35. Matrix metalloproteinase (MMP)-7 and MMP12 are represented in our predictive model, while the TIMP1 also has significant association with cardiovascular risk (see Table 14). Thrombospondin-2 (THBS2) mediates vascular and cardiac cell-cell and cell-matrix interactions and has been implicated in the regulation of angiogenesis, thrombosis, and inflammation. Increased serum Thrombospondin-2 concentration is associated with the risk of cardiac mortality in older men. Golledge et al., *The American journal of cardiology* 2013; 111:1800-4. Cell adhesion oncogene-related CDO (CDON) is a cell surface protein member of the Ig/fibronectin superfamily involved in myogenesis and muscle cell adhesion. Tenzen et al., *Developmental cell* 2006; 10:647-56. Its role in cell-cell interaction has been noted in tumor invasiveness but little is known about its relationship to the cardiovascular system.

Inflammation

Representing the complex roles of inflammation and immunity in cardiovascular disease, our model incorporates the inflammatory chemokine Chemokine (C—C motif) ligand 18, previously known as Pulmonary and activation-regulated chemokine CCL18/PARC, which is a monocyte/macrophage-elaborated chemokine that appears to be involved in the recruitment of T cells. Chenivesse et al., *J Immunol* 2012; 189:128-37. Plasma levels of CCL18/PARC are elevated during episodes of unstable angina and have also been found to predict CV events in patients with stable angina. De Sutter et al., *Journal of molecular and cellular cardiology* 2010; 49:894-6. The T-cell immunoglobulin and mucin domain-containing protein 3 (TIM-3) is involved in macrophage activation and other immune system activities. Anderson, *Expert opinion on therapeutic targets* 2007; 11:1005-9

Complement C7 (C7) is one of the 5 components that form the bioactive terminal complement complex (TCC). TCC deposited on endothelial cells results in cell proliferation, release of growth factors and inflammatory cytokines, and increased expression of tissue factor. TCC also stimulates proliferation of smooth muscle cells in atherosclerotic plaques. Speidl et al., *JTH* 2011; 9:428-40. In patients with symptomatic heart failure elevated serum soluble TCC predicts adverse outcome (death, urgent heart transplantation, or hospitalization with worsening heart failure). Clark et al., *Am Heart J* 2001; 141:684-90. Complement C9, another member of TCC, is also elevated in our study (Table 14).

Proteases

α1-antichymotrypsin complex (SERPINA3) complex represents the bound form of the protease inhibiter α1-antichymotrypsin which has several biological substrates. It can modulate multiple acute and chronic disease processes including blood pressure. Tang et al., *Clin Exp Hypertens* 2008; 30:648-61. α2-Antiplasmin (SERPINF2) is a serine protease inhibitor (SERPIN) that inactivates plasmin and thus reduces fibrinolysis. Matsuno et al., *Journal of thrombosis and haemostasis: JTH* 2003; 1:1734-9; Mutch et al., *JTH* 2007; 5:812-7. Cathepsin H (CTSH) is a lysosomal cysteine proteinase important in the degradation of lysosomal proteins[39]. Cheng et al., *Circulation* 2012; 125:1551-

62. However, its relationship to CV disease until our present study has been uncertain. Lutgens et al., *FASEB J.* 2007; 21:3029-41.

Myocardial Necrosis Marker

Unlike many of the aforementioned proteins that are potentially involved in causal pathways of cardiovascular diseases, Troponin I is a well-established marker of cardiomyocyte necrosis and of cardiovascular risk.

Applying the CVD9 Risk Model

Figure 11:
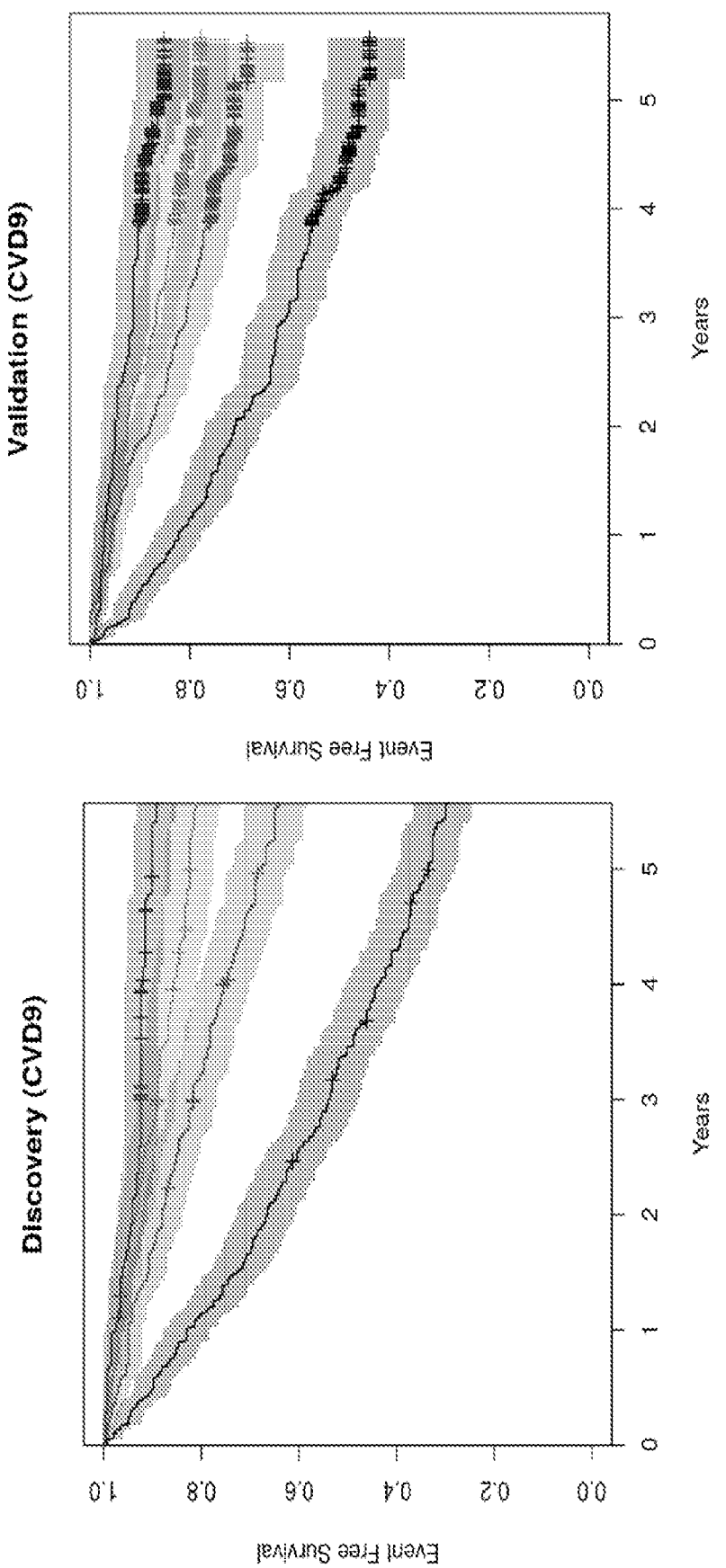
FIG. 11 shows Kaplan-Meier survival curves for each CVD9-predicted risk quartile in the discovery (left) and validation (right) cohorts. Tick marks show the time of censoring (last observation) for individual subjects and shaded intervals indicate 95% confidence intervals.

CVD9 risk was calculated for each subject, divided into quartiles and the resulting 5-year event-free survival curves are shown in FIG. 11. The Q4/Q1 hazard ratios for CVD9 are 8.2 in the discovery set and 6.0 in the validation set; for the Framingham secondary risk score (re-calibrated for use in these populations) the Q4/Q1 hazard ratio is 2.8 in the discovery cohort and 2.3 for the validation cohort.

We also evaluated the comparative performance of CVD9 vs. Framingham models using the net reclassification index and C-statistic at 1 year (a time point recommended by a National Heart, Lung and Blood Institute Working Group; see Eagle et al., *Circulation.* 2010; 121:1447-1454) and at the maximum validated time horizon of 4 years for the Framingham model. See D'Agostino et al., *Am Heart J.* 2000; 139:272-281. As shown in Table 13, the CVD9 risk prediction model delivers substantial improvements in discrimination, evidenced by increases in the C-statistic of 0.14/0.09 and a category-free NRI of 0.57/0.54 in discovery/validation cohorts respectively. There is good agreement for the CVD9 model between observed and predicted event rates (calibration) in the validation cohort. The addition of commonly available clinical and demographic parameters (age, sex, diabetes, and estimated glomerular filtration rate) made no meaningful improvement to the CVD9 model (Table 13). The comparative performance data for all the models is shown in Table 13. In Table 2, NRI (>0)=category free net reclassification index, eGFR=estimated glomerular filtration rate.

TABLE 13

Comparative performance of CVD9 model and Framingham model

|  | Framingham Secondary | Protein only (CVD9) | CVD9 + Age + Sex | CVD9 + Age + Sex + Diabetes + eGFR |
|---|---|---|---|---|
| All metrics shown in the format: discovery/validation | | | | |
| 1 year C-statistic | 0.62/0.62 | 0.76/0.71 | 0.76/0.69 | 0.77/0.67 |
| 4 year C-statistic | 0.62/0.61 | 0.74/0.70 | 0.75/0.68 | 0.75/0.65 |
| 4 year NRI(>0) vs. Framingham | | 0.57/0.52 | 0.64/0.41 | 0.67/0.35 |
| Event NRI vs. Framingham | | 0.16/0.18 | 0.19/0.16 | 0.20/0.11 |
| No Event NRI vs. Framingham | | 0.41/0.34 | 0.45/0.26 | 0.47/0.24 |
| Hazard Ratio Q4/Q1 | 2.8/2.3 | 8.2/6.0 | 10.0/4.9 | 10.3/4.6 |

Example 4: Discussion

In this study, we sought to improve the prediction of cardiovascular outcomes, particularly in the near-term, by using biomarker discovery in the largest proteomic analysis conducted to date. We used modified aptamer technology to analyze 1130 plasma proteins in the discovery cohort of 938 patients with stable CHD and validated the findings in an independent cohort of 971 patients. In the discovery cohort, we found 117 proteins prognostic of the composite cardiovascular end-point with hazard ratios greater than 25% from unity (Table 14). From these, we constructed a multivariable model consisting of 9 proteins (CVD9) whose performance was superior to that of traditional risk factors or blood biomarkers described in the literature (see, e.g., Eagle et al., *Circulation.* 2010; 121:1447-1454; D'Agostino et al., *Am Heart J.* 2000; 139:272-281; and Pearson et al., *Circulation.* 2003; 107:499-511), showing the potential advantages of broad-based proteomics compared to candidate-based approaches. The individual biomarker proteins and the CVD9 model replicated well in the validation cohort, despite the lower blood sample quality consistent with typical clinical practice.

The proper application of preventive and therapeutic strategies relies on risk classification system that allows health care professionals to target the most intensive treatments to the highest-risk individuals. See Eagle et al., *Circulation.* 2010; 121:1447-1454. Commonly used approaches rely on risk assessments based on traditional risk factors and have limitations. Many of these risk factors are chronic or even fixed, unmodifiable conditions such as sex, race, advancing age or family history. Not surprisingly, they are far better suited to predict long-term (10 years) or lifetime risk than near-term risk. Traditional risk factors predict secondary events particularly poorly in subjects with prevalent CHD. Identifying patients at near-term high risk of cardiovascular events represents an important unmet need, as it would pinpoint individuals in most urgent need of cardiovascular prevention, intervention and compliance with prescribed treatments.

Several "omics" technologies have been proposed to complement traditional risk factors in cardiovascular risk assessment. See, e.g., McShane et al., *Nature.* 2013; 502: 317-320. Among them, genomic risk scores have been investigated most extensively. Genomic approaches based on common single nucleotide polymorphisms have failed to improve risk discrimination or reclassification over traditional risk factors, judged by the same metrics that were favorably impacted by the CVD9 proteomic score in the present study (c-statistic and net reclassification). See, e.g., Paynter et al., *JAMA.* 2010; 303:631-637; Ripatti et al., *Lancet.* 2010; 376:1393-1400. Even if genomic approaches are ultimately successful, it will be in predicting long-term risk rather than near-term risk as genetic risk factors do not change over time and exert their effect through life-long exposures. Compared to genomics, proteomics offers several potential advantages. Proteomics integrate environmental and genetic influences, proteins levels can change over time, reflecting the benefits or harms of treatments or lifestyle changes and proteins are often in the causal pathways of diseases and thus potential targets of therapies. See, e.g., Nissen et al., *N Engl J Med.* 2005; 352:29-38; Ridker et al., *Lancet.* 2009; 373:1175-1182; and Stein et al., *N Engl J Med.* 2012; 366:1108-1118.

We used a novel proteomic platform consisting of modified aptamers to measure 1130 proteins in a small volume (<100 μl) of plasma. We discovered 117 candidate protein biomarkers of cardiovascular risk (Table 14). Remarkably, many of these proteins have not been reported previously as biomarkers of cardiovascular risk. From these proteins we constructed a parsimonious fully parametric model using a statistical (LASSO in conjunction with backward elimination) rather than biological approach. In this process some proteins with reasonable hazard ratios are left out (CRP, for example) as they convey information that is captured by proteins already in the model while other proteins with lower univariate hazard ratios are retained due to unique information they provide. The biologic functions of the LASSO selected proteins are discussed herein.

The CVD9 protein risk score performed better than the Framingham secondary risk score (D'Agostino et al., *Am Heart J.* 2000; 139:272-281), which relies on traditional risk factors. Including clinical variables that were significantly different in the event population such as, age, sex, diabetes or estimated glomerular filtration rate (eGFR) in secondary models provided only modest improvements in CVD9 in the inter-quartile hazard ratios and net reclassification indices in the discovery cohort (Table 13). It is possible that CVD9 already encapsulates the biology underlying the risk associated with the traditional risk factors, though we are not proposing that assessment of proteins with CVD9 or similar models replace them, as the latter might still be a better indicator of long-term risk and a specific target of treatments. Yet, CVD9 proteins levels provide a superior individualized assessment of near-term cardiovascular risk than Framingham particularly for patients at the extremes of risk (FIGS. 6 and 7), presumably because they indicate whether pathways associated with cardiovascular complications have been activated and whether end-organ damage has occurred (e.g. troponin; see Beatty et al., *JAMA Intern Med.* 2013; 173:763-769).

Our study is the first large-scale proteomic analysis of cardiovascular risk, using a high throughput, large-scale proteomic platform. This approach resulted in the discovery of numerous novel individual protein biomarkers and led to the construction of a robust multi-variable risk prediction model with superior performance for predicting near-term risk of secondary cardiovascular events. The study was conducted in two large, well-characterized cohorts with excellent adjudication of outcome events, across two continents. The US National Cancer Institute, in collaboration with an expert panel of scientists, has developed a checklist of criteria that can be used to determine the readiness of omics-based technologies for guiding patient care in clinical trials. Specimen quality was noted as an important reason why omics findings reported from one laboratory may not replicate in others. Accordingly, we have conducted our proteomic analysis across a range of specimen qualities, representative of academic institutions (Heart and Soul) and clinical practice standards (HUNT3) and our findings are robust across this range of specimen quality.

We have purposefully focused our initial investigation on a population of high-risk subjects with established coronary heart disease (CHD). There is additional need for accurate cardiovascular risk prediction in the lower risk general population or in even higher risk individuals with CHD. These studies are currently underway with other cohorts. Another limitation is that there are many more proteins in blood than the 1130 we quantified. We do not yet know if their assessment would improve cardiovascular risk assessment as they might be in the same pathways and thus redundant with the proteins we already assessed. Studies that evaluate an even larger number of proteins than reported in the present study are underway as well.

In summary, we have successfully conducted the largest proteomic study of cardiovascular risk to date, with over 2 million individual protein measurements, identified numerous new biomarkers of risk and demonstrated a risk prediction model with superior and robust performance.

TABLE 14

Table of individual proteins associated with cardiovascular risk. Biomarkers in the CVD9 panel are in bold. If the hazard ratio (HR) is greater than 1, increased levels of the biomarker are associated with increased risk; if the HR is less than 1, decreased levels of the biomarker are associated with increased risk.

| Target | UniProt ID | Q4/Q1 HR | HR per standard deviation | P value for continuous HR |
|---|---|---|---|---|
| Angiopoietin-2 | O15123 | 3.13 | 1.67 | <1e−16 |
| MMP12 | P39900 | 3.52 | 1.65 | <1e−16 |
| T cell membrane protein TIM-3 | Q8TDQ0 | 2.98 | 1.61 | <1e−16 |
| Insulin-like growth factor-binding protein 2 | P18065 | 2.93 | 1.58 | <1e−16 |
| TNF R-II | P20333 | 3.33 | 1.56 | <1e−16 |
| Follistatin-like 3 | O95633 | 3.52 | 1.56 | <1e−16 |
| Hemofiltrate CC chemokine 1 | Q16627 | 2.63 | 1.55 | <1e−16 |
| β 2-Microglobulin | P61769 | 3.58 | 1.54 | <1e−16 |
| Thrombospondin-2 | P35442 | 3.19 | 1.54 | <1e−16 |
| MMP-7 | P09237 | 3.54 | 1.53 | <1e−16 |
| Endostatin | P39060 | 2.45 | 1.52 | <1e−16 |
| Cathepsin H | P09668 | 4.06 | 1.52 | <1e−16 |
| EPH receptor B2 | P29323 | 2.20 | 1.50 | <1e−16 |
| Interleukin-18 binding protein | O95998 | 2.55 | 1.49 | <1e−16 |
| Chordin-Like 1 | Q9BU40 | 2.87 | 1.49 | <1e−16 |
| Cystatin C | P01034 | 3.54 | 1.49 | <1e−16 |
| Complement C9 | P02748 | 2.81 | 1.48 | 8.80E−14 |
| CCL18/PARC | P55774 | 2.55 | 1.47 | 1.11E−16 |
| Complement C7 | P10643 | 3.09 | 1.47 | <1e−16 |
| RELT tumor necrosis factor recepto | Q969Z4 | 3.23 | 1.46 | <1e−16 |
| Jagged- | P78504 | 2.17 | 1.45 | 3.66E−15 |
| Netrin receptor UNC5H3 | O95185 | 3.15 | 1.44 | <1e−16 |
| Ephrin-A4 | P52798 | 3.37 | 1.44 | <1e−16 |
| Brain-specific serine | Q9GZN4 | 2.54 | 1.44 | <1e−16 |

TABLE 14-continued

Table of individual proteins associated with cardiovascular risk. Biomarkers in the CVD9 panel are in bold. If the hazard ratio (HR) is greater than 1, increased levels of the biomarker are associated with increased risk; if the HR is less than 1, decreased levels of the biomarker are associated with increased risk.

| Target | UniProt ID | Q4/Q1 HR | HR per standard deviation | P value for continuous HR |
|---|---|---|---|---|
| protease 4 | | | | |
| Neuroblastoma suppressor of tumorigenicity 1\|DAN | P41271 | 3.24 | 1.43 | <1e−16 |
| Ephrin type-A receptor 2 | P29317 | 2.86 | 1.43 | <1e−16 |
| Spondin-1 | Q9HCB6 | 2.99 | 1.42 | <1e−16 |
| Periostin | Q15063 | 2.11 | 1.40 | 6.08E−12 |
| Vascular endothelial growth factor A | P15692 | 2.43 | 1.40 | 1.02E−12 |
| Scavenger receptor class F member 1 | Q14162 | 2.90 | 1.39 | <1e−16 |
| α1-antichymotrypsin complex | P07288, P01011 | 2.53 | 1.39 | 1.95E−14 |
| Adaptor protein Crk-I | P46108 | 2.71 | 1.39 | <1e−16 |
| Ephrin-A5 | P52803 | 2.35 | 1.37 | 2.89E−15 |
| Endothelial cell-selective adhesion molecule | Q96AP7 | 2.13 | 1.37 | 1.02E−14 |
| Glutathione S-transferase Pi 1 | P09211 | 2.37 | 1.37 | 1.27E−12 |
| Death receptor 6\|DR6 | O75509 | 1.98 | 1.36 | 1.35E−10 |
| Macrophage-capping protein | P40121 | 3.01 | 1.36 | <1e−16 |
| Coiled-coil domain-containing protein 80 | Q76M96 | 2.07 | 1.35 | 1.36E−10 |
| Lymphocyte-activation gene 3 | P18627 | 2.06 | 1.35 | 2.47E−10 |
| Ck-β-8-1\|Macrophage inflammatory protein 3 splice variant | P55773 | 1.84 | 1.35 | 1.26E−08 |
| Elafin | P19957 | 2.18 | 1.35 | 9.09E−12 |
| TIMP-1 | P01033 | 3.94 | 1.34 | <1e−16 |
| HSP 70 | P08107 | 2.08 | 1.34 | 1.24E−10 |
| Stanniocalcin-1 | P52823 | 2.29 | 1.34 | 2.62E−11 |
| Immunoglobulin G Fc region receptor III-B | O75015 | 1.91 | 1.34 | 2.53E−10 |
| Secretory leukocyte protease inhibitor | P03973 | 2.37 | 1.34 | 7.91E−11 |
| TRAIL R4 | Q9UBN6 | 2.02 | 1.33 | 1.29E−09 |
| MMP-3 | P08254 | 2.40 | 1.33 | 1.36E−09 |
| Pancreatic hormonePH | P01298 | 2.19 | 1.33 | 1.18E−10 |
| Conserved dopamine neurotrophic factor | Q49AH0 | 1.82 | 1.32 | 5.46E−10 |
| Cystatin D | P28325 | 2.11 | 1.32 | 9.36E−10 |
| GPVI | Q9HCN6 | 1.79 | 1.32 | 3.09E−09 |
| Cathepsin Z/X/P | Q9UBR2 | 2.07 | 1.32 | 9.36E−10 |
| Delta-like protein 1 | O00548 | 3.28 | 1.31 | <1e−16 |
| MPIF-1 | P55773 | 1.88 | 1.31 | 2.73E−09 |
| Kallikrein 11 | Q9UBX7 | 1.86 | 1.31 | 1.22E−11 |
| Interleukin-1 receptor-like 1\|ST2 | Q01638 | 2.02 | 1.30 | 1.91E−09 |
| Signaling lymphocytic activation molecule 5 | 0.9UIB8 | 2.49 | 1.30 | 9.99E−16 |
| TFF3 | Q07654 | 3.62 | 1.30 | 3.50E−13 |
| PAFAH β subunit | P68402 | 2.41 | 1.29 | 7.94E−14 |
| Insulin-like growth factor-binding protein-1 | P08833 | 1.87 | 1.29 | 1.11E−08 |
| CD48 | P09326 | 2.07 | 1.29 | 4.61E−10 |
| Renin | P00797 | 1.70 | 1.29 | 1.67E−08 |
| Neuroligin 4, X-linked | Q8N0W4 | 2.24 | 1.29 | 1.91E−12 |
| B lymphocyte chemoattractant | O43927 | 2.34 | 1.29 | 1.24E−11 |
| Pregnancy-associated plasma protein-A | Q13219 | 1.69 | 1.29 | 6.82E−08 |
| uPAR | Q03405 | 3.00 | 1.28 | 3.77E−13 |
| resistin | Q9HD89 | 1.77 | 1.28 | 2.26E−08 |
| Fucosyltransferase 5 | Q11128 | 1.55 | 1.28 | 8.30E−07 |
| Stromal cell-derived factor 1 | P48061 | 1.79 | 1.28 | 2.17E−07 |

TABLE 14-continued

Table of individual proteins associated with cardiovascular risk. Biomarkers in the
CVD9 panel are in bold. If the hazard ratio (HR) is greater than 1, increased levels
of the biomarker are associated with increased risk; if the HR is less than 1,
decreased levels of the biomarker are associated with increased risk.

| Target | UniProt ID | Q4/Q1 HR | HR per standard deviation | P value for continuous HR |
|---|---|---|---|---|
| Nidogen | P14543 | 1.67 | 1.28 | 1.11E−07 |
| TNF-like ligand 1A | O95150 | 2.66 | 1.28 | 6.61E−13 |
| High temperature requirement serine peptidase A2 | O43464 | 2.01 | 1.28 | 6.35E−09 |
| Insulin-like growth factor-binding protein-7 | Q16270 | 1.78 | 1.28 | 1.55E−07 |
| Interleukin-1 receptor 1 | P14778 | 1.83 | 1.27 | 1.12E−06 |
| Non-pancreatic secretory phospholipase A2 | P14555 | 1.98 | 1.27 | 5.23E−09 |
| Angiopoietin-related protein 4 | Q9BY76 | 2.84 | 1.27 | 4.93E−11 |
| Fatty acid binding protein, heart-type | P05413 | 2.58 | 1.27 | 1.29E−10 |
| Lipopolysaccharide-binding protein | P18428 | 1.99 | 1.27 | 1.80E−06 |
| Insulin-like growth factor I receptorIGF-I sR | P08069 | 1.75 | 1.27 | 9.87E−07 |
| Tenascin-C | P24821 | 1.89 | 1.27 | 3.14E−07 |
| X-linked ectodysplasin-A2 receptorIXEDAR | Q9HAV5 | 3.64 | 1.27 | <1e−16 |
| Troponin I, cardiac | P19429 | 2.94 | 1.27 | 1.01E−12 |
| Bone sialoprotein 2 | P21815 | 1.79 | 1.27 | 7.52E−08 |
| Insulin-like growth factor-binding protein-6 | P24592 | 2.29 | 1.26 | 3.04E−11 |
| Matrilin-2 | O00339 | 1.89 | 1.26 | 4.44E−07 |
| T-lymphocyte surface antigen Ly-9 | Q9HBG7 | 1.56 | 1.26 | 1.79E−06 |
| Layilin | Q6UX15 | 2.50 | 1.26 | 1.42E−09 |
| dCTP pyrophosphatase 1 | Q9H773 | 1.59 | 1.26 | 7.35E−06 |
| Fibrinogen γ-chain dimer | P02679 | 1.98 | 1.25 | 3.29E−06 |
| EPH receptor B6 | O15197 | 1.79 | 1.25 | 3.26E−09 |
| Carbonic anhydrase III | P07451 | 1.88 | 1.25 | 5.33E−07 |
| Oxidized low-density lipoprotein receptor 1 | P78380 | 1.89 | 1.25 | 2.37E−07 |
| Cystatin SA | P09228 | 1.59 | 1.25 | 2.82E−06 |
| Fibroblast growth factor 7 | P21781 | 2.08 | 1.25 | 2.90E−12 |
| Neurexophilin-1 | P58417 | 0.58 | 0.75 | 1.11E−08 |
| Soggy-1 | Q9UK85 | 0.54 | 0.75 | 2.57E−08 |
| 15-hydroxyprostaglandin dehydrogenase | P15428 | 0.51 | 0.74 | 1.93E−08 |
| Protein C | P04070 | 0.38 | 0.74 | 1.29E−13 |
| Fibroblast activation protein α | Q12884 | 0.49 | 0.74 | 1.47E−06 |
| TWEAK | O43508 | 0.44 | 0.74 | 4.06E−06 |
| Vascular endothelial growth factor receptor 2 | P35968 | 0.47 | 0.74 | 2.21E−10 |
| Complement C1q binding protein | Q07021 | 0.49 | 0.74 | 9.01E−05 |
| Angiostatin | P00747 | 0.48 | 0.73 | 5.89E−11 |
| ErbB3 | P21860 | 0.39 | 0.72 | 2.03E−10 |
| GDF11 | O95390 | 0.41 | 0.72 | 8.75E−09 |
| BMP-1 | P13497 | 0.39 | 0.71 | 2.54E−13 |
| Cell adhesion oncogene-regulated CDO | Q4KMG0 | 0.39 | 0.70 | 9.06E−14 |
| CK-MM | P06732 | 0.45 | 0.70 | 3.60E−11 |
| Carnosine dipeptidase 1 | Q96KN2 | 0.36 | 0.69 | <1e−16 |
| cAMP and cGMP phosphodiesterase 11A | Q9HCR9 | 0.39 | 0.69 | 5.18E−12 |
| CK-MB | P12277 P06732 | 0.41 | 0.69 | 5.06E−13 |
| Cadherin-3 | P22223 | 0.41 | 0.67 | 1.11E−16 |
| Proto-oncogene tyrosine-protein kinase receptor Ret | P07949 | 0.42 | 0.66 | 4.89E−13 |
| α2-Antiplasmin | P08697 | 0.37 | 0.64 | <1e−16 |
| Growth hormone receptor | P10912 | 0.29 | 0.63 | <1e−16 |
| EGF Receptor | P00533 | 0.29 | 0.60 | <1e−16 |

Example 5: GDF11 and FSTL3 Model

Three Cox proportional hazard models were generated and compared.
- GDF11: univariate protein model with GDF11 protein
- FSTL3: univariate protein model with Follistatin-related protein 3 (FSTL3)
- GDF11.FSTL3: combinational protein model with GDF11 and FSTL3

For the comparison between models, ANOVA, Q4/Q1 hazard ratio of linear predictors, NRI of 4-year risk probability, and integrated AUC within 4 years were calculated. The GDF11.FSTL3 model was the best model with all evaluation methods.

Outlier samples were excluded from the analysis. All models were calculated with log transformed with base 10 and standardized.

Before combining two proteins into the model, the Spearman's correlation was applied to check the relationship between GDF11 and FSTL3. The correlation between two proteins is significant (p=3.123–12), but the Spearman's correlation is not strong (rho=−0.2251). Table 15 shows the result of correlation test of R.

TABLE 15

Spearman's correlation test between GDF11 and FSTL3.

Spearman's rank correlation rho
data: gdf11 and fstl3
S = 1.68e+08, p-value = 3.123e−12
alternative hypothesis: true rho is not equal to 0
sample estimates:
rho
−0.2251

Figure 15:
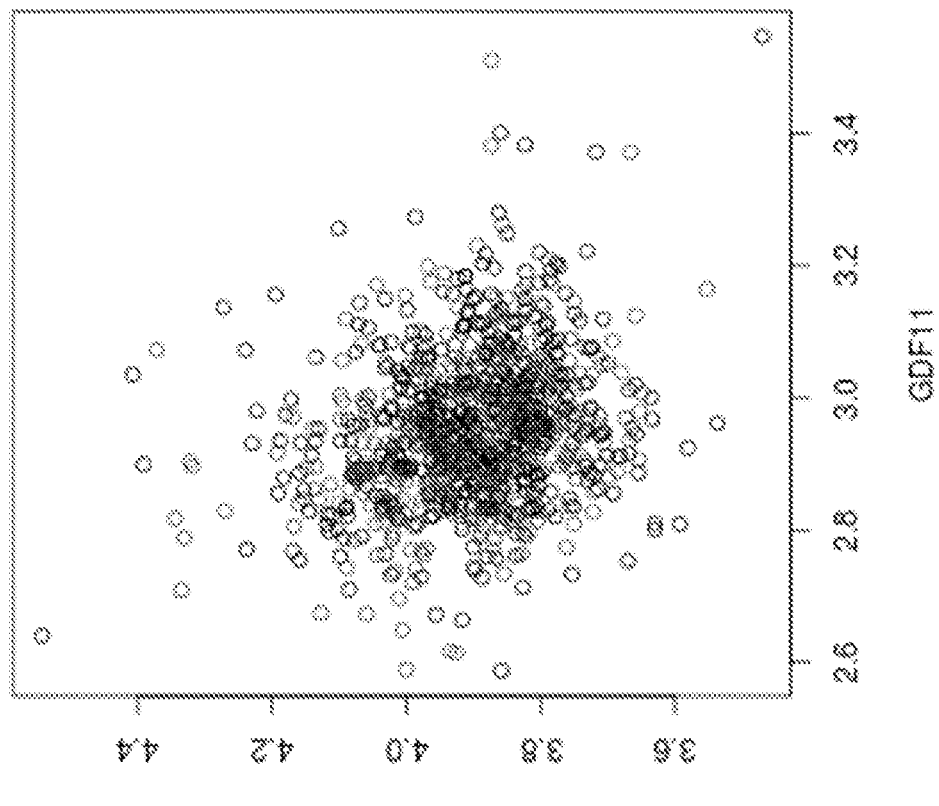
FIG. 15 shows the correlation between GDF11 and FSTL3.
Figure 15:
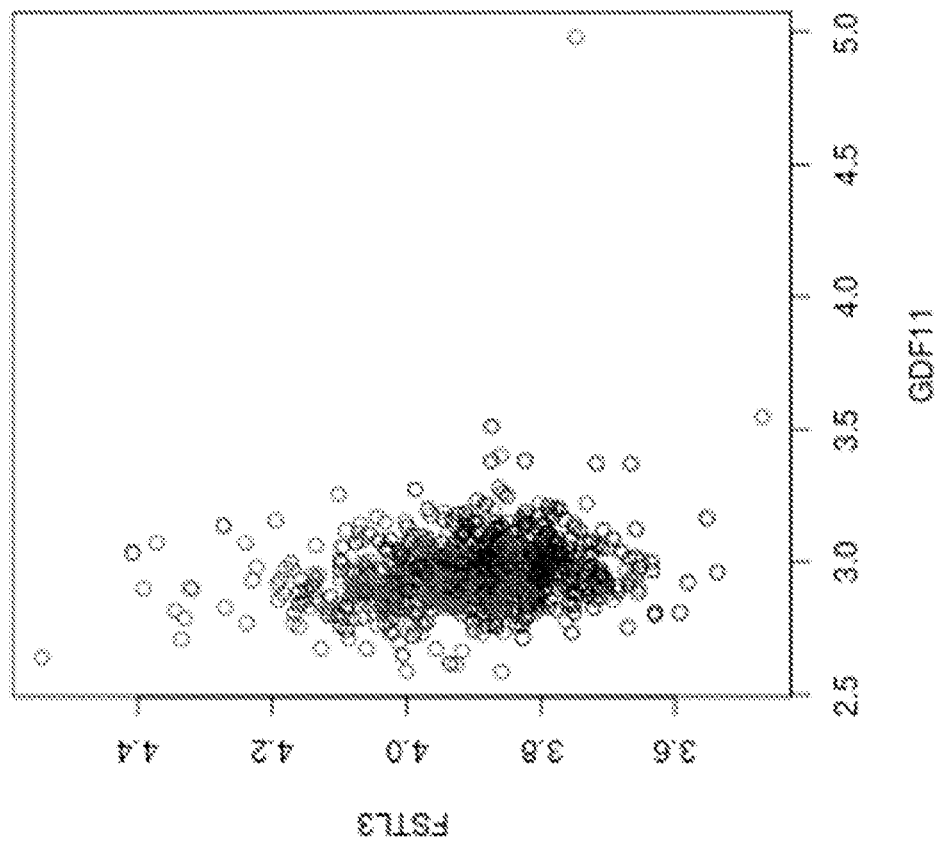

The correlation between GDF11 and FSTL3 is shown in FIG. 15. The RFU was converted to log space with base 10. The left figure shows the correlation of all samples and the right figure shows the correlation without one sample omitted, which had a high GDF11 value. Black and red circles mean no-event samples and event samples, respectively.

Three Cox proportional hazard models were generated: GDF11, FSTL3, and GDF11.FSTL3. The GDF11, FSTL3 models are Cox models with a single protein and the GDF11.FSTL3 is combined model with two proteins. Before fitting the model, the outliers were excluded and RFU values were log transformed and standardized. Tables 16 and 17 shows the comparison between single models and combined model with ANOVA deviance table. The combined model is significantly improved from the single protein models. The p-values for GDF11 vs GDF11.FSTL3 and FSTL3 vs GDF11.FSTL3 are 2e-16 and 3.5e-06, respectively.

TABLE 16

The ANOVA test between GDF11 and GDF11.FSTL3 model

Analysis of Deviance Table
Cox model: response is s
Model 1: ~ GDF11.2765.4.3
Model 2: ~ GDF11.2765.4.3 + FSTL3.3438.10.2
  loglik  Chisq Df P(>|Chi|)
1 −2936
2 −2896  79   1   <2e-16 ***
---
Signif. codes:  0 '*' 0.001 '' 0.01 '*' 0.05 '.' 0.1 ' ' 1

TABLE 17

The ANOVA test between FSTL3 and GDF11.FSTL3 model

Analysis of Deviance Table
Cox model: response is s
Model 1: ~ FSTL3.3438.10.2
Model 2: ~ GDF11.2765.4.3 + FSTL3.3438.10.2
  loglik  Chisq Df P(>|Chi|)
1 −2907
2 −2896  21.5  1  3.5e−06 ***
---
Signif. codes:  0 '*' 0.001 '' 0.01 '*' 0.05 '.' 0.1 ' ' 1

Table 18 shows the Q4/Q1 hazard ratio of linear predictors for each model. The combined model shows a higher hazard ratio than the single models. The quartiles are defined by the linear predictors of each Cox model.

TABLE 18

The Q4/Q1 hazard ratio

|  | Q4/Q1 HR | lower .95 | upper .95 |
|---|---|---|---|
| GDF11 | 2.475 | 1.894 | 3.233 |
| FSTL3 | 3.637 | 2.738 | 4.830 |
| GDF11.FSTL3 | 4.080 | 3.068 | 5.426 |

Figure 16:
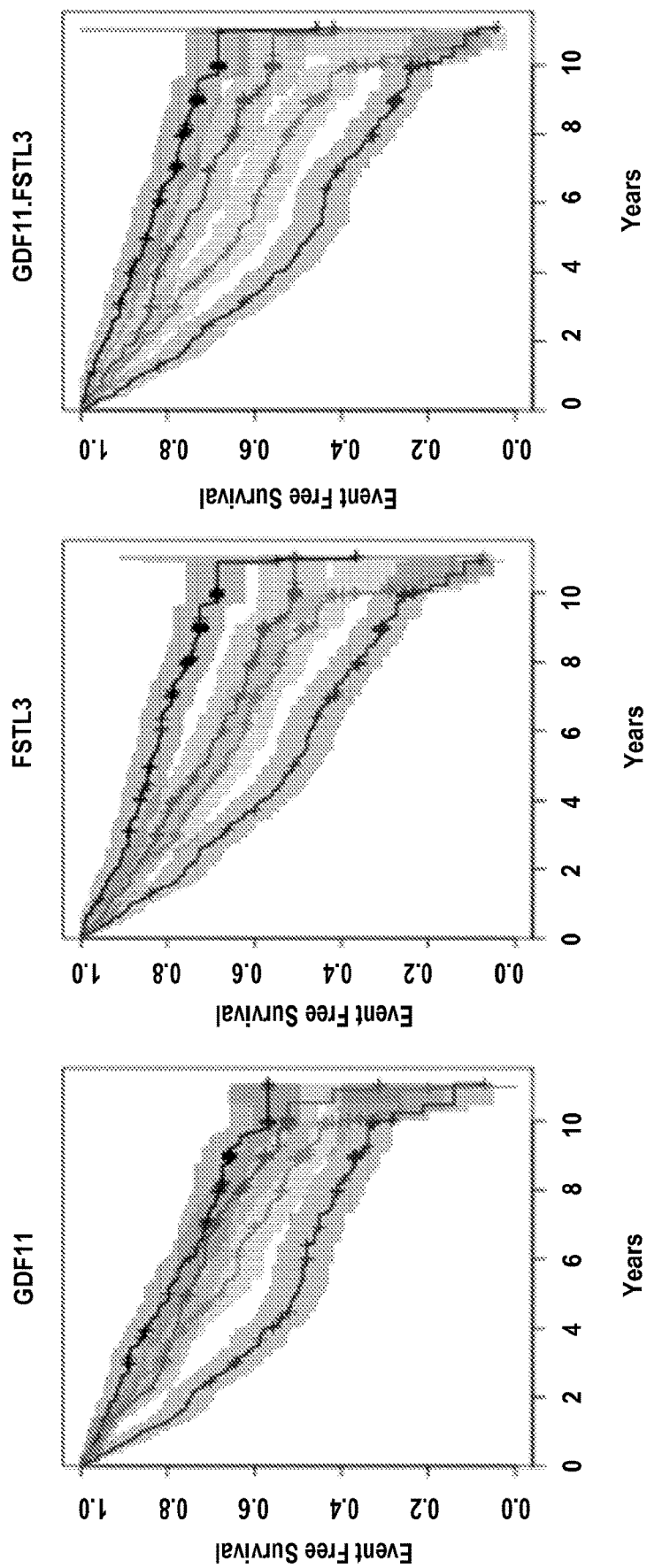
FIG. 16 shows the survival curves for each quartile for each model. The $1^{st}$ to $4^{th}$ quartiles are described with black (top line), red (second line down), green (third line down) and blue (bottom line). The shading shows the 95% confidence intervals. Character "+" means censored samples.
Figure 17:
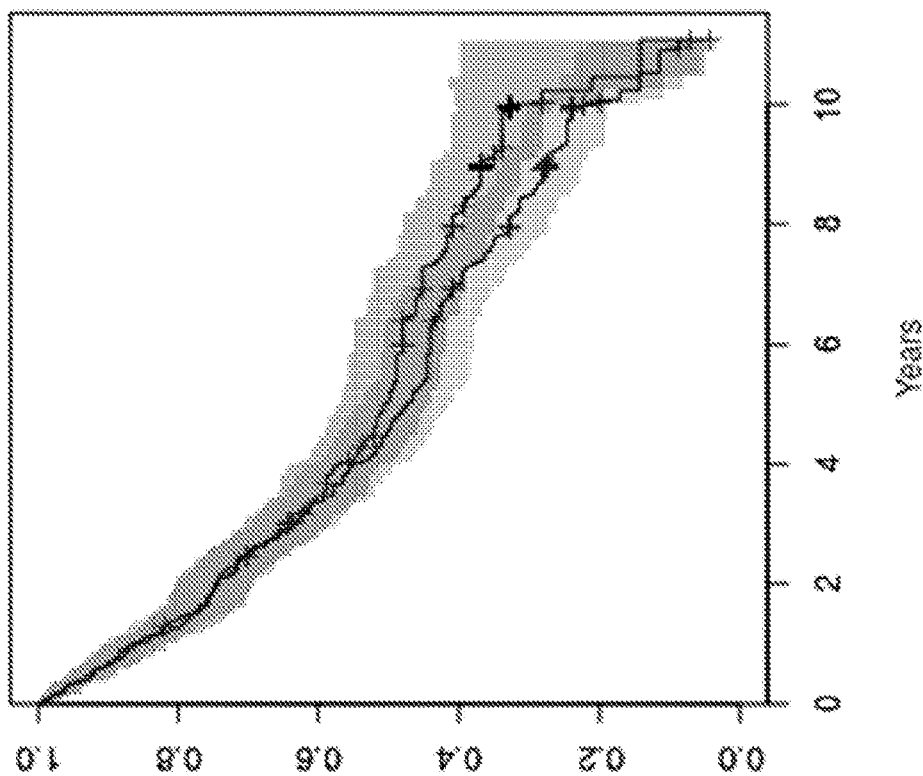
FIG. 17 shows a comparison of the survival curves between GDF11 and GDF11.FSTL3 for the low risk group and the high risk group. In the left panel, the top line represents the GDF11.FSTL3 model and the bottom line represents the GDF11 model. In the right panel, the top line represents the GDF11 model and the bottom line represents the GDF11.FSTL3 model.
Figure 17:
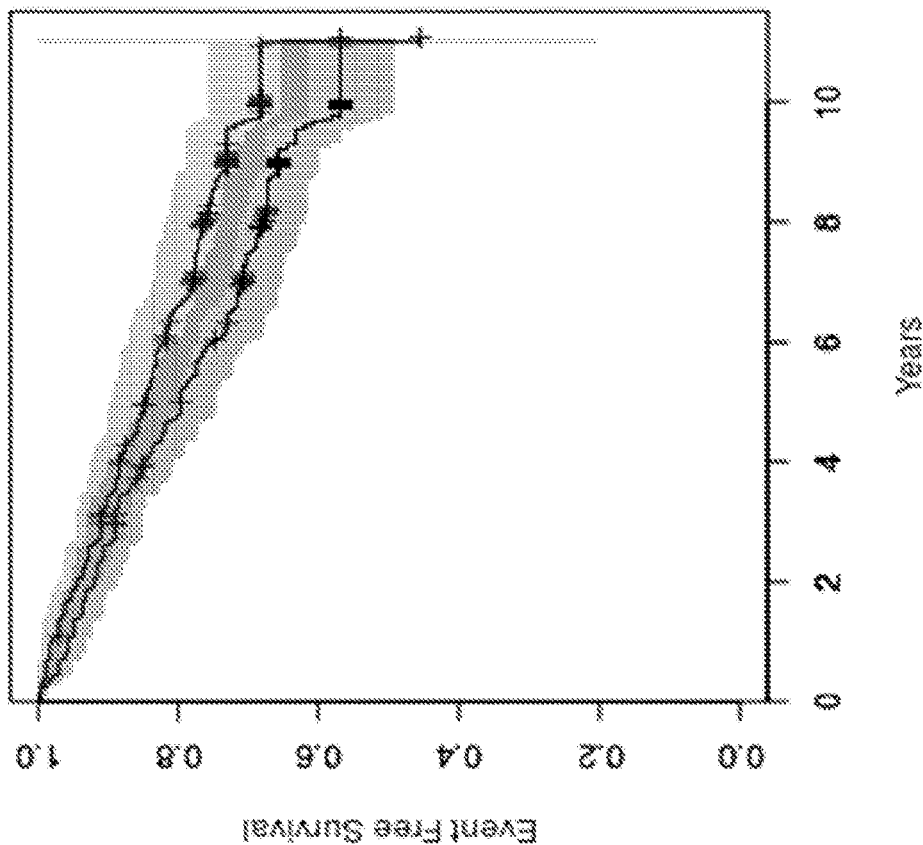

FIG. 16 shows survival curves of each quartile of all models. The $1^{st}$ to $4^{th}$ quartiles are described with black, red, green and blue (from top to bottom, lines are black, red, green, then blue). The shading represents the 95% confidence intervals. The distance between the $1^{st}$ and $4^{th}$ quartiles of the GDF11.FSTL3 model is wider than the single protein models. Moreover, the distance between the $2^{nd}$ and $3^{rd}$ quartiles of the GDF11.FSTL3 model is also wider than the single protein models.

A comparison between the survival curves for the GDF11 model and the GDF11.FSTL3 model is shown in FIG. 3. The left figure shows the comparison of the low risk groups and the right figure shows the comparison of the high risk groups. The black and red represent the GDF11 model and GDF11.FSTL3 model, respectively. In this model, the low risk group identified by the GDF11.FSTL3 model has fewer event samples than the low risk group identified by the GDF11 model, and the high risk group identified by the GDF11.FSTL3 model had more event samples than the high risk group identified by the GDF11 model. The GDF11.FSTL3 model was therefore more accurate for both groups of samples. The inclusion of FSTL3 improved the model for both high and low risk groups.

The NRI was calculated between the single protein models GDF11 and FSTL3 and GDF11.FSTL3. The probability was calculated within 4 years and baseline hazard was estimated with Kaplan-Meier estimator. Lower and Upper in the table are the 95% confidence interval of NRI, which is estimated with bootstrapping. GDF11 improves NRI of event samples and FSTL3 improves NM of non-event samples.

TABLE 19

NIR between single protein model and GDF11.FSTL3 model.

| | GDF11 vs GDF11.FSTL3 | | | | FSTL3 vs GDF11.FSTL3 | | |
|---|---|---|---|---|---|---|---|
| | Estimate | Lower | Upper | | Estimate | Lower | Upper |
| NRI | 0.4326 | 0.28552 | 0.5772 | NRI | 0.31532 | 0.17287 | 0.4639 |
| NRI+ | 0.1446 | 0.01143 | 0.2655 | NRI+ | 0.22840 | 0.10174 | 0.3612 |
| NRI− | 0.2880 | 0.21878 | 0.3563 | NRI− | 0.08692 | 0.01022 | 0.1653 |
| Pr(Up\|Case) | 0.5721 | 0.50573 | 0.6329 | Pr(Up\|Case) | 0.61422 | 0.55081 | 0.6807 |
| Pr(Down\|Case) | 0.4276 | 0.36706 | 0.4942 | Pr(Down\|Case) | 0.38582 | 0.31923 | 0.4491 |
| Pr(Down\|Ctrl) | 0.6441 | 0.60935 | 0.6780 | Pr(Down\|Ctrl) | 0.54345 | 0.50504 | 0.5828 |
| Pr(Up\|Ctrl) | 0.3560 | 0.32190 | 0.3906 | Pr(Up\|Ctrl) | 0.45653 | 0.41738 | 0.4949 |

Figure 18:
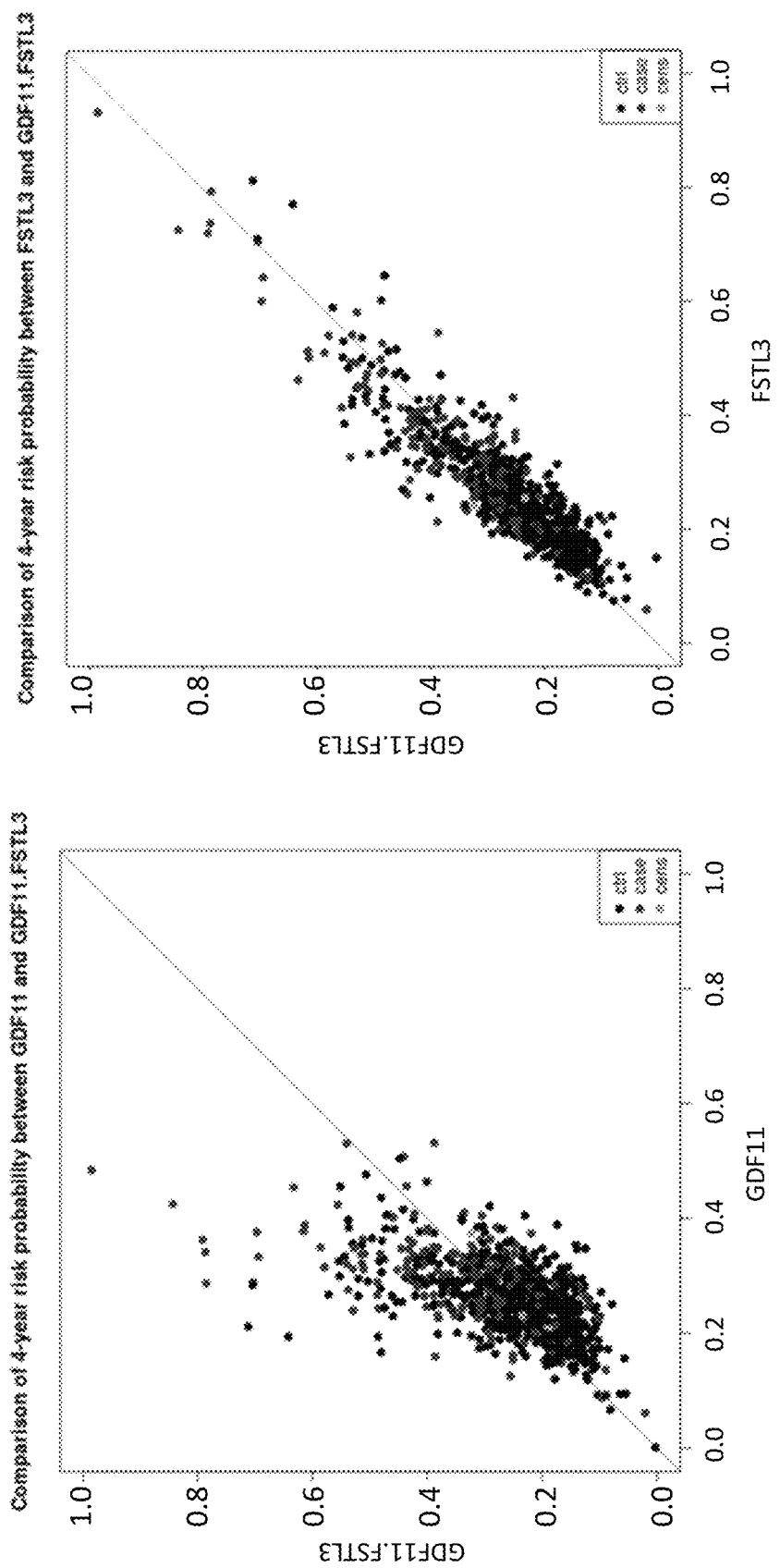
FIG. 18 shows a comparison of the 4-year probability between GDF11 and GDF11.FSTL3 (left) and between FSTL3 and GDF11.FSTL3 (right).

FIG. 18 shows the comparison of 4-year probability between GDF11 and GDF11.FSTL3 (left), and FSTL3 and GDF11.FSTL3 (right). Black, red, and green dots describe control, case, and censored samples at year 4.

The integrated AUC (Cindex) within 4 years is shown in Table 20. 95% confidence intervals were calculated with bootstrapping, similar to NM.

TABLE 20

The integrated AUC (Cindex) within 4 years.

| | Cindex | lower.95 | upper.95 |
|---|---|---|---|
| GDF11 | 0.5882 | 0.5555 | 0.6096 |
| FSTL3 | 0.6038 | 0.5786 | 0.6321 |
| GDF11.FSTL3 | 0.6286 | 0.6050 | 0.6566 |

Figure 19:
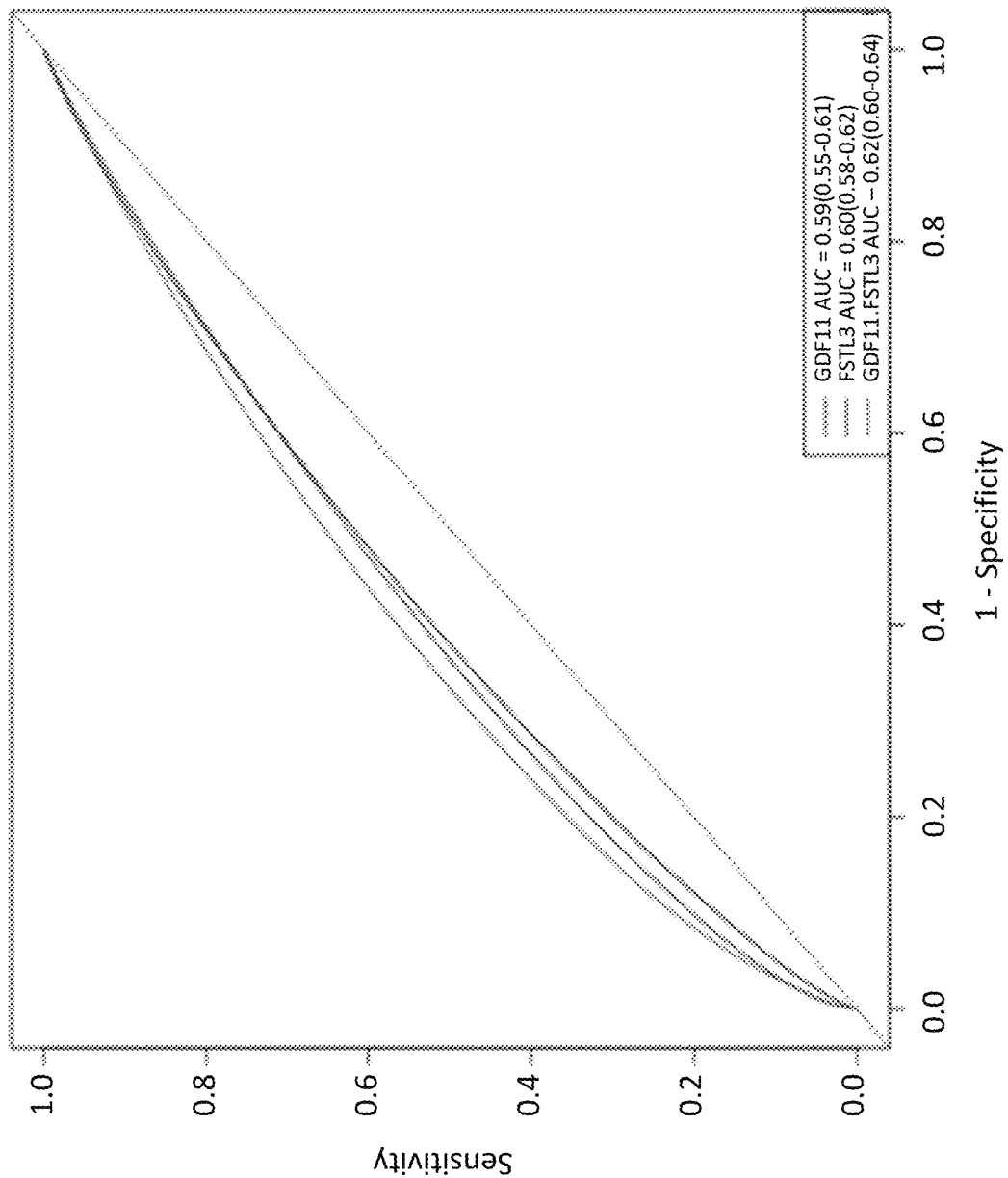
FIG. 19 shows the ROC curve at year 4 for the three models.
Figure 20:
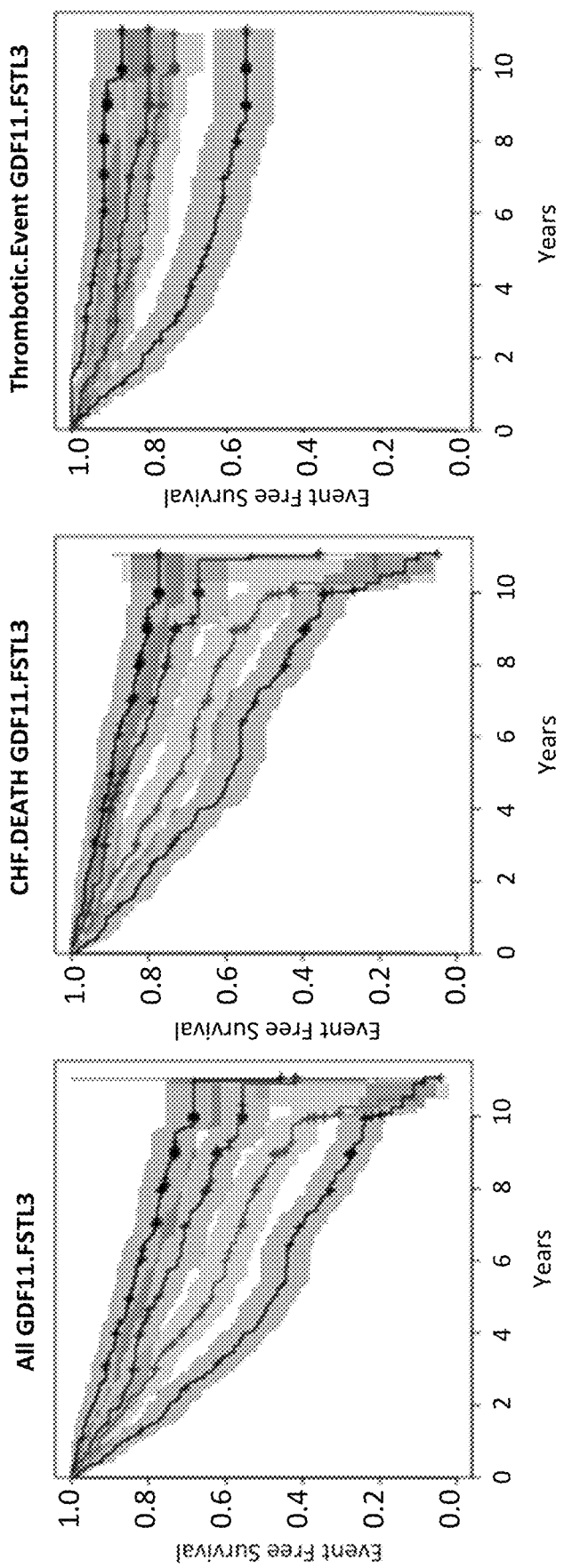
FIG. 20 shows survival curves for each quartile of linear predictor of each group (all, CHF-Death, and thrombotic event) of the GDF11.FSTL3 model. The $1^{st}$ to $4^{th}$ quartiles are described with black (top line), red (second line down), green (third line down) and blue (bottom line). The shading shows the 95% confidence intervals.

The ROC curves at year 4 are shown in FIG. 19. The numbers in in the legend refer to the AUC at year 4 (not integrated AUC).

Three Cox proportional hazard models were compared with several evaluation statistics, for the single marker models and the combination marker model. The combinational model, which includes GDF11 and FSTL3, performed the best according to all evaluation values.

The following shows the three models used in this example.
Call:
coxph(formula=f, data=x, x=T)
 n=937, number of events=465
  coef exp(coef) se(coef) z Pr(>|z|)
GDF11.2765.4.3−0.3452 0.7081 0.0579−5.96 2.5e−09 ***
- - -
Signif. codes: 0 '*' 0.001 '' 0.01 '*' 0.05 '.' 0.1 ' ' 1
 exp(coef) exp(−coef) lower 0.95 upper 0.95
GDF11.2765.4.3 0.708 1.41 0.632 0.793
Concordance=0.604 (se=0.014)
Rsquare=0.04 (max possible=0.998)
Likelihood ratio test=38.1 on 1 df, p=6.66e−10
Wald test=35.6 on 1 df, p=2.46e−09
Score (logrank) test=28.4 on 1 df, p=9.95e−08
Call:
coxph(formula=f, data=x, x=T)
 n=937, number of events=465
  coef exp(coef) se(coef) z Pr(>|z|)
FSTL3.3438.10.2 0.436 1.547 0.042 10.4<2e−16 ***
- - -
Signif. codes: 0 '*' 0.001 '' 0.01 '*' 0.05 '.' 0.1 ' ' 1
 exp(coef) exp(−coef) lower 0.95 upper 0.95
FSTL3.3438.10.2 1.55 0.646 1.42 1.68
Concordance=0.634 (se=0.014)
Rsquare=0.097 (max possible=0.998)
Likelihood ratio test=95.6 on 1 df, p=0
Wald test=108 on 1 df, p=0
Score (logrank) test=105 on 1 df, p=0
Call:
coxph(formula=f, data=x, x=T)
 n=937, number of events=465
  coef exp(coef) se(coef) z Pr(>|z|)
GDF11.2765.4.3−0.2605 0.7706 0.0577−4.52 6.2e−06 ***
FSTL3.3438.10.2 0.4064 1.5014 0.0434 9.36<2e−16 ***
- - -
Signif. codes: 0 '*' 0.001 '' 0.01 '*' 0.05 '.' 0.1 ' ' 1
 exp(coef) exp(−coef) lower 0.95 upper 0.95
GDF11.2765.4.3 0.771 1.298 0.688 0.863
FSTL3.3438.10.2 1.501 0.666 1.379 1.635
Concordance=0.652 (se=0.014)
Rsquare=0.117 (max possible=0.998)
Likelihood ratio test=117 on 2 df, p=0
Wald test=124 on 2 df, p=0
Score (logrank) test=119 on 2 df, p=0

Example 6: GDF11 and FSTL3 Model for Specific Event Groups

The Cox models of GDF11, FSTL3, and GDF11.FSTL3 were fitted with CHF and Death samples, and thrombotic event samples separately, to determine how the model performs for each CV event type. Q4/Q1 hazard ratio of linear predictors of the model, integrated AUC (Cindex) within 4 years, and NRI of 4 year risk probability were calculated. For the calculation of risk probability, Kaplan-Meier estimator was used as baseline hazard.

We fitted the Cox proportional hazard model with GDF11, FSTL3, and GDF11.FSTL3 with specific event groups: CHF and Death group, and thrombotic event group. CHF and Death group includes CHF(125), CVDDeath(55), Death (135) and NONE(472). Thrombotic event group includes MI(104), STROKE(30), TIA(16) and NONE(472). NONE, which are non-event samples, were used in both groups. For the evaluation of models, Q4/Q1 hazard ratio of linear predictors, integrated AUC within 4 years, and NRI of 4 year risk probability were calculated. Risk probability was calculated with baseline hazard of Kaplan-Meier estimator.

Table 21 shows the Q4/Q1 hazard ratio, inverse of hazard ratio and its 95% confidence intervals. Q4/Q1 hazard ratio of GDF11 and FSTL3 are not significantly different between DHF.DEATH and Thrombotic event samples, but the hazard ratio of GDF11.FSTL3 is better with thrombotic event groups than CHF.DEATH group.

TABLE 21

Q4/Q1 hazard ratio of each model and group.

|  | Q4/Q1 HR | Q1/Q4 HR | CI Lower | CI Upper |
|---|---|---|---|---|
| $GDF11 | | | | |
| All | 2.475 | 0.4040 | 1.894 | 3.233 |
| CHF.DEATH | 2.726 | 0.3668 | 1.964 | 3.784 |
| Thrombotic.Event | 2.743 | 0.3645 | 1.698 | 4.432 |
| $FSTL3 | | | | |
| All | 3.637 | 0.2750 | 2.738 | 4.830 |
| CHF.DEATH | 4.478 | 0.2233 | 3.125 | 6.416 |
| Thrombotic.Event | 4.605 | 0.2171 | 2.731 | 7.765 |
| $GDF11.FSTL3 | | | | |
| All | 4.080 | 0.2451 | 3.068 | 5.426 |
| CHF.DEATH | 4.394 | 0.2276 | 3.069 | 6.291 |
| Thrombotic.Event | 5.493 | 0.1821 | 3.185 | 9.473 |

FIG. 1 shows survival curves of quartiles of linear predictor of each group of GDF11.FSTL3 model. The $1^{st}$ to $4^{th}$ quartiles are described with black (top line), red (second line down), green (third line down) and blue (bottom line). The shading shows the 95% confidence intervals. The $1^{st}$ quartile of thrombotic event (low risk group) shows fewer events. This suggests that the model could be quite sensitive to the thrombotic event.

Integrated AUC (Cindex) within 4 years and 95% confidence intervals are shown in Table 22. With Cindex, there are no significant differences between CHF.DEATH group and Thrombotic event group, even though the Q4/Q1 hazard ratio was found to be different between groups.

TABLE 22

Integrated AUC (Cindex) within 4 years

|  | Cindex | Cindex.CI.lower.95 | Cindex.CI.upper.95 |
|---|---|---|---|
| $GDF11 | | | |
| All | 0.5882 | 0.5614 | 0.6165 |
| CHF.DEATH | 0.5892 | 0.5582 | 0.6220 |
| Thrombotic.Event | 0.6057 | 0.5641 | 0.6503 |
| $FSTL3 | | | |
| All | 0.6038 | 0.5808 | 0.6344 |
| CHF.DEATH | 0.6018 | 0.5754 | 0.6482 |
| Thrombotic.Event | 0.5994 | 0.5667 | 0.6600 |
| $GDF11.FSTL3 | | | |
| All | 0.6286 | 0.6047 | 0.6558 |
| CHF.DEATH | 0.6308 | 0.6020 | 0.6645 |
| Thrombotic.Event | 0.6292 | 0.5939 | 0.6777 |

In conclusion, the Cox model of GDF11, FSTL3, and GDF11.FSTL3 were generated with specific sample groups. The GDF11.FSTL3 model shows the best result with Q4/Q1 hazard ratio with thrombotic event group. With Cindex, all models showed similar results.

Example 7: GDF11 and GASP1/GASP2 Model

The combination of GDF11 with two other proteins, GASP1 (WFIKKN2, SwissProt Q8TEU8) and GASP2 (WFIKKN1, SwissProt Q96D09), was also tested.

The following four Cox models were generated: (1) GDF11, Cox model with GDF11 protein; (2) GDF11.WFIKKN1, Cox model with GDF11 and GASP2; (3) GDF11.WFIKKN2, Cox model with GDF11 and GASP1; and (4) GDF11.WFIKKN1.WFIKKN2, Cox model with GDF11, GASP1, and GASP2. Before creating the models, the protein measurement was standardized to Gaussian(0,1).

Figure 21:
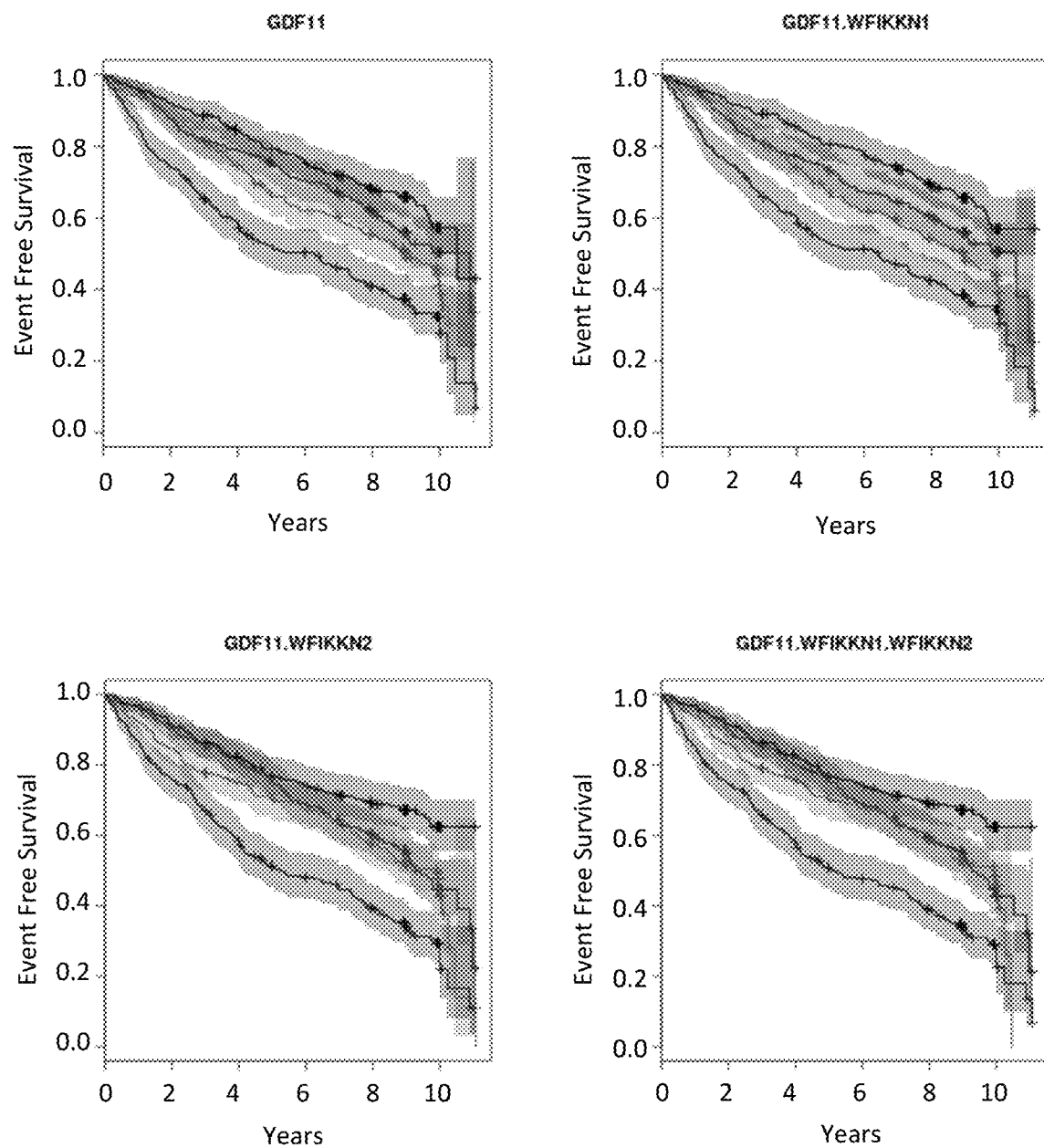
FIG. 21 shows the survival curves for each quartile for the models GDF11, GDF11.WFIKKN1, GDF11.WFIKKN2, and GDF11.WFIKKN1.WFIKKN2.

Q4/Q1 hazard ratio of linear predictors was calculated for the models. The Q1 group is assumed as low risk group and the Q4 group is assumed as high risk group. Adding GASP2 (WFIKKN1) was found not to improve the GDF11 model, but adding WFIKKN2 showed some improvement (from 2.432 to 2.719). The values of Q4/Q1 hazard ratio and survival curves of quartiles are shown in Table 23 and FIG. 21.

TABLE 23

Q4/Q1 hazard ratio of each model.

| ## | Q4/Q1 HR | Q1/Q4 HR | CI Lower | CI Upper |
|---|---|---|---|---|
| ## GDF11 | 2.432 | 0.4111 | 1.864 | 3.175 |
| ## GDF11.WFIKKN1 | 2.392 | 0.4180 | 1.830 | 3.127 |
| ## GDF11.WFIKKN2 | 2.719 | 0.3678 | 2.071 | 3.569 |
| ## GDF11.WFIKKN1.WFIKKN2 | 2.758 | 0.3626 | 2.102 | 3.619 |

In addition, the models were compared with ANOVA deviance tables. The R result of comparison between GDF11 and the combined models are shown below. GDF11.WFIKKN2 and GDF11.WFIKKN1.WFIKKN2 were significant when compared to the GDF11 model (p=3.1e-05, 0.00015, respectively). Adding WFIKKN1 did not show significance (p=0.38). The p values are highlighted below.

- Comparison between GDF11 and GDF11.WFIKKN1
  ## Analysis of Deviance Table
  ## Cox model: response is s
  ## Model 1: ~ GDF11.2765.4.3
  ## Model 2: ~ GDF11.2765.4.3 + WFIKKN1.3191.50.2
  ##    loglik Chisq Df P(>|Chi|)
  ## 1  -2938
  ## 2  -2937  0.77  1     0.38
- Comparison between GDF11 and GDF11.WFIKKN2
  ## Analysis of Deviance Table
  ## Cox model: response is s
  ## Model 1: ~ GDF11.2765.4.3
  ## Model 2: ~ GDF11.2765.4.3 + WFIKKN2.3235.50.2
  ##    loglik Chisq Df P(>|Chi|)
  ## 1  -2938
  ## 2  -2929  17.4  1    3.1e-05 ***
  ## ---
  ## Signif. codes:  0 '*' 0.001 '' 0.01 '*' 0.05 '.' 0.1 ' ' 1
- Comparison between GDF11 and GDF11.WFIKKN1.WFIKKN2
  ## Analysis of Deviance Table
  ## Cox model: response is s
  ## Model 1: ~ GDF11.2765.4.3
  ## Model 2: ~ GDF11.2765.4.3 + WFIKKN1.3191.50.2 + WFIKKN2.3235.50.2
  ##    loglik Chisq Df P(>|Chi|)
  ## 1  -2938
  ## 2  -2929  17.6  2    0.00015 ***
  ## ---
  ## Signif. codes:  0 '*' 0.001 '' 0.01 '*' 0.05 '.' 0.1 ' ' 1

For evaluating the models, NRI calculation was also performed. The probability was calculated within 4 years. Adding GASP1(WFIKKN2) improved NRI (0.16), particularly with non-event samples (0.12). From this result, GASP1 may be able to improve true negative rate. In contrast, GASP2 didn't improve NRI more than 0.1. The R result of NRI is shown below.

- NRI between GDF11 and GDF11.WFIKKN1
```
--- GDF11 vs GDF11.WFIKKN1 ---
Estimate    Lower     Upper
NRI           0.05855  -0.08109   0.20126
NRI+          0.09245  -0.02881   0.20405
NRI-         -0.03391  -0.11142   0.04671
Pr(Up|Case)   0.54627   0.48586   0.60175
Pr(Down|Case) 0.45382   0.39769   0.51467
Pr(Down|Ctrl) 0.48303   0.44431   0.52336
Pr(Up|Ctrl)   0.51694   0.47665   0.55573
```
- NRI between GDF11 and GDF11.WFIKKN2
```
--- GDF11 vs GDF11.WFIKKN2 ---
Estimate    Lower    Upper
NRI           0.16315   0.02639   0.3063
NRI+          0.04422  -0.07236   0.1727
NRI-          0.11892   0.04351   0.1919
Pr(Up|Case)   0.52206   0.46394   0.5861
Pr(Down|Case) 0.47784   0.41338   0.5363
Pr(Down|Ctrl) 0.55948   0.52176   0.5960
Pr(Up|Ctrl)   0.44056   0.40405   0.4783
```
- NRI between GDF11 and GDF11.WFIKKN1.WFIKKN2
```
--- GDF11 vs GDF11.WFIKKN1.WFIKKN2 ---
Estimate    Lower    Upper
NRI           0.13460  -0.01276   0.2759
NRI+          0.02732  -0.09310   0.1643
NRI-          0.10728   0.02863   0.1758
Pr(Up|Case)   0.51364   0.45354   0.5820
Pr(Down|Case) 0.48632   0.41779   0.5467
Pr(Down|Ctrl) 0.55365   0.51428   0.5879
Pr(Up|Ctrl)   0.44637   0.41211   0.4857
```

Figure 22:
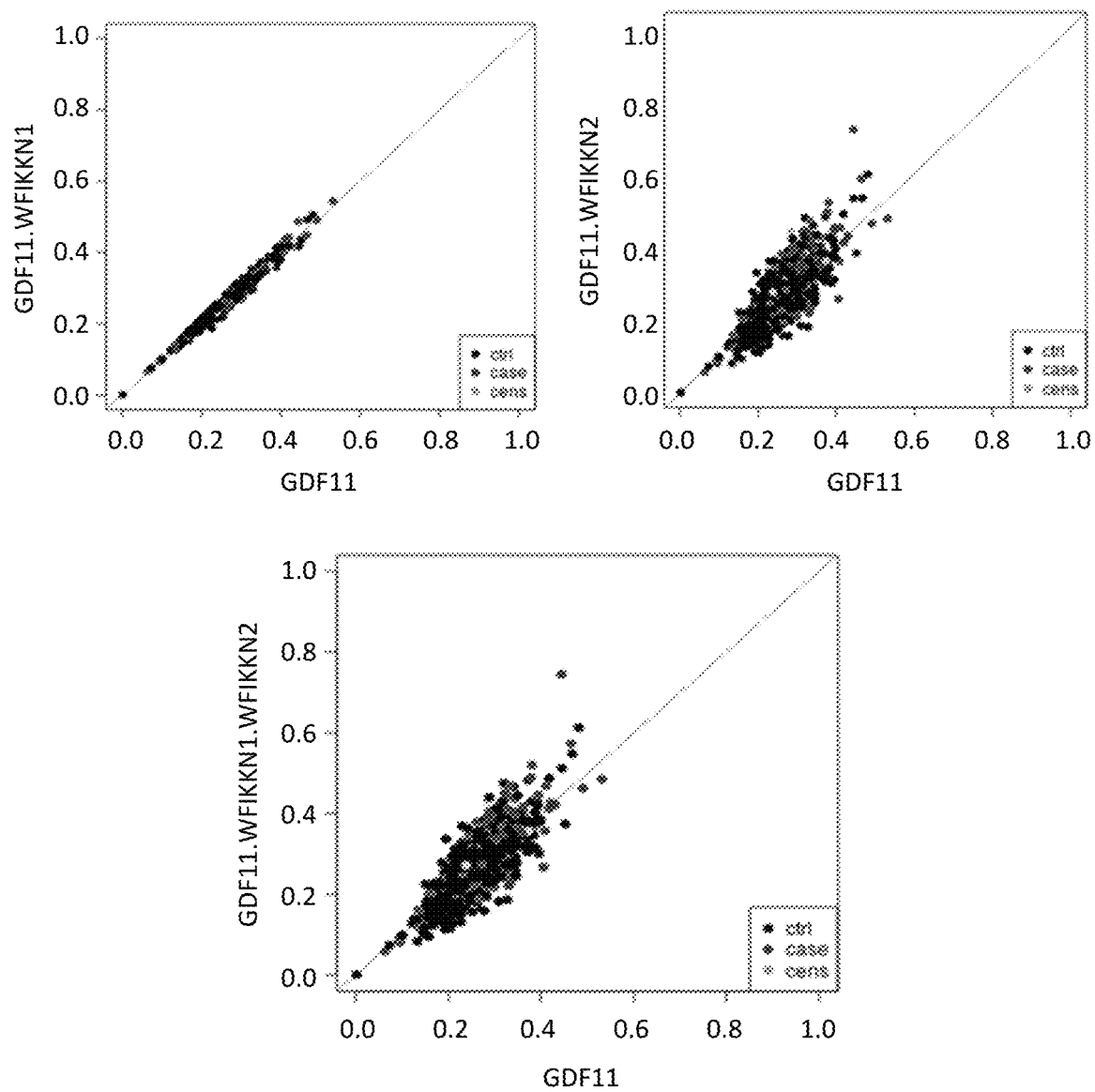
FIG. 22 shows the risk probability between the GDF11 model and GDF11.WFIKKN1, GDF11.WFIKKN2, and GDF11.WFIKKN1.WFIKKN2 models.

The 4-year-probability between models is shown in FIG. 22.

Figure 23:
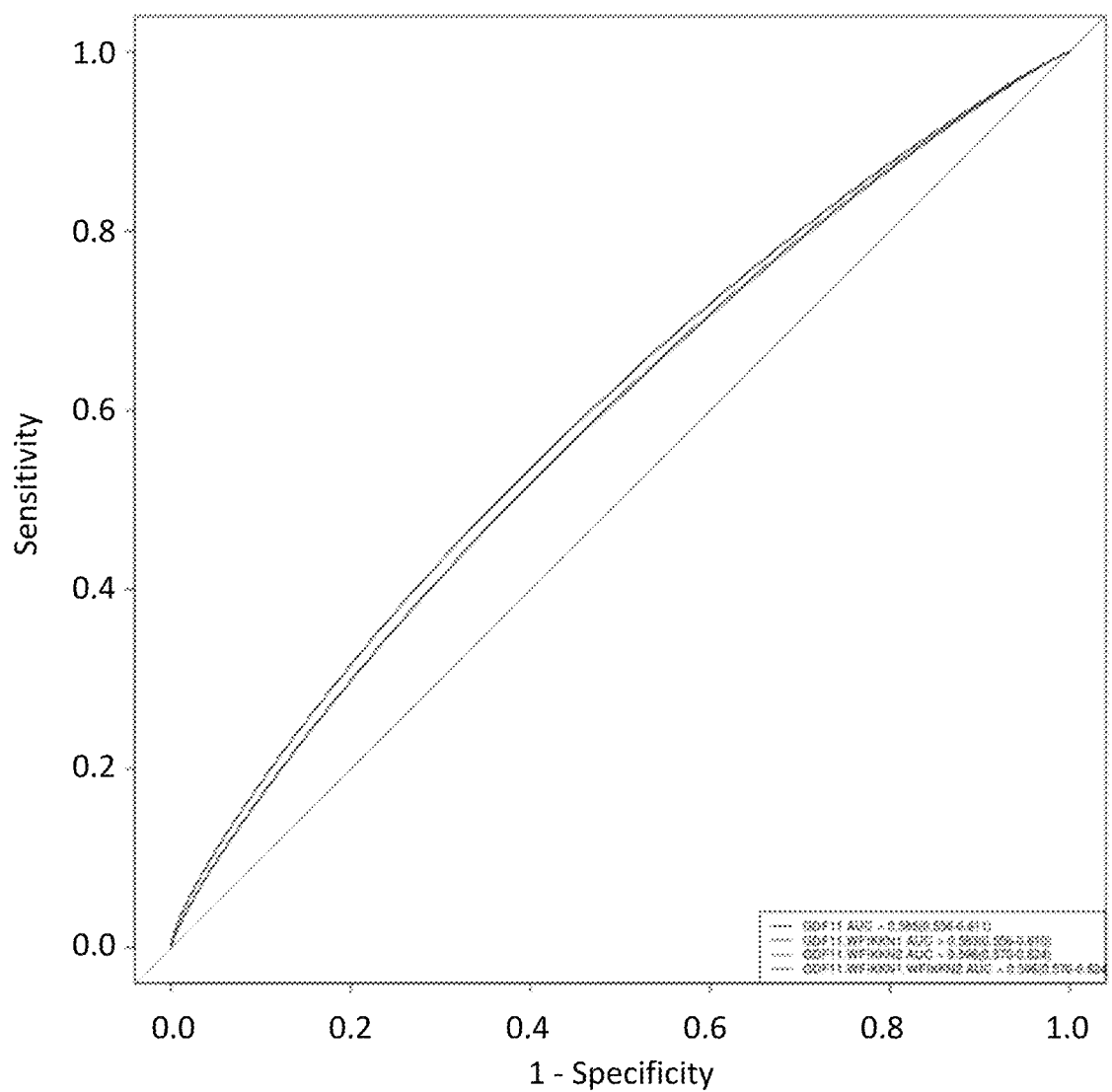
FIG. 23 shows the ROC curves for each model: GDF11, GDF11.WFIKKN1, GDF11.WFIKKN2, and GDF11.WFIKKN1.WFIKKN2.

Finally, AUC calculation was performed for the evaluation between models. According to below results, neither protein improved the GDF11 model. The ROC curves for each model are shown in FIG. 23. The ROC curves for each model were similar.

- GDF11
```
----- -----
Cindex  lower.95  upper.95
1  0.586    0.5579    0.6143
```
- GDF11.WFIKKN1
```
----- -----
Cindex  lower.95  upper.95
1  0.5849   0.5572    0.6133
```
- GDF11.WFIKKN2
```
----- -----
Cindex  lower.95  upper.95
1  0.5994   0.5717    0.6305
```
- GDF11.WFIKKN1.WFIKKN2
```
----- -----
Cindex  lower.95  upper.95
1  0.5988   0.5712    0.63
```

In summary, GASP1 (WFKKN2) may improve the GDF11 model, but he improvement is small. GASP2 (WFKKN1) did not improve the GDF11 model.

The Cox model used in this example is shown below.

- GDF11
```
Call:
coxph(formula = f, data = x, x = T)

n = 938, number of events = 465

coef  exp(coef)  se(coef)     z   Pr(>|z|)
GDF11.2765.4.3  -0.3325    0.7171    0.0578  -5.75  8.7e-09 ***
---
Signif. codes:  0 '*' 0.001 '' 0.01 '*' 0.05 '.' 0.1 ' ' 1

exp(coef) exp(-coef) lower .95 upper .95
GDF11.2765.4.3    0.717     1.39       0.64      0.803

Concordance = 0.602  (se = 0.014)
Rsquare = 0.037   (max possible = 0.998)
Likelihood ratio test = 35.6  on 1 df,   p = 2.42e-09
Wald test             = 33.1  on 1 df,   p = 8.75e-09
Score (logrank) test  = 26.6  on 1 df,   p = 2.53e-07
```
- GDF11.WFIKKN1
```
Call:
coxph(formula = f, data = x, x = T)

n = 938, number of events = 465

coef  exp(coef)  se(coef)      z   Pr(>|z|)
GDF11.2765.4.3    -0.3206   0.7257    0.0590   -5.43  5.6e-08 ***
WFIKKN1.3191.50.2 -0.0409   0.9599    0.0466   -0.88   0.38
---
Signif. codes:  0 '*' 0.001 '' 0.01 '*' 0.05 '.' 0.1 ' ' 1

exp(coef) exp(-coef) lower .95 upper .95
GDF11.2765.4.3      0.726     1.38       0.646     0.815
WFIKKN1.3191.50.2   0.960     1.04       0.876     1.052

Concordance = 0.601  (se = 0.014)
Rsquare = 0.038   (max possible = 0.998)
Likelihood ratio test = 36.4  on 2 df,   p = 1.26e-08
Wald test             = 34.3  on 2 df,   p = 3.55e-08
Score (logrank) test  = 28.8  on 2 df,   p = 5.65e-07
```
- GDF11.WFIKKN2
```
Call:
coxph(formula = f, data = x, x = T)

n = 938, number of events = 465

```

```
coef   exp(coef)  se(coef)    z   Pr(>|z|)
GDF11.2765.4.3        -0.3369    0.7140    0.0575  -5.86  4.6e-09 ***
WFIKKN2.3235.50.2      0.2014    1.2232    0.0484   4.16  3.2e-05 ***
---
Signif. codes:  0 '*' 0.001 '' 0.01 '*' 0.05 '.' 0.1 ' ' 1

exp(coef) exp(-coef) lower .95 upper .95
GDF11.2765.4.3         0.714     1.401     0.638     0.799
WFIKKN2.3235.50.2      1.223     0.818     1.112     1.345

Concordance = 0.609  (se = 0.014)
Rsquare = 0.055   (max possible = 0.998)
Likelihood ratio test = 53   on 2 df,   p = 3.18e-12
Wald test             = 50.7 on 2 df,   p = 9.63e-12
Score (logrank) test  = 42.1 on 2 df,   p = 7.26e-10
• GDF11.WFIKKN1.WFIKKN2
Call:
coxph(formula = f, data = x, x = T)

n = 938, number of events = 465

coef   exp(coef)  se(coef)    z   Pr(>|z|)
GDF11.2765.4.3        -0.3294    0.7193    0.0589  -5.60  2.2e-08 ***
WFIKKN1.3191.50.2     -0.0256    0.9747    0.0466  -0.55  0.58
WFIKKN2.3235.50.2      0.1989    1.2201    0.0486   4.10  4.2e-05 ***
---
Signif. codes:  0 '*' 0.001 '' 0.01 '*' 0.05 '.' 0.1 ' ' 1

exp(coef) exp(-coef) lower .95 upper .95
GDF11.2765.4.3         0.719     1.39      0.641     0.807
WFIKKN1.3191.50.2      0.975     1.03      0.890     1.068
WFIKKN2.3235.50.2      1.220     0.82      1.109     1.342

Concordance = 0.609  (se = 0.014)
Rsquare = 0.055   (max possible = 0.998)
Likelihood ratio test = 53.2 on 3 df,   p = 1.62e-11
Wald test             = 51.4 on 3 df,   p = 4.1e-11
Score (logrank) test  = 43.7 on 3 df,   p = 1.73e-09
```

What is claimed is:

1. A method of detecting levels of a set of biomarkers in a sample from a subject, comprising:
   (a) contacting a sample from the subject with a set of capture reagents, wherein the set of capture reagents comprises at least two and up to nine capture reagents, wherein each capture reagent specifically binds to a different biomarker protein, wherein one capture reagent specifically binds to ErbB3, and wherein at least one capture reagent specifically binds to a biomarker protein selected from MMP12, GDF11, and TFF3; and
   (b) detecting the amount of each capture reagent bound to the biomarker protein to which it specifically binds.

2. The method of claim 1, further comprising predicting the likelihood that the subject will have a cardiovascular (CV) event.

3. The method of claim 1, further comprising screening the subject for the risk of a cardiovascular event (CV) event.

4. The method of claim 2, wherein the likelihood of the subject having a CV event within 4 years is high if the level of at least ErbB3 is higher than a control level of ErbB3, and if the level of GDF11 is lower than a control level of GDF11.

5. The method of claim 3, wherein the CV event is a thrombotic event.

6. The method of claim 5, wherein the thrombotic event is selected from myocardial infarction, stroke, and transient ischemic attack.

7. The method of claim 1, wherein the subject has coronary artery disease.

8. The method of claim 1, wherein the subject does not have a history of cardiovascular (CV) events.

9. The method of claim 8, wherein the subject has a high American College of Cardiology (ACC) risk score.

10. The method of claim 8, wherein the subject has an intermediate ACC risk score.

11. The method of claim 8, wherein the subject has a low ACC risk score.

12. The method of claim 1, wherein the subject has had at least one cardiovascular (CV) event.

13. The method of claim 1, wherein the CV event is selected from myocardial infarction, stroke, congestive heart failure, transgenic ischemic attack, and death.

14. The method of claim 1, wherein the sample is selected from a blood sample, a serum sample, a plasma sample, and a urine sample.

15. The method of claim 14, wherein the sample is a plasma sample.

16. The method of claim 1, wherein each biomarker capture reagent is an antibody or an aptamer.

17. The method of claim 16, wherein each biomarker capture reagent is an aptamer.

18. The method of claim 17, wherein at least one aptamer is a slow off-rate aptamer.

19. The method of claim 18, wherein at least one slow off-rate aptamer comprises at least one nucleotide with a modification.

20. The method of claim 19, wherein each slow off-rate aptamer binds to its target protein with an off rate ($t_{1/2}$) of ≥30 minutes.

21. The method of claim 2, wherein the likelihood of a CV event is based on the biomarker levels and at least one item of additional biomedical information selected from a) information corresponding to the presence of cardiovascular risk factors selected from the group consisting of prior myocardial infarction, angiographic evidence of greater than 50% stenosis in one or more coronary vessels, exercise-induced ischemia by treadmill or nuclear testing or prior coronary revascularization,
b) information corresponding to physical descriptors of said individual,
c) information corresponding to a change in weight of said individual,
d) information corresponding to the ethnicity of said individual,
e) information corresponding to the gender of said individual,
f) information corresponding to said individual's smoking history,
g) information corresponding to said individual's alcohol use history,
h) information corresponding to said individual's occupational history,
i) information corresponding to said individual's family history of cardiovascular disease or other circulatory system conditions,
j) information corresponding to the presence or absence in said individual of at least one genetic marker correlating with a higher risk of cardiovascular disease in said individual or a family member of said individual,
k) information corresponding to clinical symptoms of said individual,
l) information corresponding to other laboratory tests,
m) information corresponding to gene expression values of said individual, and
n) information corresponding to said individual's consumption of known cardiovascular risk factors such as diet high in saturated fats, high salt, high cholesterol,
o) information corresponding to the individual's imaging results obtained by techniques selected from the group consisting of electrocardiogram, echocardiography, carotid ultrasound for intima-media thickness, flow mediated dilation, pulse wave velocity, ankle-brachial index, stress echocardiography, myocardial perfusion imaging, coronary calcium by CT, high resolution CT angiography, MRI imaging, and other imaging modalities,
p) information regarding the individual's medications, and
q) information regarding the individual's kidney function.

22. The method of claim 1, wherein the method comprises determining the likelihood of a CV Event for the purpose of determining a medical insurance premium or life insurance premium.

23. The method of claim 22, wherein the method further comprises determining coverage or premium for medical insurance or life insurance.

24. The method of claim 1, wherein the method further comprises using information resulting from the method to predict and/or manage the utilization of medical resources.

25. The method of claim 1, wherein the method further comprises using information resulting from the method to enable a decision to acquire or purchase a medical practice, hospital, or company.

26. The method of claim 1, wherein the set of capture reagents comprises at least three capture reagents, wherein one capture reagent specifically binds to ErbB3, and at least two capture reagents each specifically binds to a biomarker protein selected from MMP12, GDF11, and TFF3, wherein each of the capture reagents binds to a different biomarker protein.

27. The method of claim 1, wherein the set of capture reagents comprises at least four capture reagents, wherein a first capture reagent specifically binds ErbB3, a second capture reagent specifically binds MMP12, a third capture reagent specifically binds GDF11, and a fourth capture reagents specifically binds TFF3.

* * * * *